United States Patent
Kadron et al.

(10) Patent No.: US 11,690,702 B2
(45) Date of Patent: Jul. 4, 2023

(54) URINARY CATHETER PROSTHESES

(71) Applicant: RAMBAM MEDTECH LTD., Haifa (IL)

(72) Inventors: Amnon Kritzman Kadron, Pardes Hannah Karkur (IL); Ilan Gruenwald, Haifa (IL); Yehuda Yarmut, Yokneam Moshava (IL); Arie Oscar Holtz, Jerusalem (IL); Nir Sinai, Alon Ha-Galil (IL)

(73) Assignee: RAMBAM MEDTECH LTD., Haifa (IL)

( * ) Notice: Subject to any disclaimer, the term of this patent is extended or adjusted under 35 U.S.C. 154(b) by 0 days.

(21) Appl. No.: 17/441,140

(22) PCT Filed: Jan. 26, 2021

(86) PCT No.: PCT/IL2021/050085
§ 371 (c)(1),
(2) Date: Sep. 20, 2021

(87) PCT Pub. No.: WO2021/152580
PCT Pub. Date: Aug. 5, 2021

(65) Prior Publication Data
US 2022/0370180 A1 Nov. 24, 2022

Related U.S. Application Data

(60) Provisional application No. 63/040,565, filed on Jun. 18, 2020, provisional application No. 62/995,470, filed on Jan. 30, 2020.

(51) Int. Cl.
*A61F 2/00* (2006.01)
*A61M 25/00* (2006.01)
*A61M 25/04* (2006.01)

(52) U.S. Cl.
CPC ....... *A61F 2/0022* (2013.01); *A61M 25/0075* (2013.01); *A61M 25/04* (2013.01); *A61M 2025/0079* (2013.01)

(58) Field of Classification Search
CPC ............ A61F 2/0004–0027; A61F 2/04; A61F 2/042; A61F 2002/047; A61M 25/0017;
(Continued)

(56) References Cited

U.S. PATENT DOCUMENTS

| 3,472,230 A | 10/1969 | Fogarty |
| 4,154,243 A | 5/1979 | Patel et al. |

(Continued)

FOREIGN PATENT DOCUMENTS

| EP | 0407218 | 3/1995 |
| EP | 2001398 | 5/2010 |

(Continued)

OTHER PUBLICATIONS

Miyazato, M., Yoshimura, N., & Chancellor, M. B. (2013). The other bladder syndrome: underactive bladder. Reviews in urology, 15(1), 11.
(Continued)

*Primary Examiner* — Thaddeus B Cox
(74) *Attorney, Agent, or Firm* — Sughrue Mion, PLLC

(57) ABSTRACT

A user-controllable urinary catheter prosthesis (20) is provided for minimally-invasive insertion into a subject. The prosthesis (20) includes a proximal intra-urethral assembly (22), configured to be inserted entirely within a urethra (102) via a meatus (104). A user-activatable hydraulic activator (50) is disposed along a flexible intra-urethral catheter (30, 430), which is shaped so as to define a urinary outlet (40, 440) at a proximal end (41, 441) thereof. A distal bladder assembly (32, 132, 232, 332) is configured to be disposed in a bladder of the subject, and includes a bladder anchor (48).

(Continued)

A hydraulic valve (60, 160, 260, 360) is configured to assume an open state, in which urine flow is allowed between the distal bladder assembly (32, 132, 232, 332) and the urinary outlet (40, 440); and a closed resting state, in which urine is entirely blocked from entering the distal bladder assembly (32, 132, 232, 332) and exiting the urinary outlet (40, 440). Application of pressure to the hydraulic activator (50) transitions the hydraulic valve (60, 160, 260, 360) from the closed resting state to the open state. Other embodiments are also described.

28 Claims, 35 Drawing Sheets

(58) Field of Classification Search
CPC ....... A61M 25/0075; A61M 2025/0076–0078; A61M 2025/0079
See application file for complete search history.

(56) References Cited

U.S. PATENT DOCUMENTS

| | | | |
|---|---|---|---|
| 4,553,533 A | 11/1985 | Leighton | |
| 5,762,599 A | 6/1998 | Sohn | |
| 5,795,288 A | 8/1998 | Cohen et al. | |
| 6,119,697 A * | 9/2000 | Engel ............... | A61F 2/0027 |
| | | | 128/885 |
| 6,855,126 B2 | 2/2005 | Flinchbaugh | |
| 7,666,133 B2 | 2/2010 | Drager | |
| 7,674,852 B2 | 3/2010 | Müller et al. | |
| 7,682,390 B2 | 3/2010 | Seguin | |
| 7,691,078 B2 | 4/2010 | Rioux et al. | |
| 7,695,427 B2 | 4/2010 | Kugler et al. | |
| 7,749,280 B2 | 7/2010 | Rioux et al. | |
| 7,758,542 B2 | 7/2010 | Whalen et al. | |
| 7,766,899 B2 | 8/2010 | Bolmsjö et al. | |
| 7,766,901 B2 | 8/2010 | Mroncz et al. | |
| 7,776,053 B2 | 8/2010 | Strecker | |
| 7,918,815 B2 | 4/2011 | Rioux et al. | |
| 7,918,882 B2 | 4/2011 | Pavcnik et al. | |
| 7,951,064 B2 | 5/2011 | Whalen et al. | |
| 7,998,055 B2 | 8/2011 | Siegel et al. | |
| 8,007,458 B2 | 8/2011 | Lennox et al. | |
| 8,096,938 B2 | 1/2012 | Forsell et al. | |
| 8,096,939 B2 | 1/2012 | Forsell | |
| 8,187,164 B2 | 5/2012 | Kugler et al. | |
| 8,292,800 B2 | 10/2012 | Stone et al. | |
| 8,317,853 B2 | 11/2012 | Agnew | |
| 8,485,963 B2 | 7/2013 | Comiter et al. | |
| 8,500,625 B2 | 8/2013 | Goria | |
| 8,556,796 B2 | 10/2013 | Forsell | |
| 8,652,026 B2 | 2/2014 | Zunker et al. | |
| 8,672,910 B1 | 3/2014 | Kaufman | |
| 8,702,587 B2 | 4/2014 | Comiter et al. | |
| 8,721,520 B2 | 5/2014 | Caira et al. | |
| 8,758,428 B2 | 6/2014 | Bates et al. | |
| 8,801,594 B2 | 8/2014 | Fogarty | |
| 8,808,369 B2 | 8/2014 | Suri | |
| 8,845,514 B2 | 9/2014 | Siegel et al. | |
| 8,852,079 B2 | 10/2014 | Sandstrom | |
| 8,858,460 B2 | 10/2014 | Connors et al. | |
| 8,864,647 B2 | 10/2014 | Buie et al. | |
| 8,864,649 B2 | 10/2014 | Cahill et al. | |
| 8,874,234 B2 | 10/2014 | Carlsson et al. | |
| 8,876,800 B2 | 11/2014 | Behan | |
| 8,882,653 B2 | 11/2014 | Gillespie, Jr. et al. | |
| 8,887,731 B2 | 11/2014 | Zipper | |
| 8,888,676 B2 | 11/2014 | Ziv et al. | |
| 8,911,344 B2 | 12/2014 | Altan et al. | |
| 8,911,347 B2 | 12/2014 | Browning | |
| 8,920,304 B2 | 12/2014 | Suslian et al. | |
| 8,920,445 B2 | 12/2014 | Sholev | |
| 8,920,483 B2 | 12/2014 | Swanick et al. | |
| 8,920,515 B2 | 12/2014 | Cook et al. | |
| 8,920,516 B2 | 12/2014 | Cook et al. | |
| 8,926,493 B2 | 1/2015 | Karapasha | |
| 8,926,496 B2 | 1/2015 | Andarawis et al. | |
| 8,926,497 B2 | 1/2015 | Deegan et al. | |
| 8,932,200 B2 | 1/2015 | Cotner et al. | |
| 8,932,202 B2 | 1/2015 | Browning | |
| 8,932,262 B2 | 1/2015 | Ostfeld et al. | |
| 8,961,392 B2 | 2/2015 | Cao et al. | |
| 8,979,733 B2 | 3/2015 | Crabtree et al. | |
| 8,986,188 B2 | 3/2015 | Vecchiotti et al. | |
| 8,986,370 B2 | 3/2015 | Annest | |
| 8,992,410 B2 | 3/2015 | Behan | |
| 8,992,412 B2 | 3/2015 | Cahill et al. | |
| 9,011,314 B2 | 4/2015 | Davis et al. | |
| 9,011,522 B2 | 4/2015 | Annest | |
| 9,017,245 B2 | 4/2015 | Forsell | |
| 9,022,920 B2 | 5/2015 | Weiser et al. | |
| 9,022,921 B2 | 5/2015 | Thiefelder et al. | |
| 9,022,922 B2 | 5/2015 | Knoll | |
| 9,044,209 B2 | 6/2015 | Dayton et al. | |
| 9,050,163 B2 | 6/2015 | Goldberg et al. | |
| 9,056,181 B2 | 6/2015 | Watson | |
| 9,072,585 B2 | 7/2015 | Merade et al. | |
| 9,072,586 B2 | 7/2015 | Ranucci et al. | |
| 10,010,392 B1 * | 7/2018 | Zukowski ............. | A61F 2/0009 |
| 10,238,314 B2 | 3/2019 | Connolly et al. | |
| 2006/0195009 A1 | 8/2006 | Drager | |
| 2010/0076573 A1 | 3/2010 | Kugler et al. | |
| 2010/0145138 A1 | 6/2010 | Forsell | |
| 2010/0145139 A1 | 6/2010 | Forsell | |
| 2010/0152862 A1 | 6/2010 | Rioux et al. | |
| 2010/0203100 A1 | 8/2010 | Cobian et al. | |
| 2010/0240948 A1 | 9/2010 | Siegel et al. | |
| 2010/0312225 A1 | 12/2010 | Armistead | |
| 2010/0331608 A1 | 12/2010 | Trubiano | |
| 2011/0015758 A1 | 1/2011 | Lennox et al. | |
| 2011/0028778 A1 | 2/2011 | Kunz | |
| 2011/0071506 A1 | 3/2011 | Gardner et al. | |
| 2011/0098684 A1 | 4/2011 | Trubiano | |
| 2011/0213408 A1 | 9/2011 | Gross et al. | |
| 2011/0257471 A1 | 10/2011 | Siegel et al. | |
| 2012/0108889 A1 | 5/2012 | Behan | |
| 2013/0211185 A1 | 8/2013 | Hull, Jr. et al. | |
| 2013/0218065 A1 | 8/2013 | Watson | |
| 2013/0274545 A1 | 10/2013 | Jenkins | |
| 2013/0274546 A1 | 10/2013 | Anderson et al. | |
| 2013/0296639 A1 | 11/2013 | Lamson et al. | |
| 2013/0303841 A1 | 11/2013 | Fogarty | |
| 2014/0005469 A1 | 1/2014 | Yao et al. | |
| 2014/0031611 A1 | 1/2014 | Forsell | |
| 2014/0039244 A1 | 2/2014 | Browning | |
| 2014/0039245 A1 | 2/2014 | Ziv | |
| 2014/0039248 A1 | 2/2014 | Browning | |
| 2014/0041672 A1 | 2/2014 | García | |
| 2014/0046123 A1 | 2/2014 | Connors et al. | |
| 2014/0046124 A1 | 2/2014 | Cahill et al. | |
| 2014/0046125 A1 | 2/2014 | Gillespie, Jr. et al. | |
| 2014/0051917 A1 | 2/2014 | Browning | |
| 2014/0073844 A1 | 3/2014 | Morningstar | |
| 2014/0081075 A1 | 3/2014 | Salama | |
| 2014/0100418 A1 | 4/2014 | Deegan et al. | |
| 2014/0107403 A1 | 4/2014 | Witzmann et al. | |
| 2014/0128662 A1 | 5/2014 | Deitch et al. | |
| 2014/0128664 A1 | 5/2014 | Ogdahl et al. | |
| 2014/0128666 A1 | 5/2014 | Shapiro et al. | |
| 2014/0135572 A1 | 5/2014 | Zunker et al. | |
| 2014/0194676 A1 | 7/2014 | Comiter et al. | |
| 2014/0236208 A1 | 8/2014 | Cahill et al. | |
| 2014/0243584 A1 | 8/2014 | Bercovich | |
| 2014/0257020 A1 | 9/2014 | Smith et al. | |
| 2014/0257021 A1 | 9/2014 | Chu | |
| 2014/0257024 A1 | 9/2014 | Chu et al. | |
| 2014/0288360 A1 | 9/2014 | Knoll | |
| 2014/0303431 A1 | 10/2014 | Suslian et al. | |
| 2015/0025302 A1 | 1/2015 | Browning | |
| 2015/0038779 A1 | 2/2015 | Sacks | |
| 2015/0059777 A1 | 3/2015 | Guardia | |
| 2015/0087896 A1 | 3/2015 | Wei et al. | |
| 2015/0112188 A1 | 4/2015 | Stigall et al. | |

(56) References Cited

U.S. PATENT DOCUMENTS

| | | |
|---|---|---|
| 2015/0112230 A1 | 4/2015 | Iglesias |
| 2015/0141743 A1 | 5/2015 | Deitch et al. |
| 2015/0148588 A1 | 5/2015 | Connors et al. |
| 2015/0148589 A1 | 5/2015 | Crabtree et al. |
| 2015/0148591 A1 | 5/2015 | Joshi et al. |
| 2015/0150668 A1 | 6/2015 | Behan |
| 2015/0173880 A1 | 6/2015 | Knight |
| 2015/0173881 A1 | 6/2015 | Pregenzer et al. |
| 2018/0153671 A1 | 6/2018 | Herrera et al. |

FOREIGN PATENT DOCUMENTS

| | | |
|---|---|---|
| EP | 1592363 | 10/2010 |
| EP | 2679197 | 1/2014 |
| WO | 2001/010358 | 2/2001 |
| WO | 2004/062532 | 7/2004 |
| WO | 2005/074384 | 8/2005 |
| WO | 2007/138590 | 12/2007 |
| WO | 2008/055248 | 5/2008 |
| WO | 2009/000081 | 12/2008 |
| WO | 2009/152609 | 12/2009 |
| WO | 2010/067300 | 6/2010 |
| WO | 2010/080021 | 7/2010 |
| WO | 2010/117471 | 10/2010 |
| WO | 2010/148504 | 12/2010 |
| WO | 2010/149341 | 12/2010 |
| WO | 2011/041123 | 4/2011 |
| WO | 2011/115876 | 9/2011 |
| WO | 2012/059906 | 5/2012 |
| WO | 2012/104848 | 8/2012 |
| WO | 2012/106602 | 8/2012 |
| WO | 2012/107141 | 8/2012 |
| WO | 2012/120326 | 9/2012 |
| WO | 2012/141923 | 10/2012 |
| WO | 2012/142058 | 12/2012 |
| WO | 2012/167030 | 12/2012 |
| WO | 2013/135792 | 9/2013 |
| WO | 2014/026028 | 2/2014 |
| WO | 2014/040198 | 3/2014 |
| WO | 2014/090227 | 6/2014 |
| WO | 2015/048119 | 4/2015 |
| WO | 2016/182777 | 11/2016 |
| WO | 2019/051114 | 3/2019 |

OTHER PUBLICATIONS

An International Search Report and a Written Opinion both dated Apr. 18, 2021, which issued during the prosecution of Applicant's PCT/IL2021/050085.

Vakalopoulos, I., Kampantais, S., Laskaridis, L., Chachopoulos, V., Koptsis, M., & Toutziaris, C. (2012). New artificial urinary sphincter devices in the treatment of male iatrogenic incontinence. Advances in urology, 2012.

"About Your Artificial Urinary Sphincter," Memorial Sloan Kettering Cancer Center, Patient & Caregiver Education (Oct. 2019).

"The In-Flow™ Intraurethral Valve-Pump," Marketing Presentation, SRS Medical Systems, Inc. (Mar. 2011).

"Urinary Incontinence: UriControl®," Product Overview, Implantica Management AG (downloaded Oct. 1, 2021).

"InFlow™ Intraurethral Valve-Pump," Product Overview, Vesiflo Inc. (downloaded Mar. 18, 2020).

U.S. Appl. No. 63/040,565, filed Jun. 18, 2020.
U.S. Appl. No. 62/995,470, filed Jan. 30, 2020.

* cited by examiner

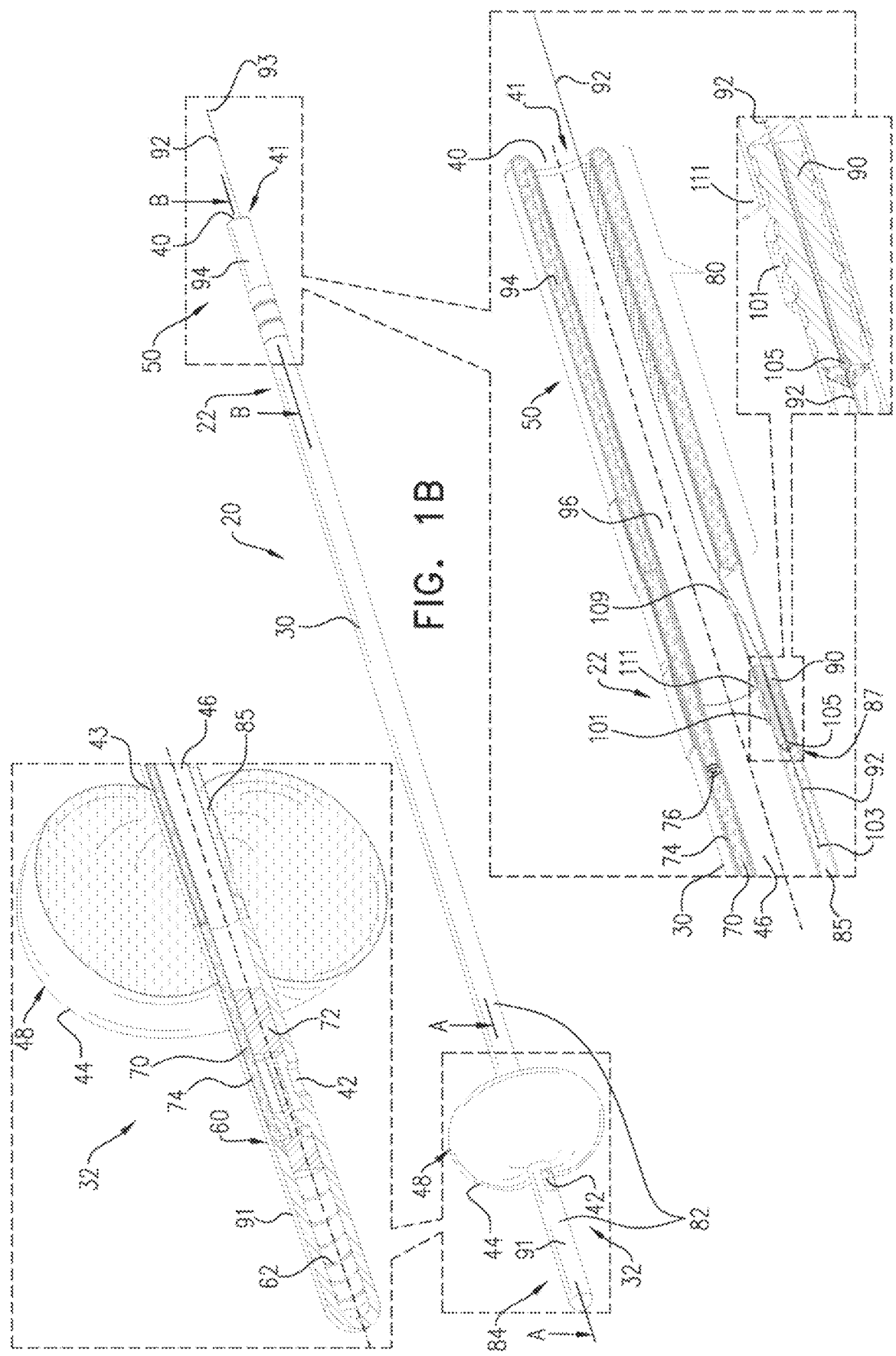

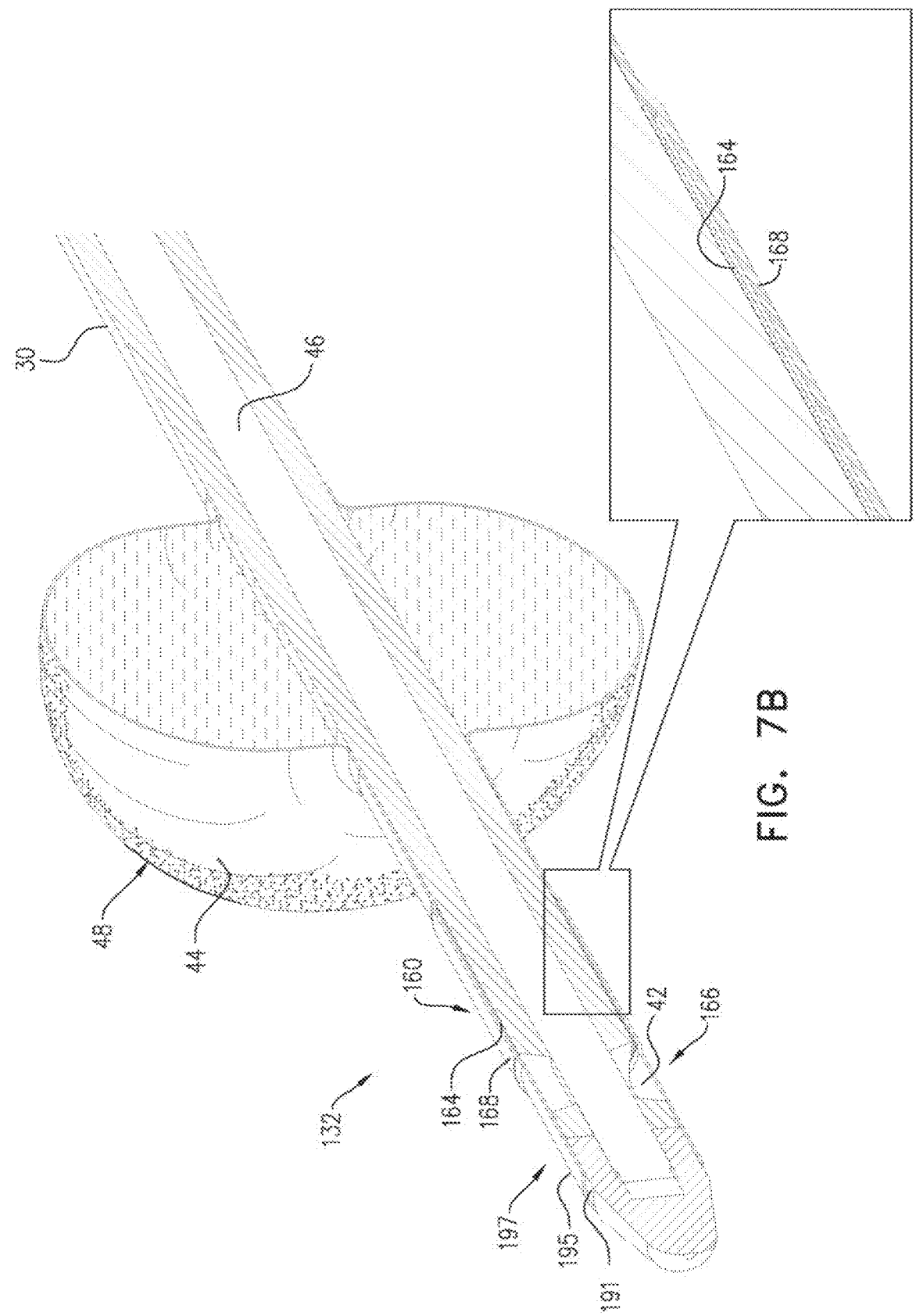

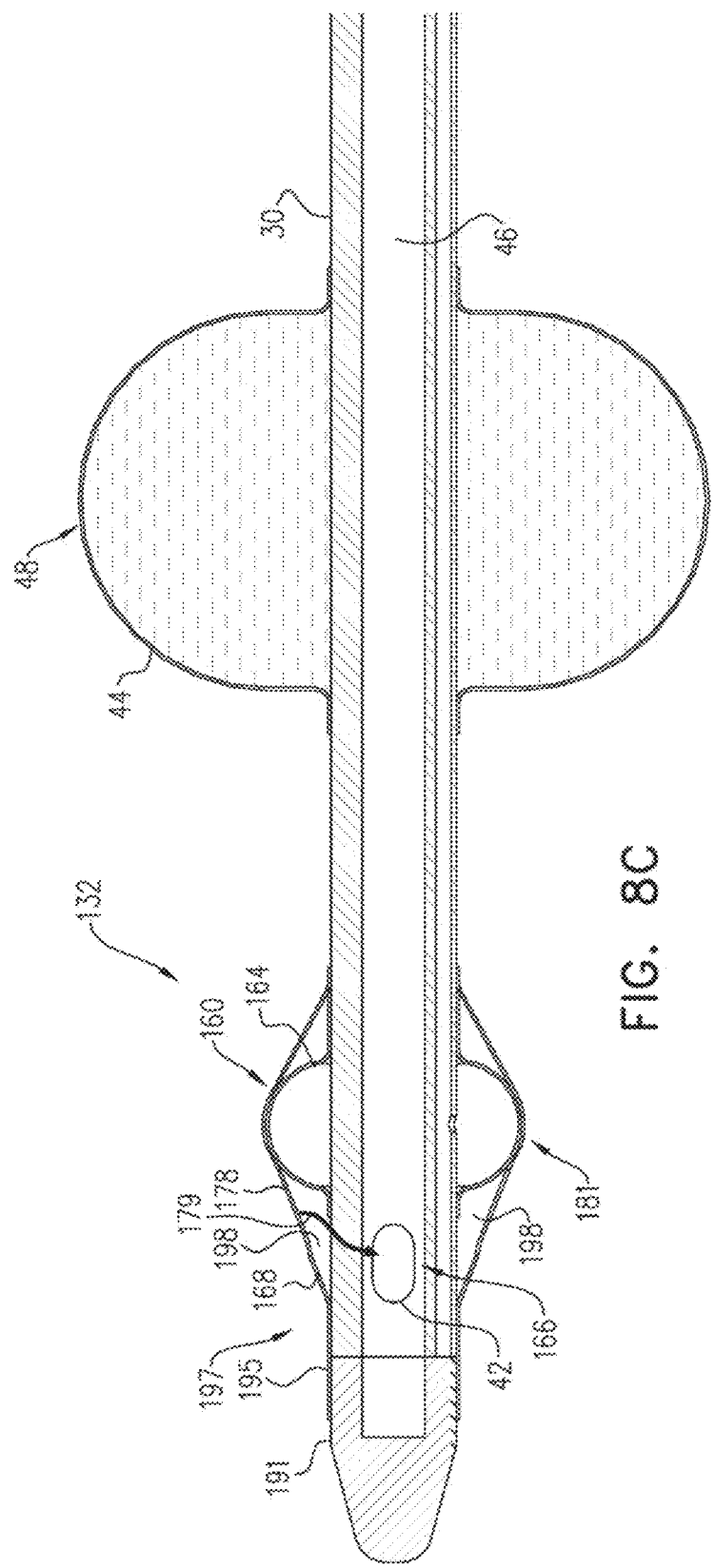

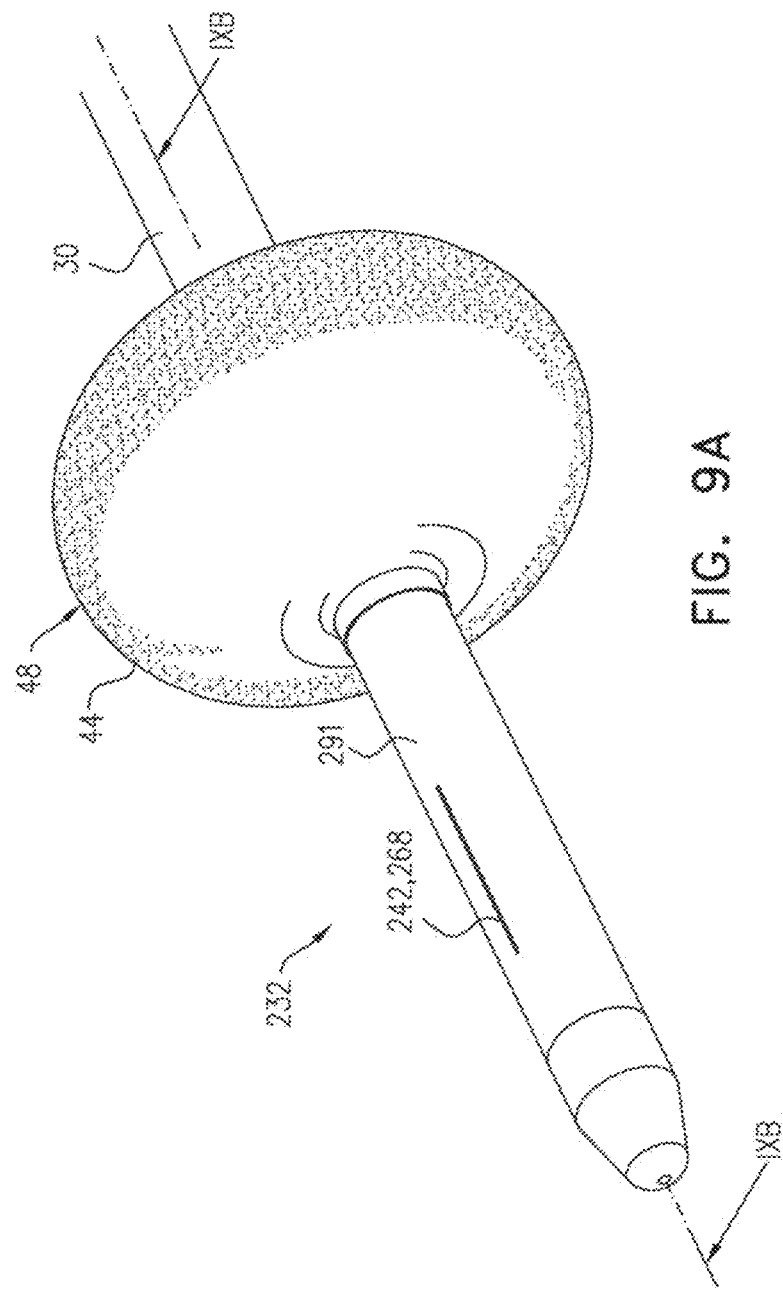

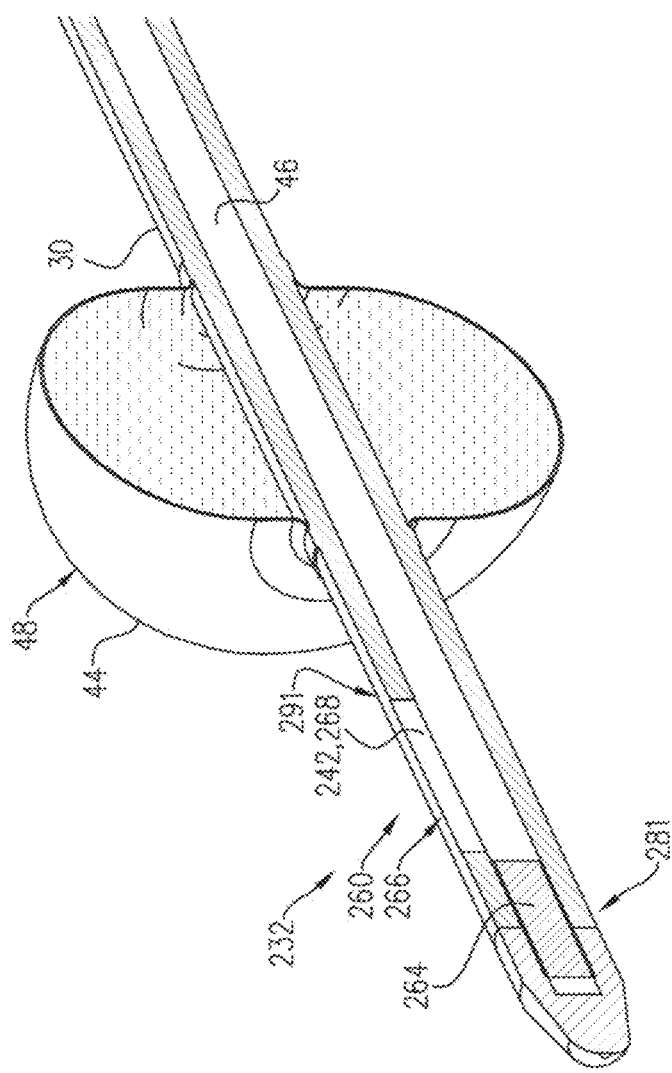

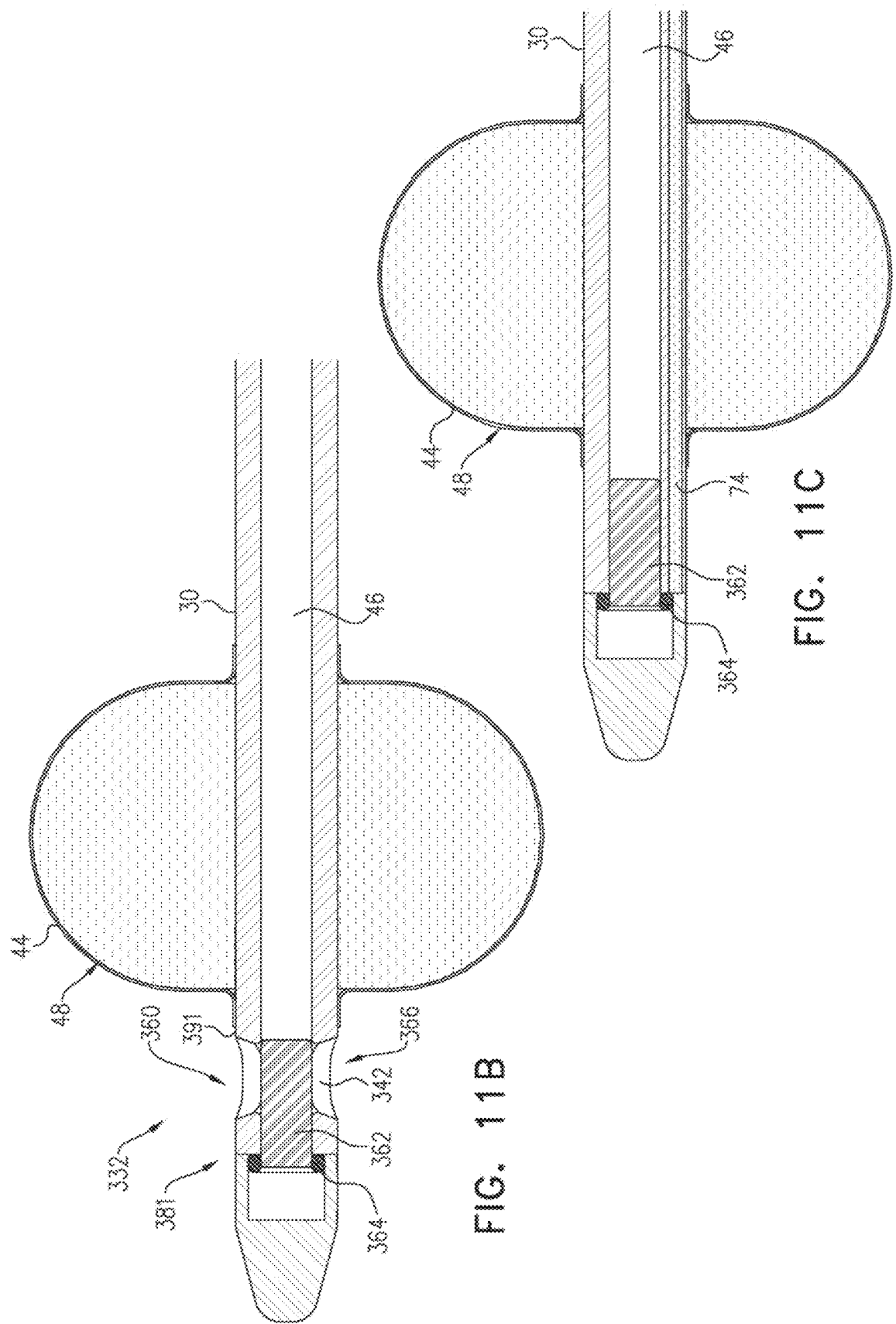

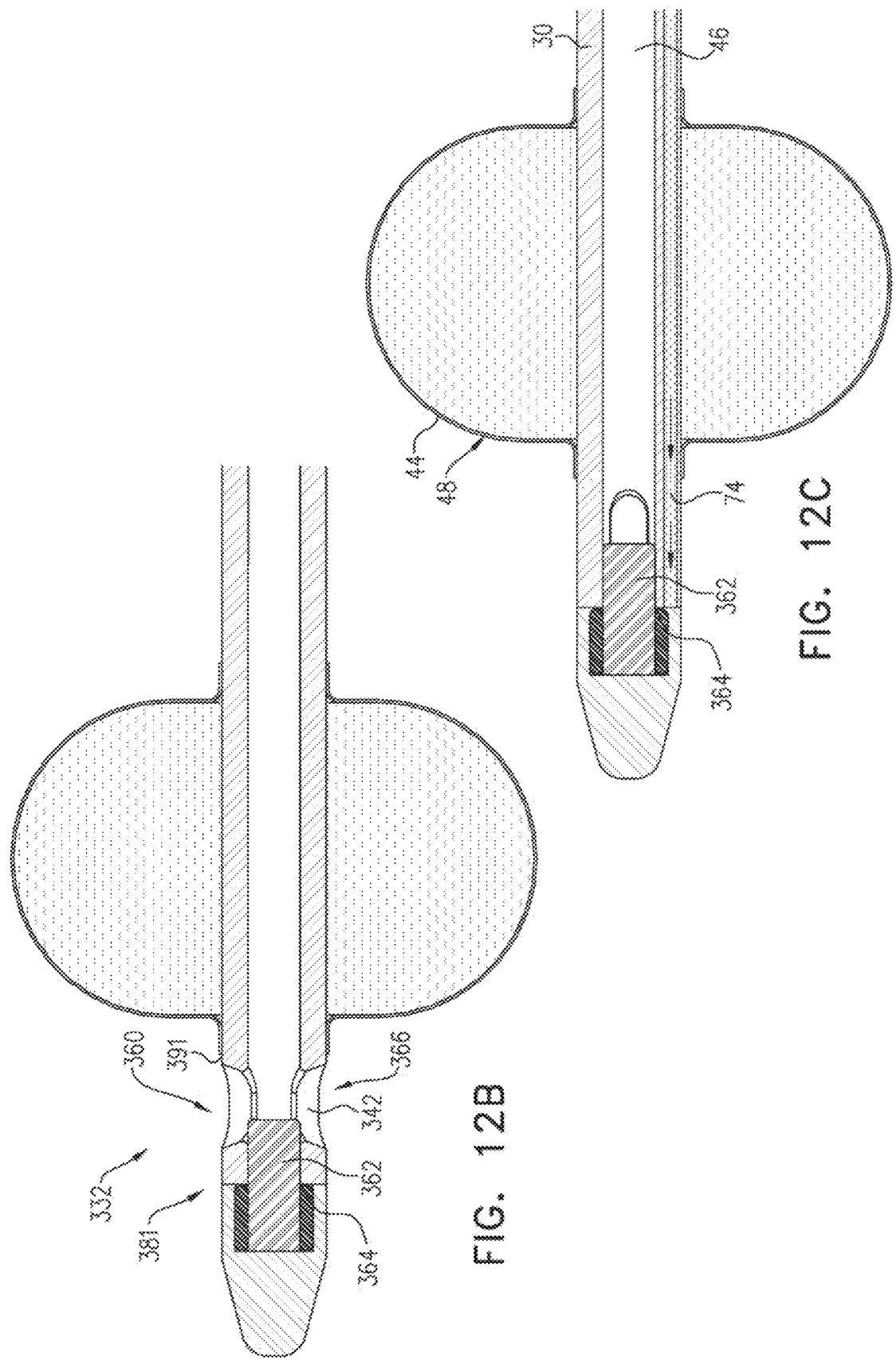

URINARY CATHETER PROSTHESES

CROSS-REFERENCE TO RELATED APPLICATIONS

The present patent application is the U.S. national stage of International Application PCT/IL2021/050085, filed Jan. 26, 2021, which claims priority from U.S. Provisional Application 62/995,470, filed Jan. 30, 2020, and U.S. Provisional Application 63/040,565, filed Jun. 18, 2020, both of which are assigned to the assignee of the present application. All applications are incorporated herein by reference.

FIELD OF THE APPLICATION

The present invention relates generally to prosthetic urethral valves for controlling urination.

BACKGROUND OF THE APPLICATION

Some people cannot urinate because of nerve injuries, diseases, muscle problems, or nerve problems. In general, while some people suffer from urine incontinence (the ability to hold urination), in general there are two broad types of urinary control conditions: failure to void and failure to store.

In failure to void (also known as urinary retention), there is difficulty emptying the bladder, i.e., urination is difficult. Failure to void may be caused by either an underactive bladder (i.e., a bladder that does not contract during the need to empty the bladder), nerve problems, or by an outlet obstruction, which is caused in the majority of cases by an enlarged prostate in men. Conventional techniques for treating underactive bladder include intermittent catheterization or an indwelling catheter, which is associated with medical complications (hematuria, pain, discomfort, urinary tract infections, and sepsis), and results in a substantial decrease in quality of life.

In failure to store, known as urinary incontinence, the bladder has difficulty functioning and serving as a reservoir. This condition has two main causes. One cause is an overactive bladder, in which case the incontinence occurs when the bladder contracts involuntarily and urine is expelled. The clinical expression is urgency, frequency, and nocturia, as well as incontinence (urge incontinence). The other cause is a weak sphincter that is incapable of withstanding or resisting pressures coming from the bladder (usually created by high abdominal pressures (stress incontinence)).

Most commercially-available urethral valves for treating failure to store include an inflatable cuff around the outside of the urethra, or a catheter that extends beyond the distal end of the urethra. The former type of urethral valve requires surgery for installation, and the latter type is non-cosmetic and invites infection. Also, most of the commercially-available urethral valve devices must be operated externally and depend on manual intervention. Devices that include an external valve, which in some cases is connected to a urine bag for enabling urination by opening the valve in the toilet, suffer from inconvenience, and more importantly, may result in from urinary tract infections (UTIs) due to their opening to the external environment, such as the user's underwear.

SUMMARY OF THE APPLICATION

In some embodiments of the present invention, a user-controllable urinary catheter prosthesis is provided for minimally-invasive insertion into a subject, similar in some respects to an indwelling catheter, intermittent catheter, or balloon catheter, such as a Foley catheter or an umbrella bladder holding catheter. The urinary catheter prosthesis comprises a proximal intra-urethral assembly, which is configured to be disposed entirely within a urethra of the subject by insertion via a meatus of the subject. The proximal intra-urethral assembly comprises a flexible intra-urethral catheter, which is shaped so as to define a urinary outlet at a proximal end of the flexible intra-urethral catheter; and a user-activatable hydraulic activator, which is disposed along the flexible intra-urethral catheter. The urinary catheter prosthesis further comprises a distal bladder assembly, which (a) extends distally from a distal end of the flexible intra-urethral catheter, and (b) is configured to be disposed, by insertion via the urethra, in a bladder of the subject. The urinary catheter prosthesis is shaped so as to define a lumen that defines a urine path between the distal bladder assembly and the urinary outlet.

The urinary catheter prosthesis further comprises a bladder anchor, which is coupled to the distal bladder assembly, and is configured to engage an inner surface of a wall of the bladder when in a deployed configuration, so as to anchor the urinary catheter prosthesis in place.

The urinary catheter prosthesis further comprises a hydraulic valve, which is disposed distal to the hydraulic activator, and which is configured to assume (a) an open state, in which the hydraulic valve allows urine flow between the distal bladder assembly and the urinary outlet, and (b) a closed resting state, in which the hydraulic valve entirely blocks urine from entering the distal bladder assembly, flowing through the lumen, and exiting the urinary outlet. The hydraulic activator is configured to transition the hydraulic valve from the closed resting state to the open state upon application of pressure to the hydraulic activator.

For some applications, the bladder anchor comprises an anchor balloon, which is configured to engage the bladder wall around the bladder neck when the anchor balloon is in an inflated deployed configuration.

Unlike conventional intermittent catheters or Foley catheters, which must be inserted into and removed from the urethra and bladder several times each day for treating urinary retention, the user-controllable urinary catheter prosthesis of the present invention can generally be left inserted in the urethra and bladder for an extended period of time, such as between one week and several months, without causing an unacceptable risk of urinary tract infections.

The user-controllable urinary catheter prosthesis of the present invention typically closely simulates natural physiologic function, and may optionally be adapted to each user according to his or her personal physiological parameters.

The urinary catheter prosthesis may be used to treat failure to void (i.e., urinary retention), including underactive bladder (including atonic bladder, hypotonic bladder, areflexic bladder, and a contractile bladder (AcB)), urinary retention, and high urinary residuals, as well as cases of outlet obstruction unresponsive to medical treatment or in high-risk patients for surgery or patients that cannot or do not wish to undergo surgery to remove the obstruction.

For some applications in which the bladder anchor comprises the anchor balloon, the urinary catheter prosthesis may also be used to treat failure to store (i.e., urinary incontinence), because the anchor balloon blocks the exit of urine from the bladder and thus serves as a plug, in addition to an anchor. In particular, the urinary catheter prosthesis may be used to treat overflow incontinence, male stress incontinence and male urge incontinence, particularly in combination with medications that relax the bladder.

There is therefore provided, in accordance with an Inventive Concept 1 of the present application, a user-controllable urinary catheter prosthesis for minimally-invasive insertion into a subject, the urinary catheter prosthesis including:
- a proximal intra-urethral assembly, which is (a) configured to be disposed entirely within a urethra of the subject by insertion via a meatus of the subject, and (b) includes:
  - a flexible intra-urethral catheter, which is shaped so as to define a urinary outlet at a proximal end of the flexible intra-urethral catheter; and
  - a user-activatable hydraulic activator, which is disposed along the flexible intra-urethral catheter;
- a distal bladder assembly, which (a) extends distally from a distal end of the flexible intra-urethral catheter, and (b) is configured to be disposed, by insertion via the urethra, in a bladder of the subject, wherein the urinary catheter prosthesis is shaped so as to define a lumen that defines a urine path between the distal bladder assembly and the urinary outlet;
- a bladder anchor, which is coupled to the distal bladder assembly, and is configured to engage an inner surface of a wall of the bladder when in a deployed configuration, so as to anchor the urinary catheter prosthesis in place; and
- a hydraulic valve, which is disposed distal to the hydraulic activator, and which is configured to assume:
  - (a) an open state, in which the hydraulic valve allows urine flow between the distal bladder assembly and the urinary outlet, and
  - (b) a closed resting state, in which the hydraulic valve entirely blocks urine from entering the distal bladder assembly, flowing through the lumen, and exiting the urinary outlet, wherein the hydraulic activator is configured to transition the hydraulic valve from the closed resting state to the open state upon application of pressure to the hydraulic activator.

Inventive Concept 2. The urinary catheter prosthesis according to Inventive Concept 1, wherein at least a portion of the hydraulic valve is part of the distal bladder assembly.

Inventive Concept 3. The urinary catheter prosthesis according to Inventive Concept 2, wherein the distal bladder assembly includes the hydraulic valve.

Inventive Concept 4. The urinary catheter prosthesis according to Inventive Concept 1, wherein the hydraulic valve is disposed in the urinary catheter prosthesis distal to the hydraulic activator.

Inventive Concept 5. The urinary catheter prosthesis according to Inventive Concept 1, wherein the distal bladder assembly (a) is shaped so as to define a urinary inlet, and (b) is configured to be disposed, by insertion via the urethra, in the bladder of the subject such that the urinary inlet is disposed in the bladder of the subject, wherein the lumen of the urinary catheter prosthesis defines the urine path between the urinary inlet and the urinary outlet.

Inventive Concept 6. The urinary catheter prosthesis according to Inventive Concept 5, wherein the hydraulic valve is configured such that (a) when in the open state, the hydraulic valve allows urine flow between the urinary inlet and the urinary outlet, and (b) when in the closed resting state, the hydraulic valve entirely blocks urine from entering the urinary inlet, flowing through the lumen, and exiting the urinary outlet.

Inventive Concept 7. The urinary catheter prosthesis according to any one of Inventive Concepts 1-3,
wherein the hydraulic valve includes a valve balloon and a urinary inlet, wherein the distal bladder assembly is configured to be disposed, by insertion via the urethra, in the bladder of the subject such that the urinary inlet is disposed in the bladder of the subject, wherein the lumen of the urinary catheter prosthesis defines the urine path between the urinary inlet and the urinary outlet, wherein the hydraulic valve is configured to assume the open state upon inflation of the valve balloon, wherein the hydraulic valve is configured such that the urinary inlet is closed when the hydraulic valve is in the closed resting state, and wherein the hydraulic valve is configured to assume the open state when the valve balloon is inflated sufficiently to open the urinary inlet.

Inventive Concept 8. The urinary catheter prosthesis according to Inventive Concept 7,
wherein the urinary inlet is shaped so as to define one or more slits that are closed when the hydraulic valve is in the closed resting state, and wherein the hydraulic valve is configured to assume the open state when the valve balloon is inflated sufficiently to push open the one or more slits.

Inventive Concept 9. The urinary catheter prosthesis according to Inventive Concept 8, wherein a distal portion of distal bladder assembly includes a flexible tubular casing that is shaped so as to define therethrough the one or more slits of the urinary inlet.

Inventive Concept 10. The urinary catheter prosthesis according to Inventive Concept 8, wherein the valve balloon and the one or more slits are located at respective axial positions along the distal bladder assembly, the axial positions at least partially non-axially-overlapping with each other.

Inventive Concept 11. The urinary catheter prosthesis according to Inventive Concept 8, wherein the valve balloon, when inflated, is shaped generally as an oblate spheroid lacking a section on one side.

Inventive Concept 12. The urinary catheter prosthesis according to any one of Inventive Concepts 1-3,
wherein a distal portion of the distal bladder assembly includes a tubular casing, which is shaped so as to define a urinary inlet through the tubular casing at an axial position along the tubular casing, wherein the distal bladder assembly is configured to be disposed, by insertion via the urethra, in the bladder of the subject such that the urinary inlet is disposed in the bladder of the subject, wherein the lumen of the urinary catheter prosthesis defines the urine path between the urinary inlet and the urinary outlet, wherein the hydraulic valve further includes an elastic sleeve, which (a) defines one or more openings through the elastic sleeve, (b) is sealingly coupled to the tubular casing, and (c) surrounds the tubular casing, including at the axial position of the urinary inlet, wherein the hydraulic valve is configured such that when it is in the closed resting state, the elastic sleeve entirely occludes the urinary inlet, and wherein the hydraulic valve is configured to assume the open state when the valve balloon is inflated sufficiently to radially expand the elastic sleeve such that the elastic sleeve (a) does not occlude the urinary inlet and (b) defines a fluid flow path between (i) the one or more openings through the elastic sleeve and (ii) the urinary inlet.

Inventive Concept 13. The urinary catheter prosthesis according to Inventive Concept 12, wherein an axial position of the valve balloon along the distal bladder assembly is at least partially non-axially-overlapping with the axial position of the urinary inlet.

Inventive Concept 14. The urinary catheter prosthesis according to Inventive Concept 12, wherein the one or more openings through the elastic sleeve are located at respective radial positions around the tubular casing that are entirely non-radially-overlapping with a radial position of the urinary inlet around the tubular casing.

There is further provided, in accordance with an Inventive Concept 15 of the present application, a user-controllable urinary catheter prosthesis for minimally-invasive insertion into a subject, the urinary catheter prosthesis including:
- a proximal intra-urethral assembly, which is (a) configured to be disposed entirely within a urethra of the subject by insertion via a meatus of the subject, and (b) includes:
  - a flexible intra-urethral catheter, which is shaped so as to define a urinary outlet at a proximal end of the flexible intra-urethral catheter; and
  - a user-activatable hydraulic activator, which is disposed along the flexible intra-urethral catheter;
- a distal bladder assembly, which (a) extends distally from a distal end of the flexible intra-urethral catheter, (b) is shaped so as to define a urinary inlet, and (c) is configured to be disposed, by insertion via the urethra, in a bladder of the subject such that the urinary inlet is disposed in the bladder of the subject, wherein the urinary catheter prosthesis is shaped so as to define a lumen that defines a urine path between the urinary inlet and the urinary outlet;
- a bladder anchor, which is coupled to the distal bladder assembly, and is configured to engage an inner surface of a wall of the bladder when in a deployed configuration, so as to anchor the urinary catheter prosthesis in place; and
- a hydraulic valve, which is disposed in the urinary catheter prosthesis distal to the hydraulic activator, and which is configured to assume:
  - (a) an open state, in which the hydraulic valve allows urine flow between the urinary inlet and the urinary outlet, and
  - (b) a closed resting state, in which the hydraulic valve entirely blocks urine from entering the urinary inlet, flowing through the lumen, and exiting the urinary outlet, wherein the hydraulic activator is configured to transition the hydraulic valve from the closed resting state to the open state upon application of pressure to the hydraulic activator.

Inventive Concept 16. The urinary catheter prosthesis according to any one of Inventive Concepts 4 and 15, wherein the hydraulic valve is disposed at least partially in the distal bladder assembly.

Inventive Concept 17. The urinary catheter prosthesis according to Inventive Concept 16, wherein the hydraulic valve is disposed entirely in the distal bladder assembly.

Inventive Concept 18. The urinary catheter prosthesis according to any one of Inventive Concepts 6 and 15, wherein the hydraulic valve is configured, when in the closed resting state, to occlude the urinary inlet, and, when in the open state, not to occlude the urinary inlet.

Inventive Concept 19. The urinary catheter prosthesis according to any one of Inventive Concepts 1 and 15, wherein the flexible intra-urethral catheter is more flexible than the distal bladder assembly.

Inventive Concept 20. The urinary catheter prosthesis according to any one of Inventive Concepts 1 and 15, wherein at least a portion of the distal bladder assembly is disposed distal to the bladder anchor at least when the bladder anchor is in the deployed configuration.

Inventive Concept 21. The urinary catheter prosthesis according to any one of Inventive Concepts 5 and 15, wherein at least a portion of the distal bladder assembly is disposed distal to the bladder anchor at least when the bladder anchor is in the deployed configuration, and wherein the urinary inlet is disposed distal to the bladder anchor at least when the bladder anchor is in the deployed configuration.

Inventive Concept 22. The urinary catheter prosthesis according to any one of Inventive Concepts 1 and 15, wherein the hydraulic valve includes a piston.

Inventive Concept 23. The urinary catheter prosthesis according to any one of Inventive Concepts 1 and 15, wherein a length of the proximal intra-urethral assembly is between 3 and 30 cm, measured along the proximal intra-urethral assembly.

Inventive Concept 24. The urinary catheter prosthesis according to any one of Inventive Concepts 1 and 15, wherein a greatest outer diameter of the flexible intra-urethral catheter is at least 5 mm.

Inventive Concept 25. The urinary catheter prosthesis according to any one of Inventive Concepts 1 and 15, wherein a greatest outer diameter of the flexible intra-urethral catheter is no more than 10 mm.

Inventive Concept 26. The urinary catheter prosthesis according to any one of Inventive Concepts 1 and 15, wherein a greatest outer diameter of the distal bladder assembly is at least 5 mm when the bladder anchor is in a non-radially-expanded deployment configuration.

Inventive Concept 27. The urinary catheter prosthesis according to any one of Inventive Concepts 1 and 15, wherein a greatest outer diameter of the distal bladder assembly is no more than 10 mm when the bladder anchor is in a non-radially-expanded deployment configuration.

Inventive Concept 28. The urinary catheter prosthesis according to any one of Inventive Concepts 1-27,
  wherein the hydraulic valve includes a valve balloon, and
  wherein the hydraulic valve is configured to assume the open state upon inflation of the valve balloon.

Inventive Concept 29. The urinary catheter prosthesis according to Inventive Concept 28,
  wherein the hydraulic activator includes a control balloon,
  wherein the urinary catheter prosthesis further includes a hydraulic tube, which couples the control balloon in hydraulic communication with the valve balloon, and
  wherein the control balloon is configured, upon squeezing thereof, to inflate the valve balloon, thereby transitioning the hydraulic valve from the closed resting state to the open state.

Inventive Concept 30. The urinary catheter prosthesis according to any one of Inventive Concepts 15-27,
  wherein the hydraulic valve includes a valve balloon,
  wherein the hydraulic valve is configured to assume the open state upon inflation of the valve balloon,
  wherein the distal bladder assembly is configured such that the urinary inlet is closed when the hydraulic valve is in the closed resting state, and
  wherein the hydraulic valve is configured to assume the open state when the valve balloon is inflated sufficiently to open the urinary inlet.

Inventive Concept 31. The urinary catheter prosthesis according to Inventive Concept 30,
  wherein the urinary inlet is shaped so as to define one or more slits that are closed when the hydraulic valve is in the closed resting state, and wherein the hydraulic valve is configured to assume the open state when the valve balloon is inflated sufficiently to push open the one or more slits.

Inventive Concept 32. The urinary catheter prosthesis according to Inventive Concept 31, wherein a distal portion of distal bladder assembly includes a flexible tubular casing that is shaped so as to define therethrough the one or more slits of the urinary inlet.

Inventive Concept 33. The urinary catheter prosthesis according to Inventive Concept 31, wherein the valve balloon and the one or more slits are located at respective axial positions along the distal bladder assembly, the axial positions at least partially non-axially-overlapping with each other.

Inventive Concept 34. The urinary catheter prosthesis according to Inventive Concept 31, wherein the valve balloon, when inflated, is shaped generally as an oblate spheroid lacking a section on one side.

Inventive Concept 35. The urinary catheter prosthesis according to any one of Inventive Concepts 15-27,
wherein the hydraulic valve includes a valve balloon,
wherein the hydraulic valve is configured to assume the open state upon inflation of the valve balloon,
wherein a distal portion of the distal bladder assembly includes a tubular casing, which is shaped so as to define the urinary inlet through the tubular casing at an axial position along the tubular casing,
wherein the hydraulic valve further includes an elastic sleeve, which (a) defines one or more openings through the elastic sleeve, (b) is sealingly coupled to the tubular casing, and (c) surrounds the tubular casing, including at the axial position of the urinary inlet,
wherein the hydraulic valve is configured such that when it is in the closed resting state, the elastic sleeve entirely occludes the urinary inlet, and
wherein the hydraulic valve is configured to assume the open state when the valve balloon is inflated sufficiently to radially expand the elastic sleeve such that the elastic sleeve (a) does not occlude the urinary inlet and (b) defines a fluid flow path between (i) the one or more openings through the elastic sleeve and (ii) the urinary inlet.

Inventive Concept 36. The urinary catheter prosthesis according to Inventive Concept 35, wherein an axial position of the valve balloon along the distal bladder assembly is at least partially non-axially-overlapping with the axial position of the urinary inlet.

Inventive Concept 37. The urinary catheter prosthesis according to Inventive Concept 35, wherein the one or more openings through the elastic sleeve are located at respective radial positions around the tubular casing that are entirely non-radially-overlapping with a radial position of the urinary inlet around the tubular casing.

Inventive Concept 38. The urinary catheter prosthesis according to any one of Inventive Concepts 5 and 15-27,
wherein the hydraulic valve includes a valve balloon,
wherein the hydraulic valve is configured to assume the open state upon inflation of the valve balloon,
wherein the hydraulic valve further includes a valve plug, which is attached to the valve balloon, and which is configured to occlude the urinary inlet when the hydraulic valve is in the closed resting state, and
wherein the hydraulic valve is configured such that the inflation of the valve balloon moves the valve plug away from the urinary inlet, thereby transitioning the hydraulic valve to the open state.

Inventive Concept 39. The urinary catheter prosthesis according to Inventive Concept 38, wherein the hydraulic valve is configured such that the inflation of the valve balloon moves the valve plug in a distal direction away from the urinary inlet, thereby transitioning the hydraulic valve to the open state.

Inventive Concept 40. The urinary catheter prosthesis according to any one of Inventive Concepts 1-27, wherein the hydraulic valve is configured to remain in the open state even after cessation of the application of the pressure to the hydraulic activator.

Inventive Concept 41. The urinary catheter prosthesis according to Inventive Concept 40, wherein the hydraulic valve is configured, after remaining in the open state even after the cessation of the application of the pressure to the hydraulic activator, to automatically transition to the closed resting state such that the hydraulic valve assumes the closed resting state a set amount of time after being transitioned to the open state.

Inventive Concept 42. The urinary catheter prosthesis according to Inventive Concept 41, wherein the set amount of time has a value that falls in a range of 15 to 360 seconds.

Inventive Concept 43. The urinary catheter prosthesis according to Inventive Concept 42, wherein the set amount of time has a value that falls in a range of 20 to 360 seconds.

Inventive Concept 44. The urinary catheter prosthesis according to Inventive Concept 41, wherein the open state includes an entirely-open sub-state and a partially-open sub-state, and wherein the hydraulic valve is configured to:
assume the entirely-open sub-state immediately upon being transitioned to the open state,
thereafter, automatically transition to the partially-open sub-state, and
thereafter, automatically transition to the closed resting state the set amount of time after being transitioned to the entirely-open sub-state.

Inventive Concept 45. The urinary catheter prosthesis according to Inventive Concept 41, wherein the hydraulic valve further includes a spring, which is configured to store elastic energy during transitioning of the hydraulic valve from the closed resting state to the open state, and to automatically transition the hydraulic valve to the closed resting state by releasing the elastic energy.

Inventive Concept 46. The urinary catheter prosthesis according to Inventive Concept 45,
wherein the urinary catheter prosthesis includes hydraulic liquid, and the hydraulic valve includes a piston,
wherein the hydraulic activator is configured to transition the hydraulic valve from the closed resting state to the open state by transferring at least a portion of the hydraulic liquid from the hydraulic activator to the hydraulic valve, and
wherein the urinary catheter prosthesis further includes a hydraulic one-way shutter that is configured to delay return of the hydraulic liquid from the hydraulic valve to the hydraulic activator, thereby delaying the piston from automatically transitioning from the open state to the closed resting state, such that the hydraulic valve assumes the closed resting state the set amount of time after being transitioned to the open state.

Inventive Concept 47. The urinary catheter prosthesis according to Inventive Concept 45, wherein the hydraulic valve includes a piston, and wherein the spring is configured to move the piston while releasing the elastic energy.

Inventive Concept 48. The urinary catheter prosthesis according to Inventive Concept 41, wherein the hydraulic valve further includes an elastic valve balloon, which is configured to store elastic energy during transitioning of the hydraulic valve from the closed resting state to the open state upon inflation of the elastic valve balloon, and to automatically transition the hydraulic valve to the closed resting state by releasing the elastic energy as the elastic valve balloon deflates.

Inventive Concept 49. The urinary catheter prosthesis according to Inventive Concept 48,
wherein the urinary catheter prosthesis includes hydraulic liquid,
wherein the hydraulic activator is configured to transition the hydraulic valve from the closed resting state to the open state by transferring at least a portion of the hydraulic liquid from the hydraulic activator to the elastic valve balloon, and
wherein the urinary catheter prosthesis further includes a hydraulic one-way shutter that is configured to delay return of the hydraulic liquid from the elastic valve balloon to the hydraulic activator, thereby delaying the elastic valve balloon from automatically transitioning from the open state to the closed resting state, such that the hydraulic valve assumes the closed resting state the set amount of time after being transitioned to the open state.

Inventive Concept 50. The urinary catheter prosthesis according to any one of Inventive Concepts 1-27, wherein the hydraulic activator at least partially surrounds the lumen at an axial location along the flexible intra-urethral catheter.

Inventive Concept 51. The urinary catheter prosthesis according to Inventive Concept 50, wherein the hydraulic activator surrounds at least 180 degrees of the lumen at the axial location.

Inventive Concept 52. The urinary catheter prosthesis according to Inventive Concept 51, wherein the hydraulic activator completely surrounds the lumen at the axial location.

Inventive Concept 53. The urinary catheter prosthesis according to any one of Inventive Concepts 1-27, wherein the urinary catheter prosthesis is configured to be minimally-invasive inserted into a male subject.

Inventive Concept 54. The urinary catheter prosthesis according to Inventive Concept 53, wherein the hydraulic activator is disposed at least 20 cm from the hydraulic valve, measured along the urinary catheter prosthesis.

Inventive Concept 55. The urinary catheter prosthesis according to Inventive Concept 53, wherein a length of the proximal intra-urethral assembly is between 7 and 30 cm, measured along the proximal intra-urethral assembly.

Inventive Concept 56. The urinary catheter prosthesis according to any one of Inventive Concepts 1-27, wherein the urinary catheter prosthesis is configured to be minimally-invasive inserted into a female subject.

Inventive Concept 57. The urinary catheter prosthesis according to Inventive Concept 56, wherein the hydraulic activator is disposed at least 7 cm from the hydraulic valve, measured along the urinary catheter prosthesis.

Inventive Concept 58. The urinary catheter prosthesis according to Inventive Concept 56, wherein a length of the proximal intra-urethral assembly is between 3 and 10 cm, measured along the proximal intra-urethral assembly.

Inventive Concept 59. The urinary catheter prosthesis according to any one of Inventive Concepts 1-27, wherein the bladder anchor includes an anchor balloon, which is configured to engage the bladder wall around a bladder neck when the anchor balloon is in an inflated deployed configuration.

Inventive Concept 60. The urinary catheter prosthesis according to Inventive Concept 59, wherein the bladder anchor further includes:
an anchor-balloon plug, which seals the anchor balloon when in a sealed state; and
a plug-release line, which has a proximal end that is disposed proximally beyond the proximal end of the flexible intra-urethral catheter, and a distal portion that is connected to the anchor-balloon plug,
wherein the bladder anchor is configured such that proximal pulling on the plug-release line transitions the anchor-balloon plug from the sealed state to an open state, in which the anchor-balloon plug does not seal the anchor balloon.

Inventive Concept 61. The urinary catheter prosthesis according to Inventive Concept 60, further including:
a filling channel, which runs along a portion of the flexible intra-urethral catheter and has a distal end portion in fluid communication with an interior of the anchor balloon; and
a filling tube, which is removably coupled in fluid communication with a proximal end portion of the filling channel.

Inventive Concept 62. The urinary catheter prosthesis according to Inventive Concept 61, wherein the plug-release line passes through a lumen of the filling tube when the filling tube is removably coupled in the fluid communication with a proximal end portion of the filling channel.

Inventive Concept 63. The urinary catheter prosthesis according to Inventive Concept 61,
wherein the hydraulic activator includes:
a control balloon, which is configured, upon squeezing thereof, to transition the hydraulic valve from the closed resting state to the open state; and
a tubular counterforce surface against which the control balloon presses upon application of the pressure, wherein the counterforce surface is more rigid than the flexible intra-urethral catheter,
wherein tubular counterforce surface is shaped so as to define a lateral opening, and
wherein the filling tube passes through the lateral opening when the filling tube is removably coupled in the fluid communication with the proximal end portion of the filling channel.

Inventive Concept 64. The urinary catheter prosthesis according to Inventive Concept 60, wherein the urinary catheter prosthesis is configured to be disposed entirely within a body of the subject, except for a portion of the plug-release line.

Inventive Concept 65. The urinary catheter prosthesis according to any one of Inventive Concepts 5 and 15-27,
wherein the bladder anchor includes an anchor balloon, which is configured to engage the bladder wall around a bladder neck when the anchor balloon is in an inflated deployed configuration, and
wherein the urinary inlet is disposed distal to the anchor balloon.

Inventive Concept 66. The urinary catheter prosthesis according to any one of Inventive Concepts 1-27, wherein the bladder anchor includes an umbrella anchor, which includes a plurality of ribs that are configured to engage the bladder wall around a bladder neck when the umbrella anchor is in the deployed configuration.

Inventive Concept 67. The urinary catheter prosthesis according to any one of Inventive Concepts 1-27, wherein the bladder anchor includes a plurality of flexible petals that are configured to engage the bladder wall around a bladder neck when the bladder anchor is in the deployed configuration.

Inventive Concept 68. The urinary catheter prosthesis according to any one of Inventive Concepts 1-27, wherein the hydraulic activator includes a control balloon, which is configured, upon squeezing thereof, to transition the hydraulic valve from the closed resting state to the open state.

Inventive Concept 69. The urinary catheter prosthesis according to Inventive Concept 68, further including a hydraulic tube, which couples the control balloon in hydraulic communication with the hydraulic valve such that the hydraulic valve transitions from the closed resting state to the open state upon the squeezing of the control balloon.

Inventive Concept 70. The urinary catheter prosthesis according to Inventive Concept 69, wherein the hydraulic valve includes a piston, and wherein the hydraulic tube couples the control balloon in the hydraulic communication with the piston.

Inventive Concept 71. The urinary catheter prosthesis according to Inventive Concept 69,
 wherein the hydraulic valve includes a valve balloon,
 wherein the hydraulic valve is configured to assume the open state upon inflation of the valve balloon, and
 wherein the hydraulic tube couples the control balloon in the hydraulic communication with the valve balloon.

Inventive Concept 72. The urinary catheter prosthesis according to Inventive Concept 69, wherein the hydraulic activator is configured to transition the hydraulic valve from the closed resting state to the open state upon the application of the pressure having a minimum threshold value.

Inventive Concept 73. The urinary catheter prosthesis according to Inventive Concept 69, wherein the hydraulic activator is configured to transition the hydraulic valve from the closed resting state to the open state upon the application of the pressure at a minimum threshold rate of change.

Inventive Concept 74. The urinary catheter prosthesis according to Inventive Concept 73, wherein the hydraulic activator is configured to transition the hydraulic valve from the closed resting state to the open state upon the application of the pressure at between the minimum threshold rate of change and a maximum threshold rate of change.

Inventive Concept 75. The urinary catheter prosthesis according to Inventive Concept 68, wherein the hydraulic activator includes a counterforce surface against which the control balloon presses upon application of the pressure, and wherein the counterforce surface is more rigid than the flexible intra-urethral catheter.

Inventive Concept 76. The urinary catheter prosthesis according to Inventive Concept 75, wherein the counterforce surface is shaped as a tube.

Inventive Concept 77. The urinary catheter prosthesis according to Inventive Concept 68, wherein the control balloon at least partially surrounds the lumen at an axial location along the flexible intra-urethral catheter.

Inventive Concept 78. The urinary catheter prosthesis according to Inventive Concept 77, wherein the control balloon completely surrounds the lumen at the axial location.

Inventive Concept 79. The urinary catheter prosthesis according to any one of Inventive Concepts 1-27, wherein the hydraulic activator is configured to transition the hydraulic valve from the closed resting state to the open state upon the application of the pressure having a minimum threshold value.

Inventive Concept 80. The urinary catheter prosthesis according to any one of Inventive Concepts 1-27, wherein the hydraulic activator is configured to transition the hydraulic valve from the closed resting state to the open state upon the application of the pressure at a minimum threshold rate of change.

Inventive Concept 81. The urinary catheter prosthesis according to Inventive Concept 80, wherein the hydraulic activator is configured to transition the hydraulic valve from the closed resting state to the open state upon the application of the pressure at between the minimum threshold rate of change and a maximum threshold rate of change.

Inventive Concept 82. The urinary catheter prosthesis according to any one of Inventive Concepts 1-27, wherein the urinary catheter prosthesis does not include any electrical components.

Inventive Concept 83. The urinary catheter prosthesis according to any one of Inventive Concepts 1-27, wherein the urinary catheter prosthesis does not include any circuitry.

Inventive Concept 84. The urinary catheter prosthesis according to any one of Inventive Concepts 1-27, wherein the urinary catheter prosthesis does not include a battery.

Inventive Concept 85. The urinary catheter prosthesis according to any one of Inventive Concepts 1-27, wherein the urinary catheter prosthesis is not configured to receive power, either over a wire or wirelessly.

Inventive Concept 86. The urinary catheter prosthesis according to any one of Inventive Concepts 1-27, wherein the urinary catheter prosthesis does not include any magnets.

Inventive Concept 87. The urinary catheter prosthesis according to any one of Inventive Concepts 1-27, wherein the flexible intra-urethral catheter includes a sensor that is configured to sense, either continuously or periodically, one or more parameters of urine flowing through the lumen of the urinary catheter prosthesis.

Inventive Concept 88. The urinary catheter prosthesis according to Inventive Concept 87, wherein the one or more parameters include one or more parameters selected from the group consisting of: a flow rate of the urine, a pressure of the urine, a temperature of the urine, and a pH level of the urine.

Inventive Concept 89. The urinary catheter prosthesis according to Inventive Concept 87, wherein the sensor extends entirely around the lumen.

Inventive Concept 90. The urinary catheter prosthesis according to Inventive Concept 87, wherein the sensor includes a wireless transmitter, which is configured to wirelessly transmit signals indicative of the one or more sensed parameters.

Inventive Concept 91. The urinary catheter prosthesis according to Inventive Concept 87, wherein the sensor includes a flexible printed circuit board, which is wrapped partially or entirely around the lumen.

Inventive Concept 92. The urinary catheter prosthesis according to Inventive Concept 87, wherein the sensor is passive.

Inventive Concept 93. The urinary catheter prosthesis according to Inventive Concept 87, wherein the sensor includes a resonance circuit.

There is still further provided, in accordance with an Inventive Concept 94 of the present application, a method including:
 minimally-invasively inserting a user-controllable urinary catheter prosthesis into a urethra of a subject via a meatus of the subject, while a bladder anchor of the urinary catheter prosthesis is in a non-radially-expanded deployment configuration;
 while the bladder anchor remains in the non-radially-expanded deployment configuration, distally advancing the urinary catheter prosthesis in the urethra until:
  the bladder anchor is disposed in a bladder of the subject,
  a distal bladder assembly of the urinary catheter prosthesis is disposed in the bladder of the subject, and
  a proximal intra-urethral assembly of the urinary catheter prosthesis is entirely disposed within the urethra, such that (a) a urinary outlet, at a proximal end of a flexible intra-urethral catheter of the proximal intra-urethral assembly, is positioned in the urethra, and (b) a user-activatable hydraulic activator, disposed along the flexible intra-urethral catheter, is positioned within the urethra; and after inserting and advancing the urinary catheter prosthesis, transitioning the bladder anchor to a deployed configuration in which the bladder anchor engages an inner surface of a wall of the bladder, so as to anchor the urinary catheter prosthesis in place, wherein the bladder anchor is coupled to the distal bladder assembly, the distal bladder assembly extends distally from a distal end of the flexible intra-urethral catheter, wherein the urinary catheter prosthesis is shaped so as to define a lumen that defines a urine path between the distal bladder assembly and the urinary outlet, and wherein the urinary catheter prosthesis further includes a hydraulic valve, which is configured to assume (a) an open state, in which the hydraulic valve allows urine flow between the distal bladder assembly and the urinary outlet, and (b) a closed resting state, in which the hydraulic valve entirely blocks urine from entering the distal bladder assembly, flowing through the lumen, and exiting the urinary outlet, and wherein the hydraulic activator is configured to transition the hydraulic valve from the closed resting state to the open state upon application of pressure to the hydraulic activator.

Inventive Concept 95. The method according to Inventive Concept 94, further including, after transitioning the bladder anchor to the deployed configuration, applying the pressure to the hydraulic activator from outside the urethra to transition the hydraulic valve from the closed resting state to the open state.

Inventive Concept 96. The method according to Inventive Concept 95, wherein the subject is male, and wherein applying the pressure to the hydraulic activator including applying pressure to an external surface of a penis of the male subject.

Inventive Concept 97. The method according to Inventive Concept 96, wherein applying the pressure to the external surface of the penis includes squeezing the penis.

Inventive Concept 98. The method according to Inventive Concept 95, wherein the subject is female, and wherein applying the pressure to the hydraulic activator including applying pressure, from within a vagina of the female subject, to a wall of the vagina.

Inventive Concept 99. The method according to Inventive Concept 94, wherein the hydraulic valve is configured to remain in the open state even after cessation of the application of the pressure to the hydraulic activator.

Inventive Concept 100. The method according to Inventive Concept 99, wherein the hydraulic valve is configured, after remaining in the open state even after the cessation of the application of the pressure to the hydraulic activator, to automatically transition to the closed resting state such that the hydraulic valve assumes the closed resting state a set amount of time after being transitioned to the open state.

Inventive Concept 101. The method according to Inventive Concept 100, wherein the set amount of time has a value that falls in a range of 15 to 360 seconds.

Inventive Concept 102. The method according to Inventive Concept 101, wherein the set amount of time has a value that falls in a range of 20 to 360 seconds.

Inventive Concept 103. The method according to Inventive Concept 100, wherein the open state includes an entirely-open sub-state and a partially-open sub-state, and wherein the hydraulic valve is configured to:

assume the entirely-open sub-state immediately upon being transitioned to the open state, thereafter, automatically transition to the partially-open sub-state, and thereafter, automatically transition to the closed resting state the set amount of time after being transitioned to the entirely-open sub-state.

Inventive Concept 104. The method according to Inventive Concept 100, wherein the hydraulic valve further includes a spring, which is configured to store elastic energy during transitioning of the hydraulic valve from the closed resting state to the open state, and to automatically transition the hydraulic valve to the closed resting state by releasing the elastic energy.

Inventive Concept 105. The method according to Inventive Concept 104, wherein the urinary catheter prosthesis includes hydraulic liquid, and the hydraulic valve includes a piston, wherein the hydraulic activator is configured to transition the hydraulic valve from the closed resting state to the open state by transferring at least a portion of the hydraulic liquid from the hydraulic activator to the hydraulic valve, and wherein the urinary catheter prosthesis further includes a hydraulic one-way shutter that is configured to delay return of the hydraulic liquid from the hydraulic valve to the hydraulic activator, thereby delaying the piston from automatically transitioning from the open state to the closed resting state, such that the hydraulic valve assumes the closed resting state the set amount of time after being transitioned to the open state.

Inventive Concept 106. The method according to Inventive Concept 104, wherein the hydraulic valve includes a piston, and wherein the spring is configured to move the piston while releasing the elastic energy.

Inventive Concept 107. The method according to Inventive Concept 100, wherein the hydraulic valve further includes an elastic valve balloon, which is configured to store elastic energy during transitioning of the hydraulic valve from the closed resting state to the open state upon inflation of the elastic valve balloon, and to automatically transition the hydraulic valve to the closed resting state by releasing the elastic energy as the elastic valve balloon deflates.

Inventive Concept 108. The method according to Inventive Concept 107, wherein the urinary catheter prosthesis includes hydraulic liquid, wherein the hydraulic activator is configured to transition the hydraulic valve from the closed resting state to the open state by transferring at least a portion of the hydraulic liquid from the hydraulic activator to the elastic valve balloon, and wherein the urinary catheter prosthesis further includes a hydraulic one-way shutter that is configured to delay return of the hydraulic liquid from the elastic valve balloon to the hydraulic activator, thereby delaying the elastic valve balloon from automatically transitioning from the open state to the closed resting state, such that the hydraulic valve assumes the closed resting state the set amount of time after being transitioned to the open state.

Inventive Concept 109. The method according to Inventive Concept 94, wherein the hydraulic valve is disposed in the urinary catheter prosthesis distal to the hydraulic activator.

Inventive Concept 110. The method according to Inventive Concept 94, wherein at least a portion of the hydraulic valve is part of the distal bladder assembly.

Inventive Concept 111. The method according to Inventive Concept 110, wherein the distal bladder assembly includes the hydraulic valve.

Inventive Concept 112. The method according to Inventive Concept 94, wherein the hydraulic activator at least partially surrounds the lumen at an axial location along the flexible intra-urethral catheter.

Inventive Concept 113. The method according to Inventive Concept 112, wherein the hydraulic activator surrounds at least 180 degrees of the lumen at the axial location.

Inventive Concept 114. The method according to Inventive Concept 113, wherein the hydraulic activator completely surrounds the lumen at the axial location.

Inventive Concept 115. The method according to Inventive Concept 94, wherein minimally-invasively inserting the urinary catheter prosthesis includes minimally-invasively inserting the urinary catheter prosthesis into the urethra of a male subject.

Inventive Concept 116. The method according to Inventive Concept 115, wherein the hydraulic activator is disposed at least 20 cm from the hydraulic valve, measured along the urinary catheter prosthesis.

Inventive Concept 117. The method according to Inventive Concept 115, wherein a length of the proximal intra-urethral assembly is between 7 and 30 cm.

Inventive Concept 118. The method according to Inventive Concept 94, wherein minimally-invasively inserting the urinary catheter prosthesis includes minimally-invasively inserting the urinary catheter prosthesis into the urethra of a female subject.

Inventive Concept 119. The method according to Inventive Concept 118, wherein the hydraulic activator is disposed at least 7 cm from the hydraulic valve, measured along the urinary catheter prosthesis.

Inventive Concept 120. The method according to Inventive Concept 118, wherein a length of the proximal intra-urethral assembly is between 3 and 10 cm.

Inventive Concept 121. The method according to Inventive Concept 94, wherein the hydraulic valve is disposed in the urinary catheter prosthesis distal to the hydraulic activator.

Inventive Concept 122. The method according to Inventive Concept 94, wherein distally advancing the urinary catheter prosthesis in the urethra includes distally advancing the urinary catheter prosthesis in the urethra until the distal bladder assembly is disposed in the bladder of the subject such that a urinary inlet of the distal bladder assembly is disposed in the bladder of the subject, and wherein the lumen of the urinary catheter prosthesis defines the urine path between the urinary inlet and the urinary outlet.

Inventive Concept 123. The method according to Inventive Concept 122, wherein the urinary inlet is disposed distal to the bladder anchor at least when the bladder anchor is in the deployed configuration.

Inventive Concept 124. The method according to Inventive Concept 122, wherein the hydraulic valve is configured such that (a) when in the open state, the hydraulic valve allows urine flow between the urinary inlet and the urinary outlet, and (b) when in the closed resting state, the hydraulic valve entirely blocks urine from entering the urinary inlet, flowing through the lumen, and exiting the urinary outlet.

Inventive Concept 125. The method according to Inventive Concept 124, wherein the hydraulic valve is configured, when in the closed resting state, to occlude the urinary inlet, and, when in the open state, not to occlude the urinary inlet.

Inventive Concept 126. The method according to Inventive Concept 122, wherein the hydraulic valve is configured to assume the open state upon inflation of a valve balloon of the hydraulic valve, wherein the hydraulic valve further includes a valve plug, which is attached to the valve balloon, and which is configured to occlude the urinary inlet when the hydraulic valve is in the closed resting state, and wherein the hydraulic valve is configured such that the inflation of the valve balloon moves the valve plug away from the urinary inlet, thereby transitioning the hydraulic valve to the open state.

Inventive Concept 127. The method according to Inventive Concept 126, wherein the hydraulic valve is configured such that the inflation of the valve balloon moves the valve plug in a distal direction away from the urinary inlet, thereby transitioning the hydraulic valve to the open state.

Inventive Concept 128. The method according to Inventive Concept 94, wherein distally advancing the urinary catheter prosthesis in the urethra includes distally advancing the urinary catheter prosthesis in the urethra until the distal bladder assembly is disposed in the bladder of the subject such that a urinary inlet of the distal bladder assembly is disposed in the bladder of the subject, wherein the lumen of the urinary catheter prosthesis defines the urine path between the urinary inlet and the urinary outlet, wherein the hydraulic valve is configured to assume the open state upon inflation of a valve balloon of the hydraulic valve, wherein the hydraulic valve is configured such that the urinary inlet is closed when the hydraulic valve is in the closed resting state, and wherein the hydraulic valve is configured to assume the open state when the valve balloon is inflated sufficiently to open the urinary inlet.

Inventive Concept 129. The method according to Inventive Concept 128, wherein the urinary inlet is shaped so as to define one or more slits that are closed when the hydraulic valve is in the closed resting state, and wherein the hydraulic valve is configured to assume the open state when the valve balloon is inflated sufficiently to push open the one or more slits.

Inventive Concept 130. The method according to Inventive Concept 129, wherein a distal portion of distal bladder assembly includes a flexible tubular casing that is shaped so as to define therethrough the one or more slits of the urinary inlet.

Inventive Concept 131. The method according to Inventive Concept 129, wherein the valve balloon and the one or more slits are located at respective axial positions along the distal bladder assembly, the axial positions at least partially non-axially-overlapping with each other.

Inventive Concept 132. The method according to Inventive Concept 129, wherein the valve balloon, when inflated, is shaped generally as an oblate spheroid lacking a section on one side.

Inventive Concept 133. The method according to Inventive Concept 94, wherein a distal portion of the distal bladder assembly includes a tubular casing, which is shaped so as to define a urinary inlet through the tubular casing at an axial position along the tubular casing, wherein distally advancing the urinary catheter prosthesis in the urethra includes distally advancing the urinary catheter prosthesis in the urethra until the distal bladder assembly is disposed in the bladder of the subject such that the urinary inlet is disposed in the bladder of the subject, wherein the lumen of the urinary catheter prosthesis defines the urine path between the urinary inlet and the urinary outlet, wherein the hydraulic valve further includes an elastic sleeve, which (a) defines one or more openings through the elastic sleeve, (b) is sealingly coupled to the tubular casing, and (c) surrounds the tubular casing, including at the axial position of the urinary inlet, wherein the hydraulic valve is configured such that when it is in the closed resting state, the elastic sleeve entirely occludes the urinary inlet, and wherein the hydraulic valve is configured to assume the open state when the valve balloon is inflated sufficiently to radially expand the elastic sleeve such that the elastic sleeve (a) does not occlude the urinary inlet and (b) defines a fluid flow path between (i) the one or more openings through the elastic sleeve and (ii) the urinary inlet.

Inventive Concept 134. The method according to Inventive Concept 133, wherein an axial position of the valve balloon along the distal bladder assembly is at least partially non-axially-overlapping with the axial position of the urinary inlet.

Inventive Concept 135. The method according to Inventive Concept 133, wherein the one or more openings through the elastic sleeve are located at respective radial positions around the tubular casing that are entirely non-radially-overlapping with a radial position of the urinary inlet around the tubular casing.

Inventive Concept 136. The method according to Inventive Concept 94, wherein the hydraulic valve includes a valve balloon, and wherein the hydraulic valve is configured to assume the open state upon inflation of the valve balloon.

Inventive Concept 137. The method according to Inventive Concept 136, wherein the hydraulic activator includes a control balloon, wherein the urinary catheter prosthesis further includes a hydraulic tube, which couples the control balloon in hydraulic communication with the valve balloon, and wherein the control balloon is configured, upon squeezing thereof, to inflate the valve balloon, thereby transitioning the hydraulic valve from the closed resting state to the open state.

Inventive Concept 138. The method according to Inventive Concept 94, wherein the flexible intra-urethral catheter is more flexible than the distal bladder assembly.

Inventive Concept 139. The method according to Inventive Concept 94, wherein at least a portion of the distal bladder assembly is disposed distal to the bladder anchor at least when the bladder anchor is in the deployed configuration.

Inventive Concept 140. The method according to Inventive Concept 94, wherein the hydraulic valve includes a piston.

Inventive Concept 141. The method according to Inventive Concept 94, wherein a length of the proximal intra-urethral assembly is between 3 and 30 cm, measured along the proximal intra-urethral assembly.

Inventive Concept 142. The method according to Inventive Concept 94, wherein the bladder anchor includes an anchor balloon, and wherein transitioning the bladder anchor to the deployed configuration includes inflating the anchor balloon to engage the bladder wall around a bladder neck.

Inventive Concept 143. The method according to Inventive Concept 142, wherein the bladder anchor further includes an anchor-balloon plug, which seals the anchor balloon when in a sealed state; and a plug-release line, which has a distal portion connected to the anchor-balloon plug, wherein minimally-invasively inserting the urinary catheter prosthesis into the subject includes disposing a proximal end of the plug-release line outside a body of the subject proximally beyond the proximal end of the flexible intra-urethral catheter, and wherein the bladder anchor is configured such that proximal pulling on the plug-release line transitions the anchor-balloon plug from the sealed state to an open state, in which the anchor-balloon plug does not seal the anchor balloon.

Inventive Concept 144. The method according to Inventive Concept 143, wherein the urinary catheter prosthesis further includes (a) a filling channel, which runs along a portion of the flexible intra-urethral catheter and has a distal end portion in fluid communication with an interior of the anchor balloon; and (b) a filling tube, which is removably coupled in fluid communication with a proximal end portion of the filling channel, and wherein inflating the anchor balloon includes inflating the anchor balloon via the filling tube and the filling channel, and, thereafter, decoupling the filling tube from the fluid communication with the proximal end portion of the filling channel.

Inventive Concept 145. The method according to Inventive Concept 144, wherein the plug-release line passes through a lumen of the filling tube when the filling tube is removably coupled in the fluid communication with a proximal end portion of the filling channel, and wherein decoupling the filling tube from the fluid communication with the proximal end portion of the filling channel includes proximally pulling the filling tube over and off of the plug-release line.

Inventive Concept 146. The method according to Inventive Concept 144,
  wherein the hydraulic activator includes:
    a control balloon, which is configured, upon squeezing thereof, to transition the hydraulic valve from the closed resting state to the open state; and
    a tubular counterforce surface against which the control balloon presses upon application of the pressure, wherein the counterforce surface is more rigid than the flexible intra-urethral catheter,
  wherein tubular counterforce surface is shaped so as to define a lateral opening, and
  wherein the filling tube passes through the lateral opening when the filling tube is removably coupled in the fluid communication with the proximal end portion of the filling channel.

Inventive Concept 147. The method according to Inventive Concept 143,
  wherein the hydraulic activator includes:
    a control balloon, which is configured, upon squeezing thereof, to transition the hydraulic valve from the closed resting state to the open state; and
    a tubular counterforce surface against which the control balloon presses upon application of the pressure, wherein the counterforce surface is more rigid than the flexible intra-urethral catheter,
  wherein, when the anchor-balloon plug is in the sealed state, a distal portion of the tubular counterforce surface applies a radially-outward force against the anchor-balloon plug, helping hold the anchor-balloon plug in place by friction, and
  wherein the method further includes:

pulling the tubular counterforce surface out of the flexible intra-urethral catheter via the proximal end thereof; and thereafter, transitioning the anchor-balloon plug from the sealed state to the open state by proximally pulling on the plug-release line.

Inventive Concept 148. The method according to Inventive Concept 143, wherein inserting and advancing the urinary catheter prosthesis includes disposing the urinary catheter prosthesis entirely within a body of the subject, except for a portion of the plug-release line.

Inventive Concept 149. The method according to Inventive Concept 148, wherein inserting and advancing the urinary catheter prosthesis includes using a guidewire during the inserting for disposing the urinary catheter prosthesis entirely within the body of the subject, except for the portion of the plug-release line.

Inventive Concept 150. The method according to Inventive Concept 142, wherein distally advancing the urinary catheter prosthesis in the urethra includes distally advancing the urinary catheter prosthesis in the urethra until the distal bladder assembly is disposed in the bladder of the subject such that a urinary inlet of the distal bladder assembly is disposed in the bladder of the subject, wherein the lumen of the urinary catheter prosthesis defines the urine path between the urinary inlet and the urinary outlet, and wherein the urinary inlet is disposed distal to the anchor balloon.

Inventive Concept 151. The method according to Inventive Concept 94, wherein the bladder anchor includes an umbrella anchor, and wherein transitioning the bladder anchor to the deployed configuration includes engaging the bladder wall around a bladder neck with a plurality of ribs of the umbrella anchor.

Inventive Concept 152. The method according to Inventive Concept 94, wherein transitioning the bladder anchor to the deployed configuration includes engaging the bladder wall around a bladder neck with a plurality of flexible petals of the bladder anchor.

Inventive Concept 153. The method according to Inventive Concept 94, wherein the hydraulic activator includes a control balloon, which is configured, upon squeezing thereof, to transition the hydraulic valve from the closed resting state to the open state.

Inventive Concept 154. The method according to Inventive Concept 153, further including, after transitioning the bladder anchor to the deployed configuration, squeezing the control balloon from outside the urethra.

Inventive Concept 155. The method according to Inventive Concept 153, wherein the urinary catheter prosthesis further includes a hydraulic tube, which couples the control balloon in hydraulic communication with the hydraulic valve such that the hydraulic valve transitions from the closed resting state to the open state upon the squeezing of the control balloon.

Inventive Concept 156. The method according to Inventive Concept 155, wherein the hydraulic valve includes a piston, and wherein the hydraulic tube couples the control balloon in the hydraulic communication with the piston.

Inventive Concept 157. The method according to Inventive Concept 155, wherein the hydraulic valve is configured to assume the open state upon inflation of a valve balloon of the hydraulic valve, and wherein the hydraulic tube couples the control balloon in the hydraulic communication with the valve balloon.

Inventive Concept 158. The method according to Inventive Concept 155, wherein the hydraulic activator is configured to transition the hydraulic valve from the closed resting state to the open state upon the application of the pressure having a minimum threshold value.

Inventive Concept 159. The method according to Inventive Concept 155, wherein the hydraulic activator is configured to transition the hydraulic valve from the closed resting state to the open state upon the application of the pressure at a minimum threshold rate of change.

Inventive Concept 160. The method according to Inventive Concept 159, wherein the hydraulic activator is configured to transition the hydraulic valve from the closed resting state to the open state upon the application of the pressure at between the minimum threshold rate of change and a maximum threshold rate of change.

Inventive Concept 161. The method according to Inventive Concept 153, wherein the hydraulic activator includes a counterforce surface against which the control balloon presses upon application of the pressure, and wherein the counterforce surface is more rigid than the flexible intra-urethral catheter.

Inventive Concept 162. The method according to Inventive Concept 161, wherein the counterforce surface is shaped as a tube.

Inventive Concept 163. The method according to Inventive Concept 153, wherein the control balloon at least partially surrounds the lumen at an axial location along the flexible intra-urethral catheter.

Inventive Concept 164. The method according to Inventive Concept 163, wherein the control balloon completely surrounds the lumen at the axial location.

Inventive Concept 165. The method according to Inventive Concept 94, wherein a greatest outer diameter of the flexible intra-urethral catheter is at least 5 mm.

Inventive Concept 166. The method according to Inventive Concept 94, wherein a greatest outer diameter of the flexible intra-urethral catheter is no more than 10 mm.

Inventive Concept 167. The method according to Inventive Concept 94, wherein a greatest outer diameter of the distal bladder assembly is at least 5 mm when the bladder anchor is in a non-radially-expanded deployment configuration.

Inventive Concept 168. The method according to Inventive Concept 94, wherein a greatest outer diameter of the distal bladder assembly is no more than 10 mm when the bladder anchor is in a non-radially-expanded deployment configuration.

Inventive Concept 169. The method according to Inventive Concept 94, wherein the hydraulic activator is configured to transition the hydraulic valve from the closed resting state to the open state upon the application of the pressure having a minimum threshold value.

Inventive Concept 170. The method according to Inventive Concept 94, wherein the hydraulic activator is configured to transition the hydraulic valve from the closed resting state to the open state upon the application of the pressure at a minimum threshold rate of change.

Inventive Concept 171. The method according to Inventive Concept 170, wherein the hydraulic activator is configured to transition the hydraulic valve from the closed resting state to the open state upon the application of the pressure at between the minimum threshold rate of change and a maximum threshold rate of change.

Inventive Concept 172. The method according to Inventive Concept 94, wherein the urinary catheter prosthesis does not include any electrical components.

Inventive Concept 173. The method according to Inventive Concept 94, wherein the urinary catheter prosthesis does not include any circuitry.

Inventive Concept 174. The method according to Inventive Concept 94, wherein the urinary catheter prosthesis does not include a battery.

Inventive Concept 175. The method according to Inventive Concept 94, wherein the urinary catheter prosthesis is not configured to receive power, either over a wire or wirelessly.

Inventive Concept 176. The method according to Inventive Concept 94, wherein the urinary catheter prosthesis does not include any magnets.

Inventive Concept 177. The method according to Inventive Concept 94, wherein the flexible intra-urethral catheter includes a sensor that is configured to sense, either continuously or periodically, one or more parameters of urine flowing through the lumen of the urinary catheter prosthesis.

Inventive Concept 178. The method according to Inventive Concept 177, wherein the one or more parameters include one or more parameters selected from the group consisting of: a flow rate of the urine, a pressure of the urine, a temperature of the urine, and a pH level of the urine.

Inventive Concept 179. The method according to Inventive Concept 177, wherein the sensor extends entirely around the lumen.

Inventive Concept 180. The method according to Inventive Concept 177, wherein the sensor includes a wireless transmitter, which is configured to wirelessly transmit signals indicative of the one or more sensed parameters.

Inventive Concept 181. The method according to Inventive Concept 177, wherein the sensor includes a flexible printed circuit board, which is wrapped partially or entirely around the lumen.

Inventive Concept 182. The method according to Inventive Concept 177, wherein the sensor is passive.

Inventive Concept 183. The method according to Inventive Concept 177, wherein the sensor includes a resonance circuit.

The present invention will be more fully understood from the following detailed description of embodiments thereof, taken together with the drawings, in which:

BRIEF DESCRIPTION OF THE DRAWINGS

FIGS. 1A-B are schematic illustrations of a user-controllable urinary catheter prosthesis for minimally-invasive positioning in a subject, in accordance with an application of the present invention;

FIGS. 7A and 7B are a schematic illustration and a schematic cross-sectional illustration of a distal bladder assembly, taken along a line VIIB-VIIB of FIG. 7A, with a hydraulic valve thereof in a closed resting state, in accordance with an application of the present invention;

FIGS. 8A and 8B-E are a schematic illustration and schematic cross-sectional illustrations of the distal bladder assembly of FIGS. 7A-B, taken along lines VIIIB-VIIIB, VIIIC-VIIIC, VIIID-VIIID, and VIIIE-VIIIE of FIG. 8A, respectively, with the hydraulic valve of FIGS. 7A-B in an open state, in accordance with an application of the present invention;

FIGS. 9A and 9B are a schematic illustration and a schematic cross-sectional illustration of another distal bladder assembly, taken along a line IXB-IXB of FIG. 9A, with a hydraulic valve thereof in a closed resting state, in accordance with an application of the present invention;

FIGS. 11A and 11B-C are a schematic illustration and schematic cross-sectional illustrations of yet another distal bladder assembly, taken along lines XIB-XIB and XIC-XIC of FIG. 11A, respectively, with a hydraulic valve thereof in a closed resting state, in accordance with an application of the present invention;

FIGS. 12A and 12B-C are a schematic illustration and schematic cross-sectional illustrations of the distal bladder assembly of FIGS. 11A-C, taken along lines XIIB-XIIB and XIIC-XIIC of FIG. 12A, respectively, with the hydraulic valve of FIGS. 11A-C in an open state, in accordance with an application of the present invention;

DETAILED DESCRIPTION OF APPLICATIONS

Figure 1A:
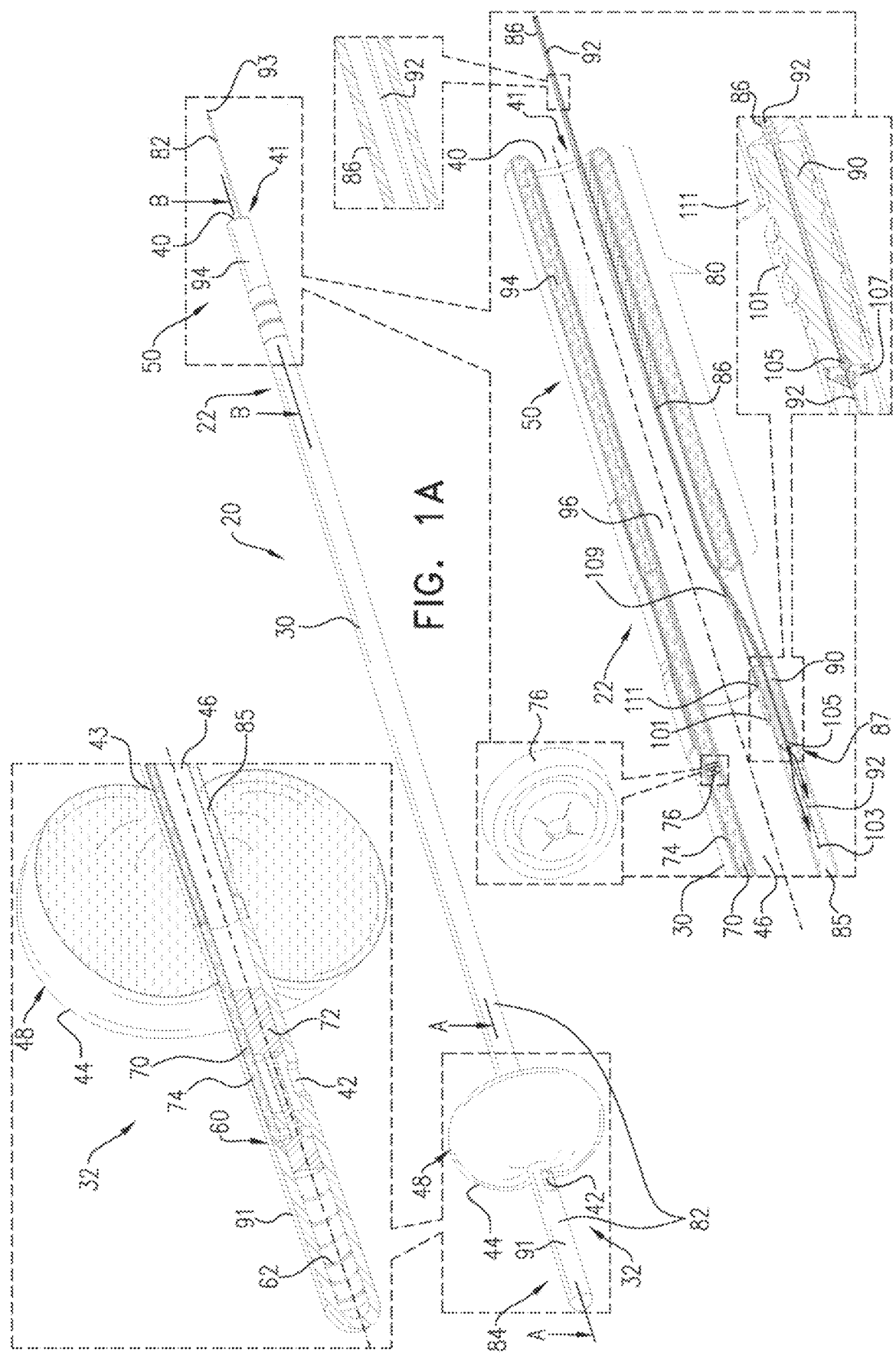
Figure 2:
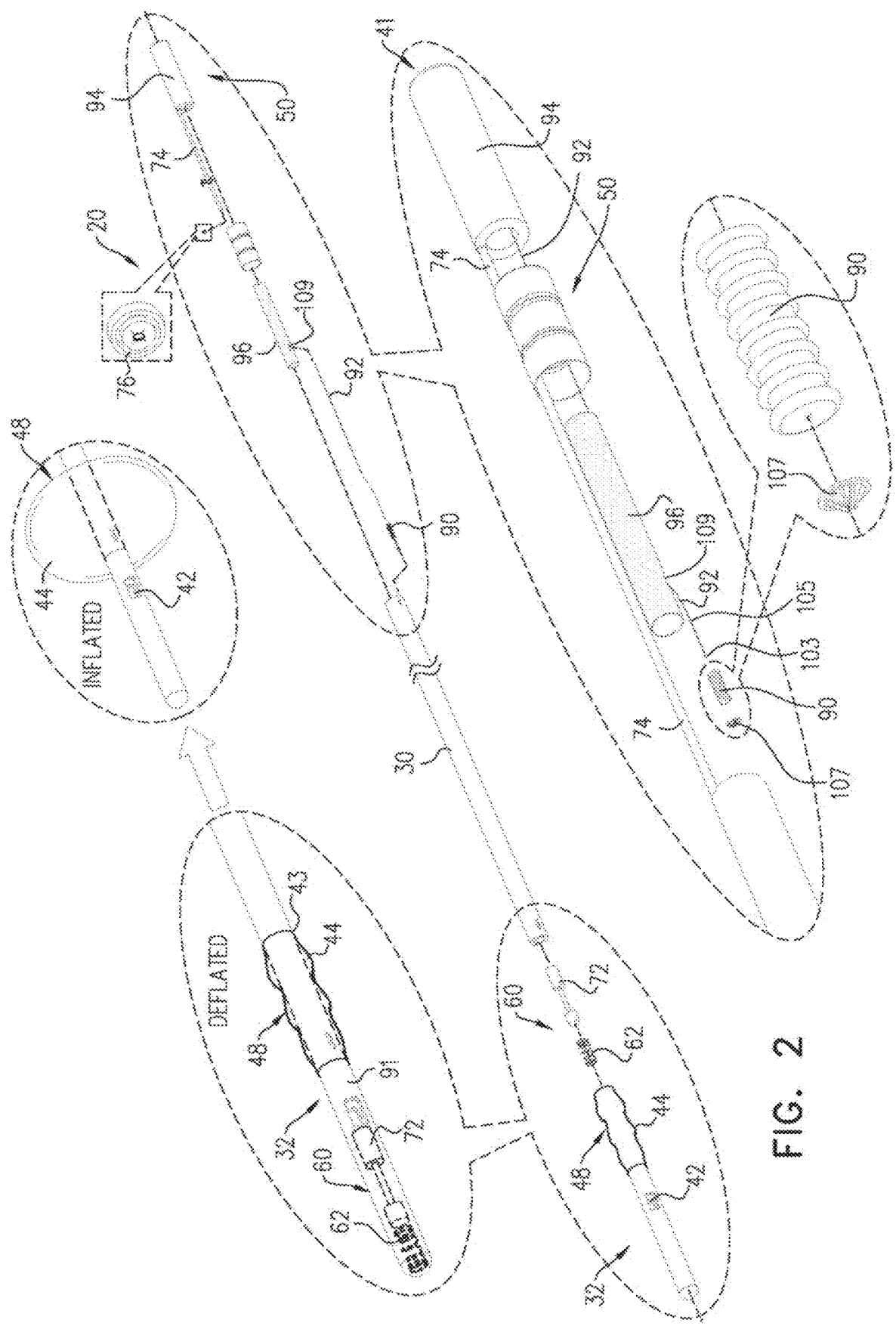
FIG. 2 is a schematic exploded view showing components of the urinary catheter prosthesis of FIGS. 1A-B, in accordance with an application of the present invention.

FIGS. 1A-B are schematic illustrations of a user-controllable urinary catheter prosthesis 20 for minimally-invasive positioning in a subject, in accordance with an application of the present invention. FIG. 2 is a schematic exploded view showing components of urinary catheter prosthesis 20, in accordance with an application of the present invention. Urinary catheter prosthesis 20 may be used to replace a conventional intermittent urinary catheter, which must be inserted and removed (replaced) several times a day when the subject needs to urinate. As used in the present application, including in the claims and Inventive Concepts, "minimally-invasive insertion" means non-surgical insertion, i.e., insertion without making any incisions in or otherwise penetrating any tissue of the subject, e.g., inserting using conventional techniques for inserting intermittent catheters, such as ordinary balloon catheter or umbrella catheter, e.g., Foley catheters.

Urinary catheter prosthesis 20 comprises a proximal intra-urethral assembly 22, which is configured to be disposed entirely within a urethra 102 by insertion via a meatus 104 of the subject, typically using ordinary urinary catheterization techniques. Because proximal intra-urethral assembly 22 is configured to disposed entirely with the urethra, it does not penetrate tissue of the urethra. Proximal intra-urethral assembly 22 comprises:

a flexible intra-urethral catheter 30, which is shaped so as to define a urinary outlet 40 at a proximal end 41 of flexible intra-urethral catheter 30; and a user-activatable hydraulic activator 50, which is disposed along flexible intra-urethral catheter 30 (because flexible intra-urethral catheter 30 is configured to be disposed entirely within urethra 102, so is hydraulic activator 50).

Typically, all external tissue-facing elements of urinary catheter prosthesis 20, including flexible intra-urethral catheter 30, comprise biocompatible materials, such non-sticky, hydrophilic, or hydrophobic polymers, which do not corrode or degrade in a urine environment and prevent calcification and bacteria settlements. For example, conventional biocompatible materials may be used that are used in conventional Foley catheters. Internal elements of the prosthesis, such as hydraulic valve 60 and hydraulic activator 50, may comprise, for example, Nitinol, medical grade stainless steel, or silicon.

Reference is still made to FIGS. 1A-B and 2. Urinary catheter prosthesis 20 further comprises a distal bladder assembly 32, which extends distally from a distal end 43 of flexible intra-urethral catheter 30, and is shaped so as to define a urinary inlet 42, such as a single urinary inlet 42 or a plurality of urinary inlets 42. Distal bladder assembly 32 is configured to be disposed, by insertion via urethra 102, in a bladder of the subject such that urinary inlet 42 is disposed in the bladder of the subject. Urinary catheter prosthesis 20 is shaped so as to define a lumen 46 that defines a urine path between urinary inlet 42 and urinary outlet 40. Optionally, flexible intra-urethral catheter 30 is more flexible than distal bladder assembly 32, although this is not necessarily the case.

Urinary catheter prosthesis 20 typically further comprises a bladder anchor 48, which is coupled to distal bladder assembly 32, and is configured to engage an inner surface of a wall of the bladder when in a deployed configuration, so as to anchor urinary catheter prosthesis 20 in place.

Reference is still made to FIGS. 1A-B and 2. For some applications, urinary catheter prosthesis 20 further comprises a hydraulic valve 60, which is disposed in urinary catheter prosthesis 20 distal to hydraulic activator 50, and which is configured to assume (a) an open state, as shown in FIG. 2 (as well as in FIGS. 3B and 3C), in which hydraulic valve 60 allows urine flow between urinary inlet 42 and urinary outlet 40 (i.e., allows urination), and (b) a closed resting state, as shown in FIGS. 1A-B (as well as in FIGS. 3A and 3D), in which hydraulic valve 60 entirely blocks urine from entering urinary inlet 42, flowing through lumen 46, and exiting urinary outlet 40. Urinary catheter prosthesis 20 thus blocks urination and leakage of urine from the subject's bladder via lumen 46 when hydraulic valve 60 is in its closed resting state. Optionally, hydraulic valve 60 comprises one or more thermodynamically shape-memory materials.

Hydraulic activator 50 is configured to transition hydraulic valve 60 from the closed resting state to the open state upon application of pressure to hydraulic activator 50. The pressure is typically provided by the user pressing with his or her finger(s).

Typically, hydraulic valve 60 is configured to remain in the open state even after cessation of the application of the pressure to hydraulic activator 50. This allows the subject to briefly apply pressure (typically with a single squeeze) to hydraulic activator 50, release the pressure, and complete the urination after release of the pressure. Therefore, the subject does not need to apply the pressure to the hydraulic activator 50 throughout the urination.

Typically, hydraulic valve 60 is configured, after remaining in the open state even after the cessation of the application of the pressure to hydraulic activator 50, to automatically transition to the closed resting state such that hydraulic valve 60 assumes the closed resting state a set amount of time after being transitioned to the open state, thereby automatically stopping urination. For example, the set amount of time may have a value that falls in the range of 15 to 360 seconds, e.g., in the range of 20 to 240 second, such as in the range of 60 to 120 seconds, such as 240 second, e.g., 120 seconds, such as 60 seconds or 30 seconds.

For some applications, hydraulic valve 60 further comprises a spring 62, which is configured to store elastic energy during transitioning of hydraulic valve 60 from the closed resting state to the open state, and to automatically transition hydraulic valve 60 to the closed resting state by releasing the elastic energy.

For some applications, the set amount of time is set by properties of spring 62, which optionally is insertable (such as by the subject) before insertion of urinary catheter prosthesis 20 into urethra 102; for example, a plurality of different springs having different configurations may be provided, each of the configurations corresponding with a different set amount of time. Alternatively, several different models of urinary catheter prosthesis 20 may be provided (e.g., as a kit), having respective different set amounts of time. Further alternatively, urinary catheter prosthesis 20 may comprise a user control that allows the set amount of time to be set by the user before insertion into urethra 102.

For some applications, urinary catheter prosthesis 20 comprises hydraulic liquid 70, and hydraulic valve 60 comprises a piston 72. Hydraulic activator 50 is configured to transition hydraulic valve 60 from the closed resting state to the open state by transferring at least a portion of hydraulic liquid 70 from hydraulic activator 50 to hydraulic valve 60 (typically via a hydraulic tube 74, which is optionally at least partially embedded in a wall of flexible intra-urethral catheter 30). (Hydraulic tube 74 may comprise a plurality of sub-tubes that are coupled in fluid communication with one another.)

Reference is still made to FIGS. 1A-B and 2. For some applications, urinary catheter prosthesis 20 further comprises a hydraulic semi-one-way shutter 76 (i.e., a semi-oneway valve) that is configured to delay return of hydraulic liquid 70 from hydraulic valve 60 to hydraulic activator 50, thereby delaying piston 72 from automatically transitioning from the open state to the closed resting state, such that hydraulic valve 60 assumes the closed resting state the set amount of time after being transitioned to the open state. Typically, hydraulic semi-one-way shutter 76 is disposed along a fluid path of hydraulic tube 74.

For some applications, hydraulic semi-one-way shutter 76 comprises a cross-slit valve that is shaped so as to define cross slits that allow flow in essentially one direction at a first rate, and a centered opening that allows flow in the opposite direction at a second rate that is less than the first rate. For example, the modified cross-slit valve may comprise silicone. For example, the modified cross-slit valve may comprise a silicon medical-grade one-way (duckbill) micro-valve (AptarGroup, Inc., Crystal Lake, Ill., USA), in which the one-way (duckbill) micro valve may be fabricated by modifying an Aptar Midland valve by cutting the duckbill "beak" in order to achieve the set amount of urination time, in order to enable hydraulic liquid 70 returned to the activator 50. Alternatively, semi-one-way shutter 76 is formed as an integral part of hydraulic tube 74.

For other applications, hydraulic tube 74 itself is configured to delay return of hydraulic liquid 70 from hydraulic valve 60 to hydraulic activator 50, thereby delaying piston 72 from automatically transitioning from the open state to the closed resting state, such that hydraulic valve 60 assumes the closed resting state the set amount of time after being transitioned to the open state. For example, hydraulic tube 74 may have a relatively small internal diameter that delays flow through the tube, such as no more than 2.5 mm.

Alternatively, urinary catheter prosthesis 20 comprises hydraulic semi-one-way shutter 76 and hydraulic tube 74 itself is configured to delay return of hydraulic liquid 70 from hydraulic valve 60 to hydraulic activator 50.

Typically, spring 62 is configured to move piston 72 while releasing the elastic energy.

For some applications, hydraulic valve 60 is disposed at least partially in distal bladder assembly 32, such as shown in the figures. For some applications, hydraulic valve 60 is disposed entirely in distal bladder assembly 32, such as shown in the figures.

For some applications, hydraulic activator 50 at least partially surrounds lumen 46 at an axial location 80 along flexible intra-urethral catheter 30. For example, hydraulic activator 50 may surround at least 180 degrees of lumen 46 at axial location 80; for example, hydraulic activator 50 may completely surround lumen 46 at axial location 80, such as shown in the figures.

Typically, hydraulic valve 60 is configured, when in the closed resting state, to occlude urinary inlet 42, and, when in the open state, not to occlude urinary inlet 42.

Reference is still made to FIGS. 1A-B and 2. For some applications, hydraulic activator 50 comprises a control balloon 94, which is configured, upon squeezing thereof, to transition hydraulic valve 60 from the closed resting state to the open state. For some applications, hydraulic tube 74 couples control balloon 94 in hydraulic communication with hydraulic valve 60 such that hydraulic valve 60 transitions from the closed resting state to the open state upon the squeezing of control balloon 94. For applications in which hydraulic valve 60 comprises piston 72, hydraulic tube 74 couples control balloon 94 in the hydraulic communication with piston 72 via semi-one-way shutter 76. Thus, urinary catheter prosthesis 20 is typically a closed system containing hydraulic liquid 70 (which typically comprises, e.g., consists of, saline solution).

Control balloon 94 is shaped so as to define a fluid reservoir that contains more hydraulic liquid 70 when hydraulic valve 60 is in the closed resting state than when hydraulic valve 60 is in the open state. The wall(s) of control balloon 94 may be defined by an integral piece of material, or may be defined by a plurality of elements sealingly coupled together. The wall(s) of control balloon 94 may or may not comprise elastic material(s). Optionally, an outer wall of control balloon 94 is defined by a catheter tube that also is shaped so as to define flexible intra-urethral catheter 30.

For some applications, hydraulic activator 50 is configured to transition hydraulic valve 60 from the closed resting state to the open state upon the application of the pressure having a minimum threshold value. Alternatively, for some applications, hydraulic activator 50 is configured to transition hydraulic valve 60 from the closed resting state to the open state upon the application of the pressure at a minimum threshold rate of change. Optionally, hydraulic activator 50 is configured to transition hydraulic valve 60 from the closed resting state to the open state upon the application of the pressure at between the minimum threshold rate of change and a maximum threshold rate of change. Providing the thresholds described in this paragraph may prevent undesired transition of hydraulic valve 60 to the open state by any transient pressure unintentionally applied to control balloon 94 by the subject's body, such as caused by coughing, jumping, or other natural motion of the subject's body.

For some applications, as shown in FIGS. 1B and 2, hydraulic activator 50 comprises a counterforce surface 96 against which control balloon 94 presses upon application of the pressure. Counterforce surface 96 is more rigid than flexible intra-urethral catheter 30. For some applications, counterforce surface 96 is shaped as a tube, as shown in the figures. Counterforce surface 96 may also help prevent collapse of flexible intra-urethral catheter 30, such that flexible intra-urethral catheter 30 remains open to urinary outlet 40 at all times.

Typically, control balloon 94 at least partially surrounds, such as completely surrounds, lumen 46 at axial location 80 along flexible intra-urethral catheter 30.

Alternatively, for some applications, urinary catheter prosthesis 20 comprises a non-hydraulic mechanical valve instead of hydraulic valve 60. In these applications, urinary catheter prosthesis 20 typically does not comprise other hydraulic components, such as hydraulic activator 50.

Reference is still made to FIGS. 1A-B and 2. For some applications, at least a distal portion 84 of distal bladder assembly 32 is disposed distal to bladder anchor 48 at least when bladder anchor 48 is in the deployed configuration. For example, urinary inlet 42 may be disposed distal to bladder anchor 48 at least when bladder anchor 48 is in the deployed configuration.

Reference is still made to FIGS. 1A-B and 2. For some applications, bladder anchor 48 comprises an anchor balloon 44, which is configured to engage the bladder wall around the bladder neck when anchor balloon 44 is in an inflated deployed configuration. Typically, urinary inlet 42 is disposed distal to anchor balloon 44. For these applications, anchor balloon 44 is optionally inflated using techniques described hereinbelow with reference to FIGS. 1A-B, 2, and 5B-D, and is optionally deflated using techniques described hereinbelow with reference to FIGS. 1A-B, 2, and 5E-F, or using techniques described hereinbelow with reference to FIGS. 13-15B.

For some applications, distal portion 84 of distal bladder assembly 32 comprises a tubular casing 91.

Reference is still made to FIGS. 1A-B and 2. For some applications, urinary catheter prosthesis 20 comprises a catheter tube that (a) is shaped so as to define both flexible intra-urethral catheter 30 and tubular casing 91 of distal portion 84 of distal bladder assembly 32 and (b) passes through an interior of bladder anchor 48 (including through an interior of anchor balloon 44 for configurations in which bladder anchor 48 comprises anchor balloon 44).

For some applications, anchor balloon 44 is secured to the top rim portion of the catheter assembly and built as part of the catheter proximal side under the hydraulic valve.

For some applications, a greatest outer diameter of flexible intra-urethral catheter 30 is at least 5 mm, such as at least 6 mm, and/or no more than 10 mm.

For some applications, a greatest outer diameter of distal bladder assembly 32 is at least 5 mm, e.g., at least 6 cm, and/or no more than 10 mm, when bladder anchor 48 is in a non-radially-expanded deployment configuration.

Typically, urinary catheter prosthesis 20 does not comprise any electrical components.

Typically, urinary catheter prosthesis 20 does not comprise any circuitry.

Typically, urinary catheter prosthesis 20 does not comprise a battery.

Typically, urinary catheter prosthesis 20 is not configured to receive power, either over a wire or wirelessly.

Typically, urinary catheter prosthesis 20 does not comprise any magnets.

Reference is now made to FIGS. 3A-E, which are schematic illustrations of urinary catheter prosthesis 20 positioned in a male subject, in accordance with an application of the present invention. Reference is also made to FIG. 4, which is a schematic illustration of urinary catheter prosthesis 20 position in a female subject, in accordance with an application of the present invention.

Figure 3A:
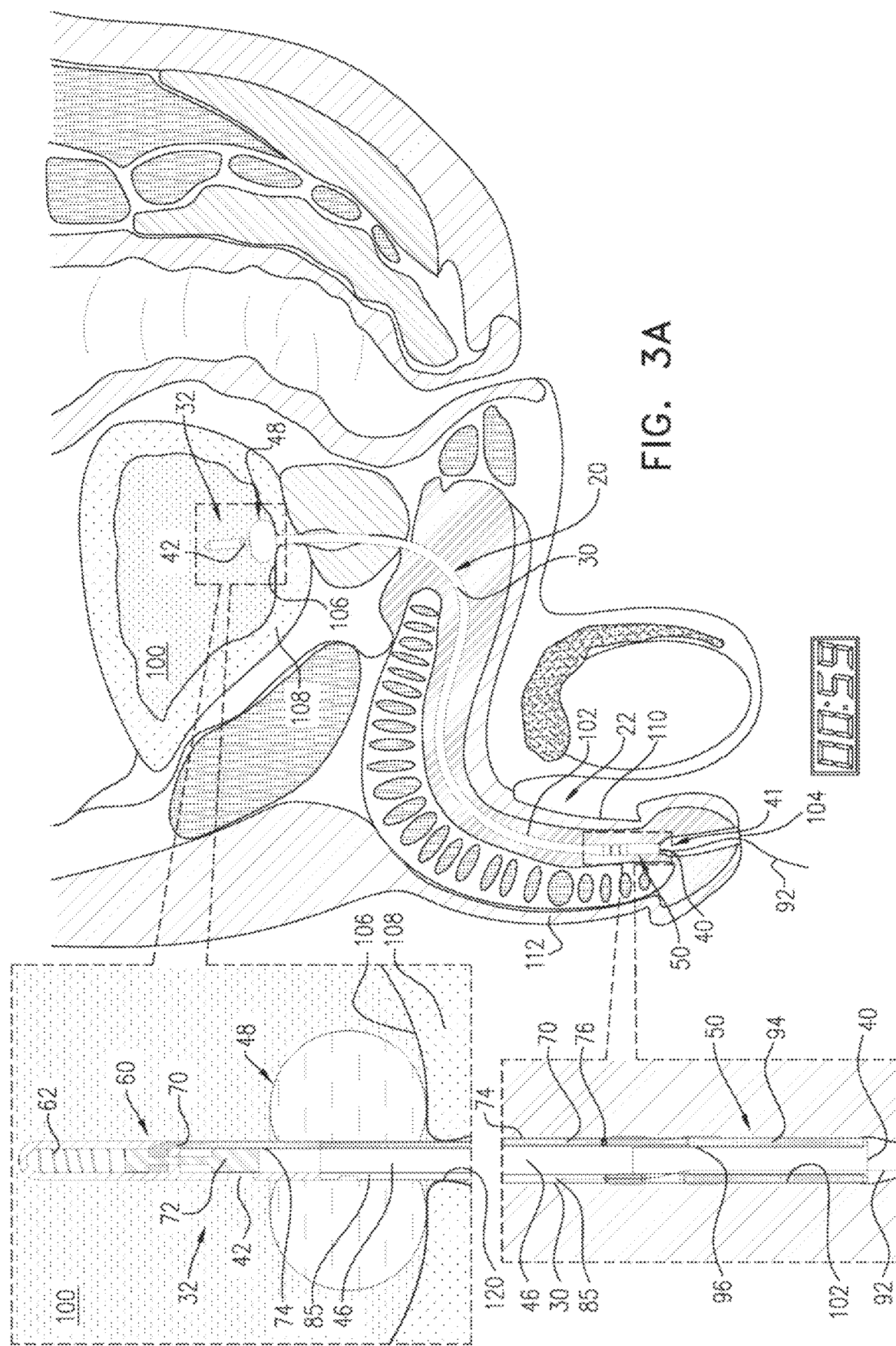
FIGS. 3A-E are schematic illustrations of the urinary catheter prosthesis of FIGS. 1A-B positioned in a male subject, in accordance with an application of the present invention.
Figure 4:
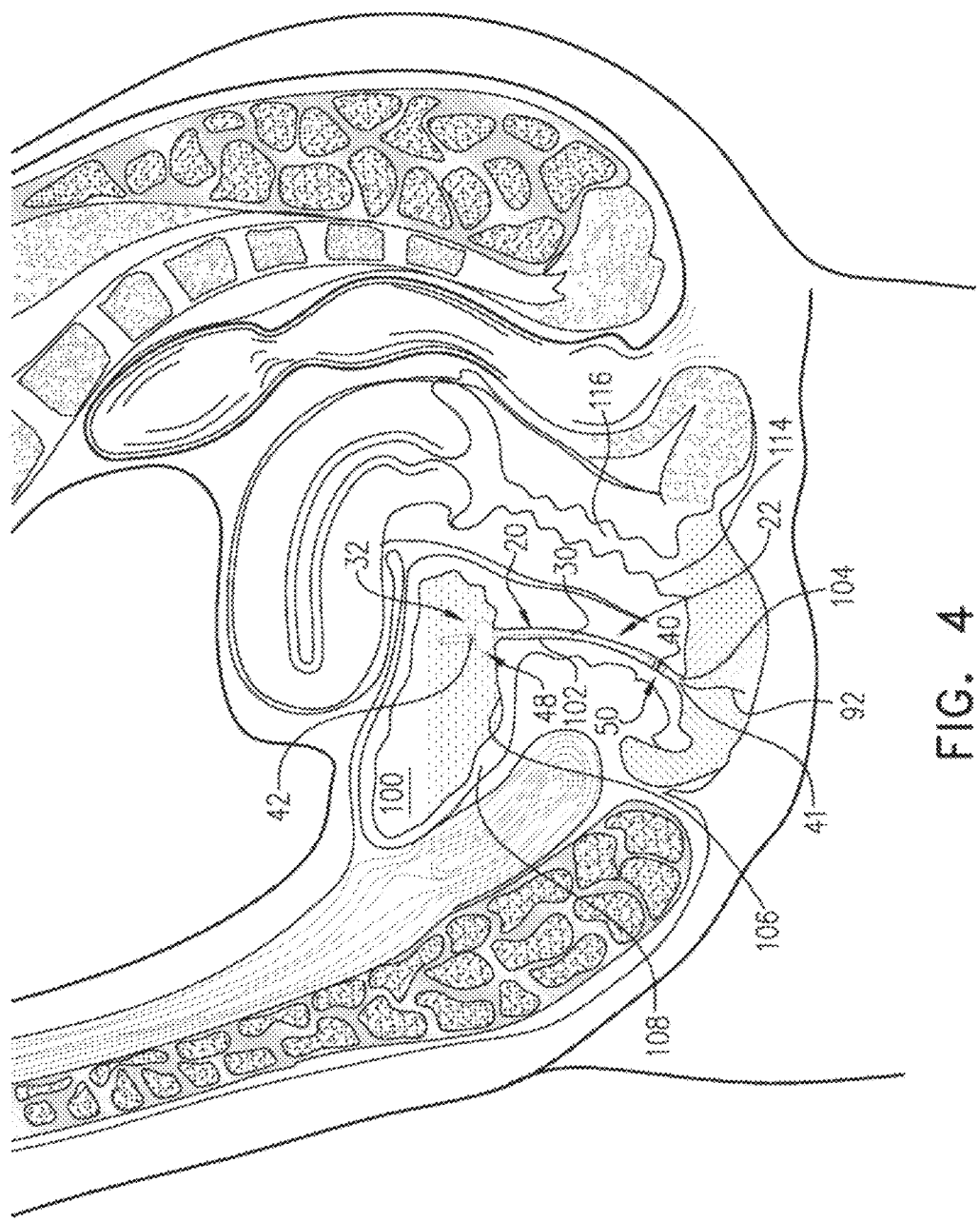
FIG. 4 is a schematic illustration of the urinary catheter prosthesis of FIGS. 1A-B positioned in a female subject, in accordance with an application of the present invention.

FIGS. 3A and 4 show urinary catheter prosthesis 20 with hydraulic valve 60 in the closed resting state, in which urinary catheter prosthesis 20 prevents urine from being voided from a bladder 100 of the subject. As used in the present application, including in the claims and Inventive Concepts, the "bladder" includes the portion of the urinary bladder that stores urine, as well as the bladder neck, which is a constricted portion of the urinary bladder at which its inferolateral surfaces meet at the opening of urethra 102.

Figure 3B:
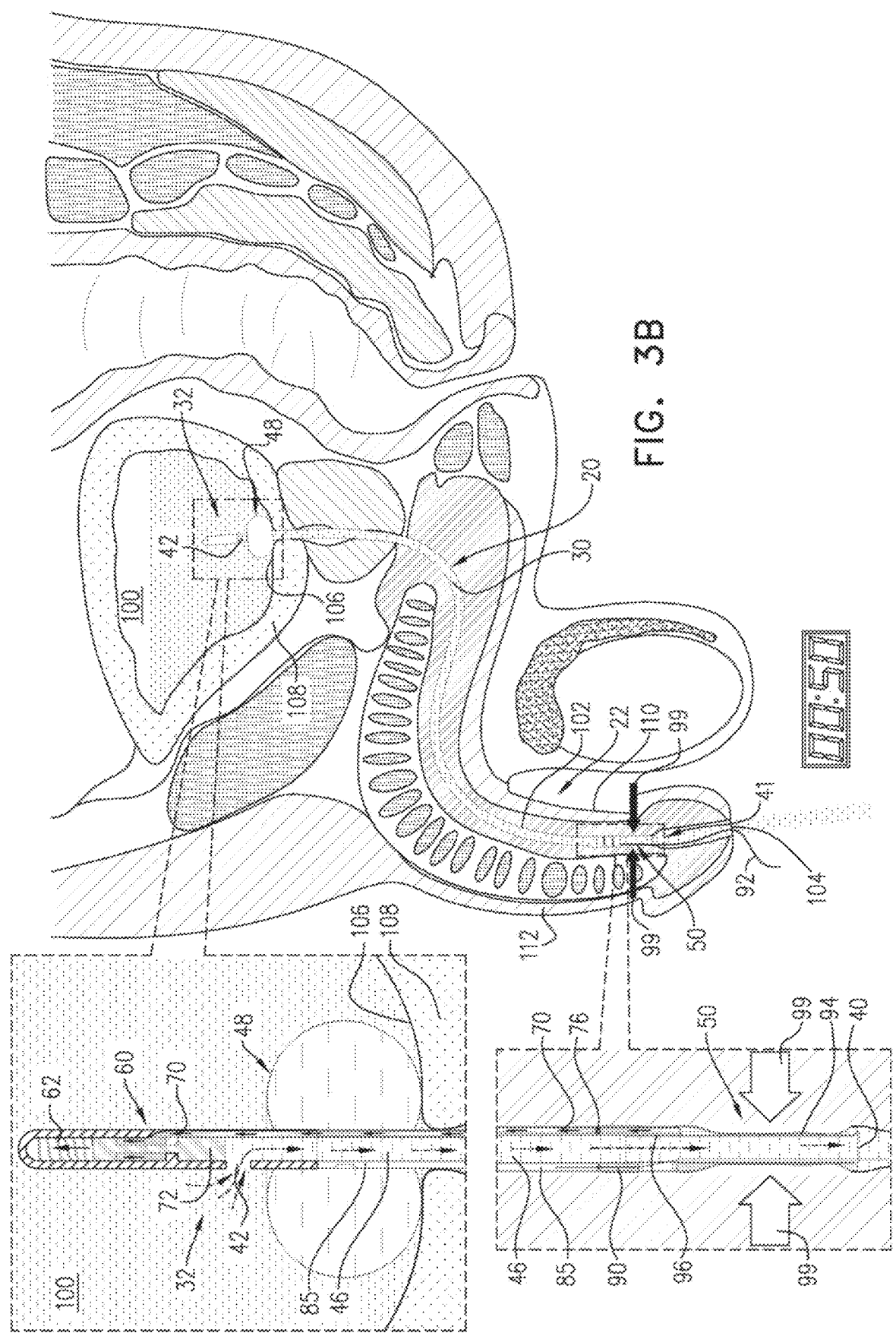

As shown in FIG. 3B, when the subject needs to urinate, the subject applies the pressure to hydraulic activator 50 from outside urethra 102 to transition hydraulic valve 60 from the closed resting state to the open state. For applications in which hydraulic activator 50 comprises control balloon 94, the subject applies the pressure by squeezing control balloon 94 from outside urethra 102.

When the subject is male, such as shown in FIGS. 3A-E, the subject applies the pressure to hydraulic activator 50 by applying pressure to an external surface 110 of a penis 112, typically by squeezing penis 112, such as symbolically indicated by arrows 99 in FIG. 3B. When the subject is female, such as shown in FIG. 4, the subject applies the pressure to hydraulic activator 50 by applying pressure, from within a vagina 116, to a wall 114 of vagina 116 (application of pressure not shown).

As indicated symbolically with exemplary time values in FIGS. 3A-D, hydraulic activator 50 is typically configured to remain in the open state even after cessation of the application of the pressure to hydraulic activator 50. This allows the subject to briefly apply pressure (typically with a single squeeze) to hydraulic activator 50, release the pressure, and complete the urination after release of the pressure. Therefore, the subject does not need to apply the pressure to the hydraulic activator 50 throughout the urination.

Figure 3C:
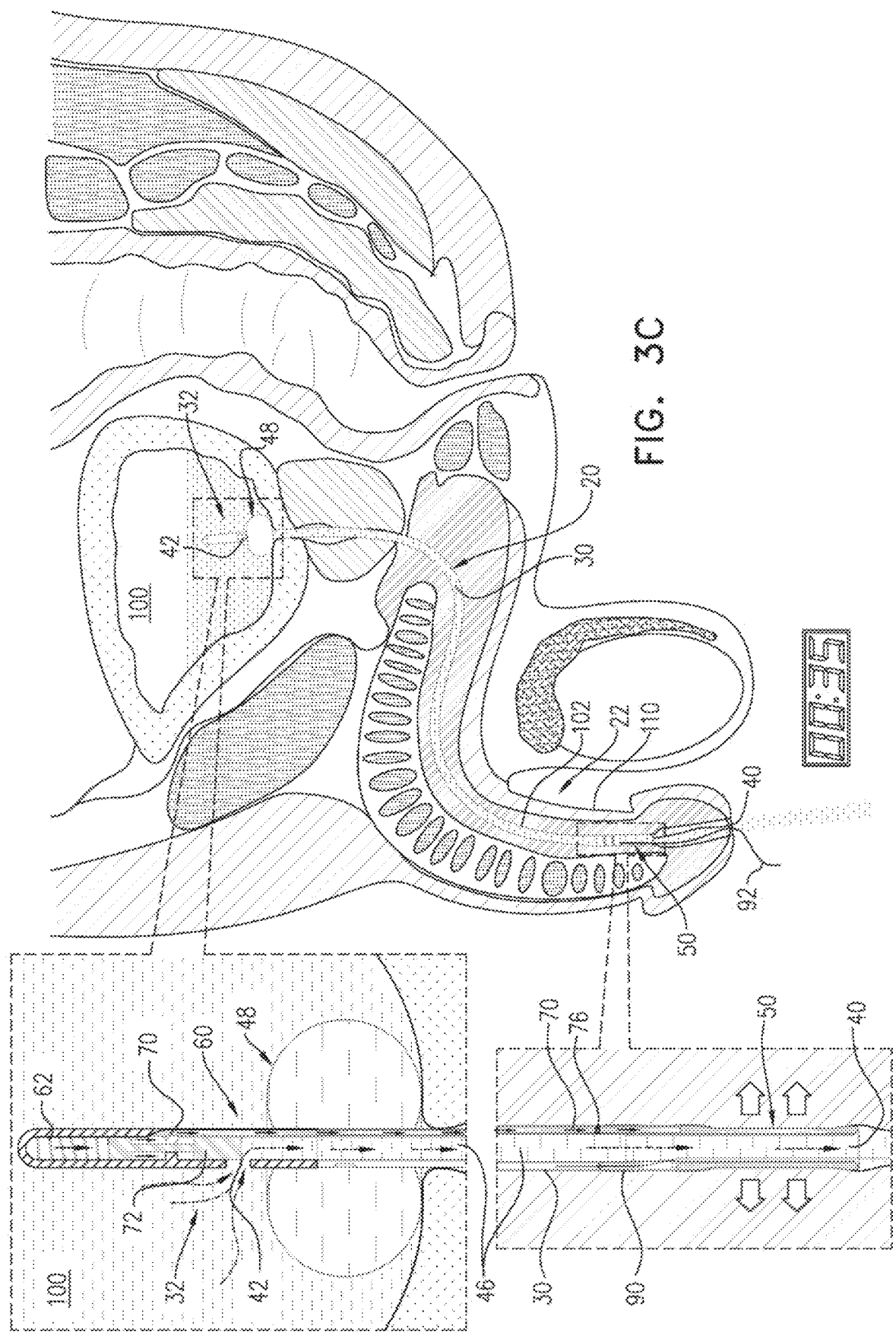
Figure 3D:
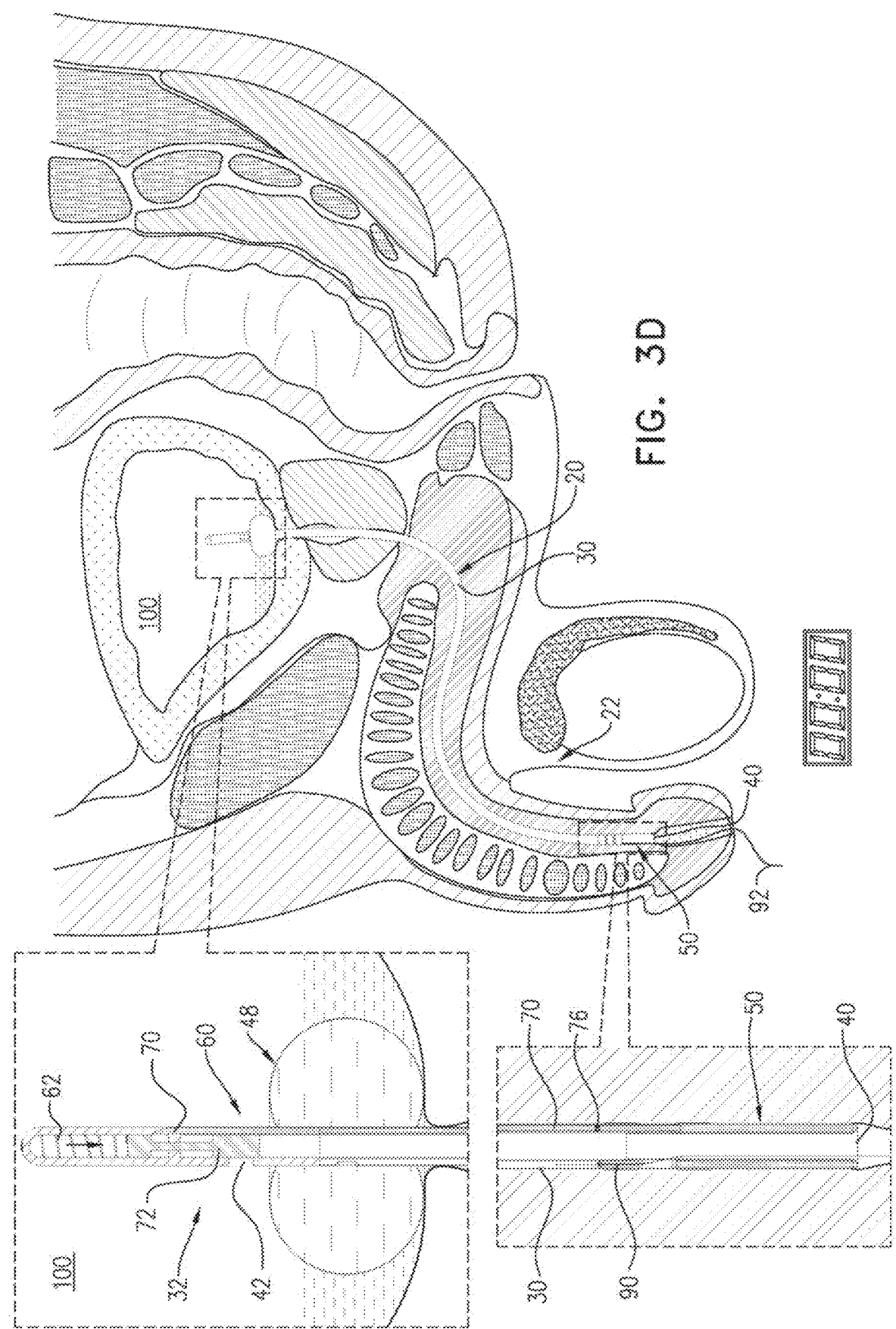
Figure 3E:
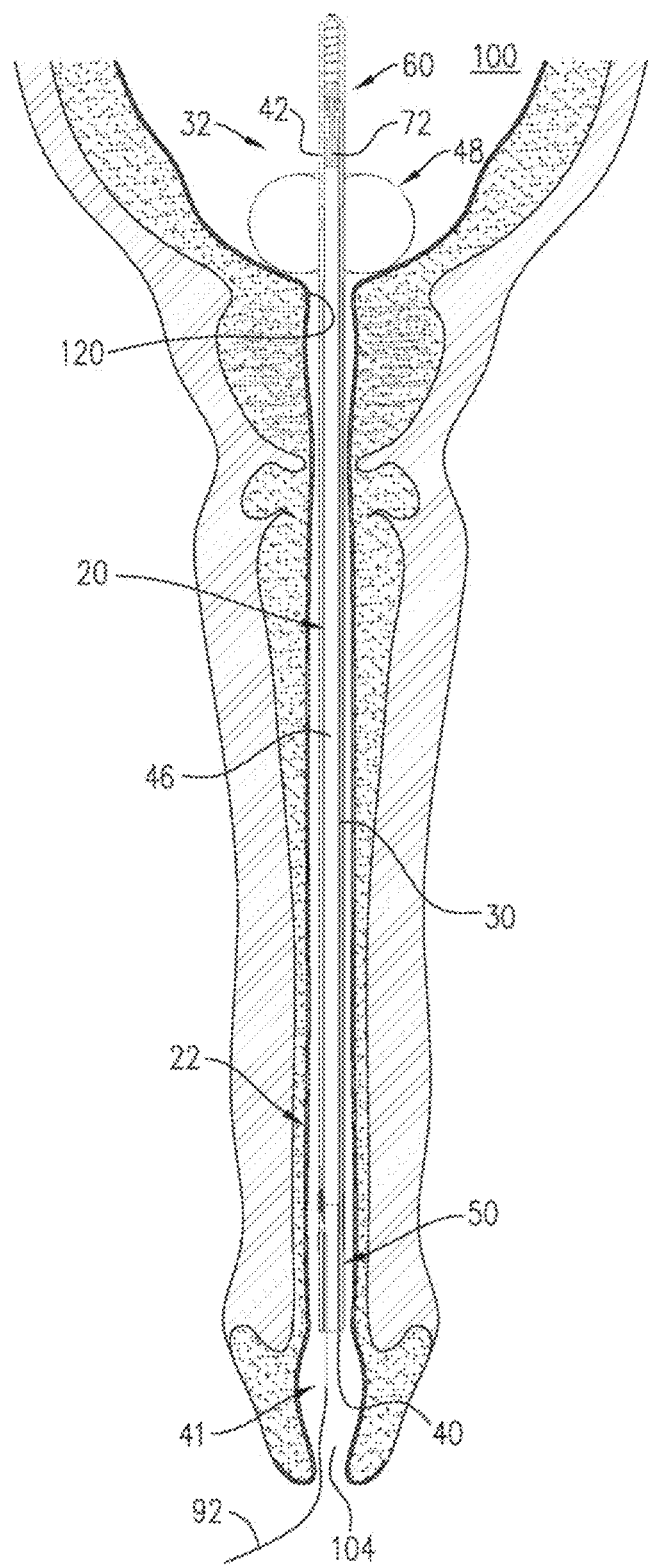

As shown in FIGS. 3C-D, hydraulic activator 50 is typically configured, after remaining in the open state even after the cessation of the application of the pressure to hydraulic activator 50, to automatically transition to the closed resting state such that hydraulic valve 60 assumes the closed resting state a set amount of time after being transitioned to the open state, as indicated symbolically with exemplary time values in FIG. 3C-D.

For some applications, the open state includes an entirely-open sub-state and a partially-open sub-state, as shown in FIG. 3B. For some of these applications, hydraulic valve 60 is configured to:
  assume the entirely-open sub-state immediately upon being transitioned to the open state, as shown in the transition between FIG. 3A and FIG. 3B,
  thereafter, automatically transition to the partially-open sub-state, as shown in FIG. 3C, and
  thereafter, automatically transition to the closed resting state the set amount of time after being transitioned to the entirely-open sub-state, as shown in FIG. 3D.

In configurations of urinary catheter prosthesis 20 configured for male subjects, hydraulic activator 50 is typically disposed at least 7 cm from hydraulic valve 60 for young boys, measured along urinary catheter prosthesis 20 and at least 20 cm for adult males. In configurations of urinary catheter prosthesis 20 configured for female subjects, hydraulic activator 50 is typically disposed at least 3 cm from hydraulic valve 60 for young girl and at least 7 cm for adult females, measured along urinary catheter prosthesis 20.

For some applications, a length of proximal intra-urethral assembly 22 is between 3 and 30 cm, measured along proximal intra-urethral assembly 22. In configurations of urinary catheter prosthesis 20 configured for male subjects, the length of proximal intra-urethral assembly 22 is typically between 7 and 30 cm. In configurations of urinary catheter prosthesis 20 configured for female subjects, the length of proximal intra-urethral assembly 22 is typically between 3 and 10 cm.

Reference is made to FIGS. 5A-E, which are schematic illustrations of techniques for minimally-invasively positioning urinary catheter prosthesis 20 and inflating and deflating anchor balloon 44 of bladder anchor 48, in accordance with respective applications of the present invention. Reference is also made to FIGS. 5F-G, which are schematic illustrations of a technique for removing urinary catheter prosthesis 20 from the subject's body, in the event of a normal removal at the end of the using period or at any time as required by the patient or the clinical staff, in accordance with an application of the present invention. Although these techniques are illustrated for a male subject, they may also be applied for a female subject. Some aspects of these minimally-invasively positioning techniques are similar to techniques conventionally used for inserting and anchoring balloon catheters known as Foley catheters.

Figure 5A:
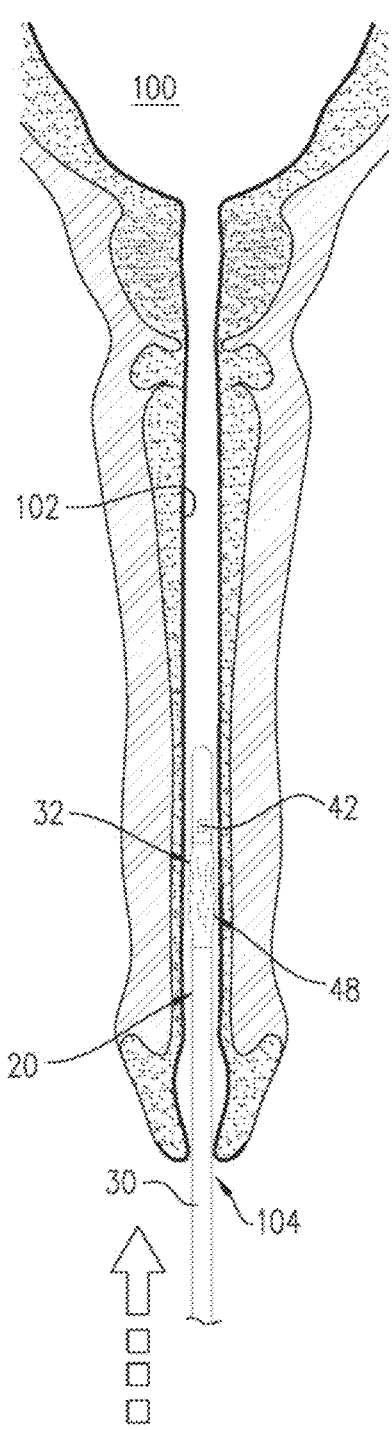
FIGS. 5A-E are schematic illustrations of techniques for minimally-invasively positioning the urinary catheter prosthesis of FIGS. 1A-B and inflating and deflating an anchor balloon of a bladder anchor of the urinary catheter prosthesis, in accordance with respective applications of the present invention.

As shown in FIG. 5A, urinary catheter prosthesis 20 is minimally-invasively inserted into urethra 102 via meatus 104, while bladder anchor 48 is in a non-radially-expanded deployment configuration.

Figure 5B:
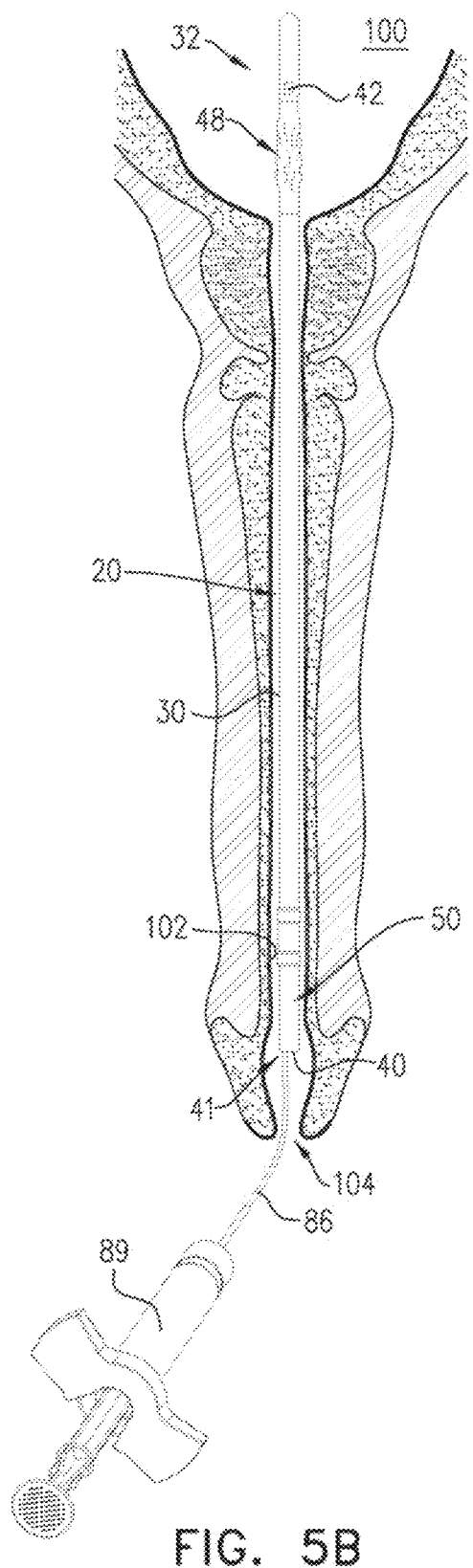

As shown in FIG. 5B, while bladder anchor 48 remains in the non-radially-expanded deployment configuration, urinary catheter prosthesis 20 is distally advanced in urethra 102 until:

bladder anchor 48 is disposed in bladder 100, distal bladder assembly 32 is disposed in bladder 100 such that urinary inlet 42 is disposed in bladder 100, and proximal intra-urethral assembly 22 is entirely disposed within urethra 102, such that (a) urinary outlet 40, at proximal end 41 of flexible intra-urethral catheter 30, is positioned in urethra 102, and (b) user-activatable hydraulic activator 50, disposed along flexible intra-urethral catheter 30, is positioned within urethra 102.

For some applications, inserting and advancing urinary catheter prosthesis 20 comprises using a guidewire during the insertion for disposing urinary catheter prosthesis 20 entirely within a body of the subject, except for a portion of plug-release line 92, described hereinbelow with reference to FIGS. 1A and 5C.

Figure 5C:
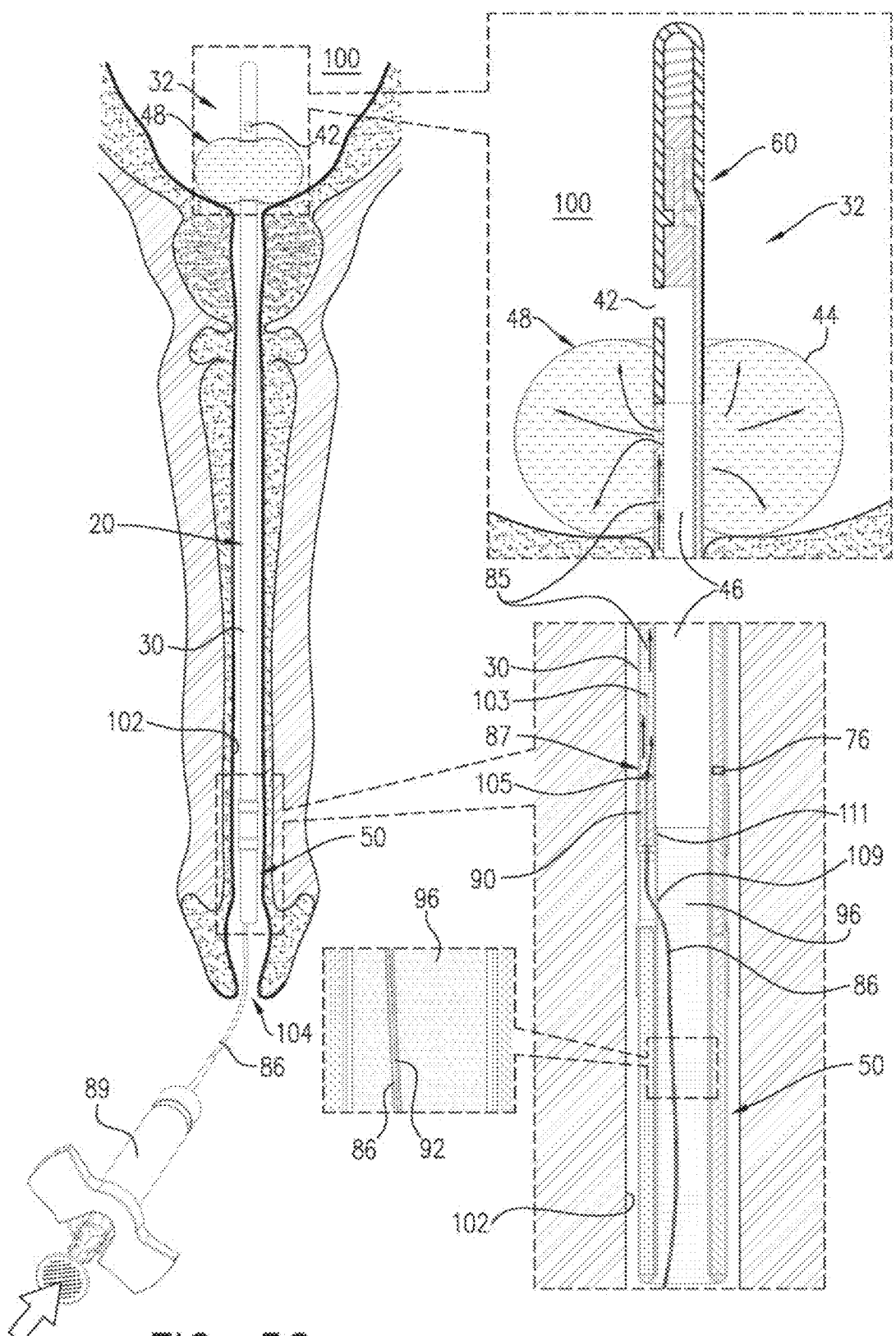
Figure 5D:
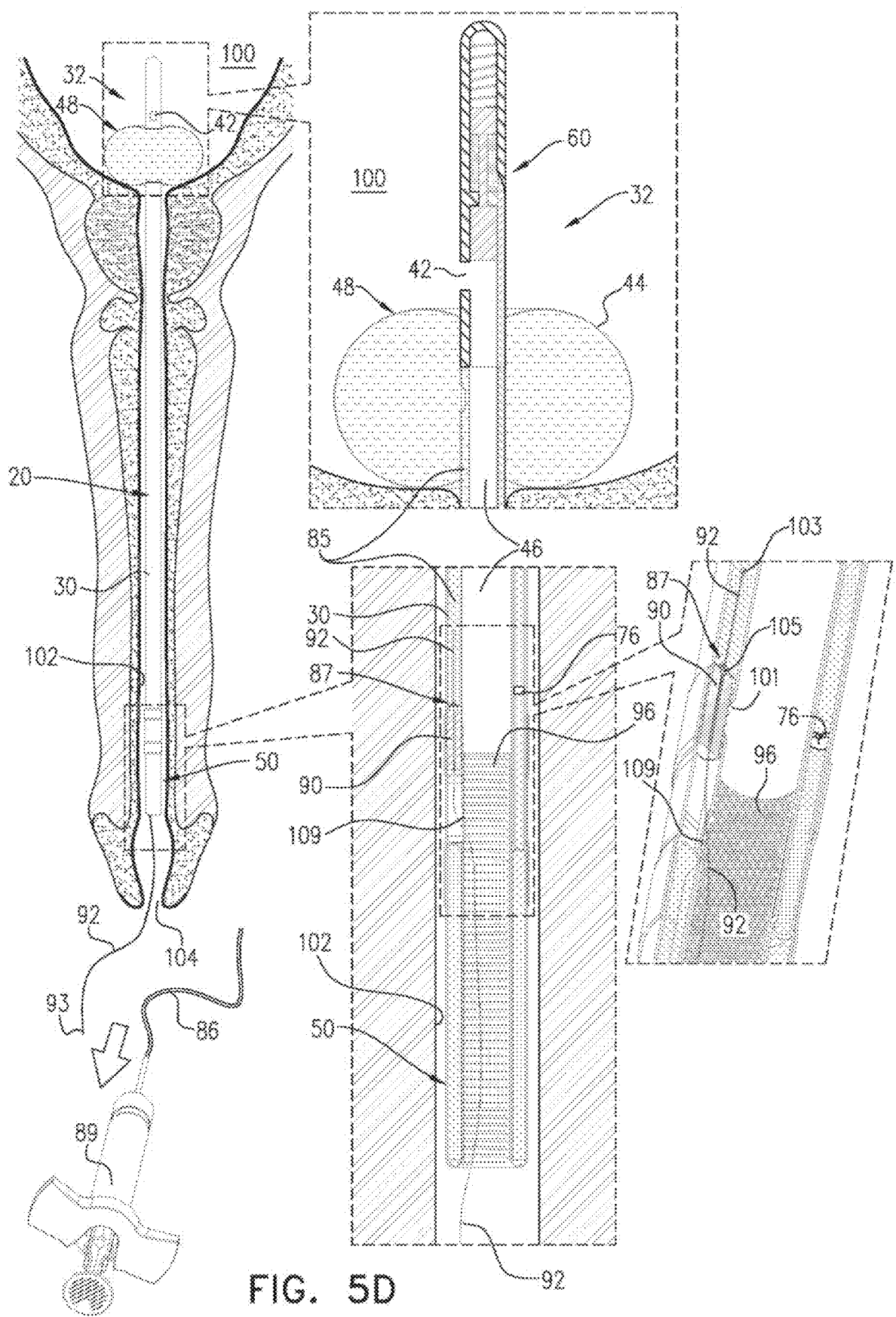

As shown in FIG. 5C, after urinary catheter prosthesis 20 has been inserted and advanced, bladder anchor 48 is transitioned to the deployed configuration in which bladder anchor 48 engages an inner surface 106 of a wall 108 of bladder 100, so as to anchor urinary catheter prosthesis 20 in place, as shown FIG. 5D.

Reference is still made to FIG. 5C, and is additionally again made to FIGS. 1A-B and 2. For some applications in which bladder anchor 48 comprises anchor balloon 44, bladder anchor 48 is transitioned to the deployed configuration by inflating anchor balloon 44 to engage bladder wall 108 around a bladder neck 120. To this end, urinary catheter prosthesis 20 typically comprises a filling channel 85, which runs along a portion of flexible intra-urethral catheter 30 (e.g., within a wall of the portion of flexible intra-urethral catheter 30), and has a distal portion in fluid communication with an interior of anchor balloon 44.

For some applications, such as shown in FIGS. 1A and 5C, anchor balloon 44 is inflated via a filling tube 86 that is removably coupled in fluid communication with a proximal end portion 87 of filling channel 85, using an external fluid source 89, e.g., comprising a syringe. Optionally, filling tube 86 passes through a proximal portion of lumen 46, and optionally extends partially outside flexible intra-urethral catheter 30. For some of these applications, such as shown in FIGS. 1B and 5D, after anchor balloon 44 has been inflated, filling tube 86 is decoupled from the fluid communication with proximal end portion 87 of filling channel 85, and removed from lumen 46 if disposed therein. For example, this decoupling may be performed by proximally pulling on filling tube 86 until it becomes disconnected. Alternatively, for some applications, anchor balloon 44 is inflated via a filling tube 486, such as described hereinbelow with reference to FIGS. 13-15B.

For some applications, such as shown in FIGS. 1A and 5C, when filling tube 86 is removably coupled in the fluid communication with proximal end portion 87 of filling channel 85, a plug-release line 92 passes through a lumen of filling tube 86. For these applications, decoupling filling tube 86 from the fluid communication with proximal end portion 87 of filling channel 85 may comprise proximally pulling filling tube 86 over and off of plug-release line 92. The function of plug-release line 92 is described hereinbelow with reference to FIGS. 5C-F, 1A-B, and 2. Alternatively, for some applications, a plug-release line 492 is provided, such as described hereinabove with reference to FIGS. 13-15B.

As mentioned hereinabove, for some applications hydraulic activator 50 comprises tubular counterforce surface 96 shaped as a tube. For some of these applications, the tube is shaped so as to define a lateral opening 109, and filling tube 86 passes through lateral opening 109 when filling tube 86 is removably coupled in the fluid communication with proximal end portion 87 of filling channel 85, such as shown in FIGS. 1A and 5C.

Reference is made to FIGS. 5C-F, and is additionally again made to FIGS. 1A-B and 2. For some applications, urinary catheter prosthesis 20 further comprises:

an anchor-balloon plug 90, which seals anchor balloon 44 when in a sealed state; and the above-mentioned plug-release line 92, which has a proximal end 93 that is disposed proximally beyond proximal end 41 of flexible intra-urethral catheter 30, and a distal portion that is connected to anchor-balloon plug 90; plug-release line 92 may comprise any elongate flexible member, such as a string, wire, cord, or suture.

Figure 5E:
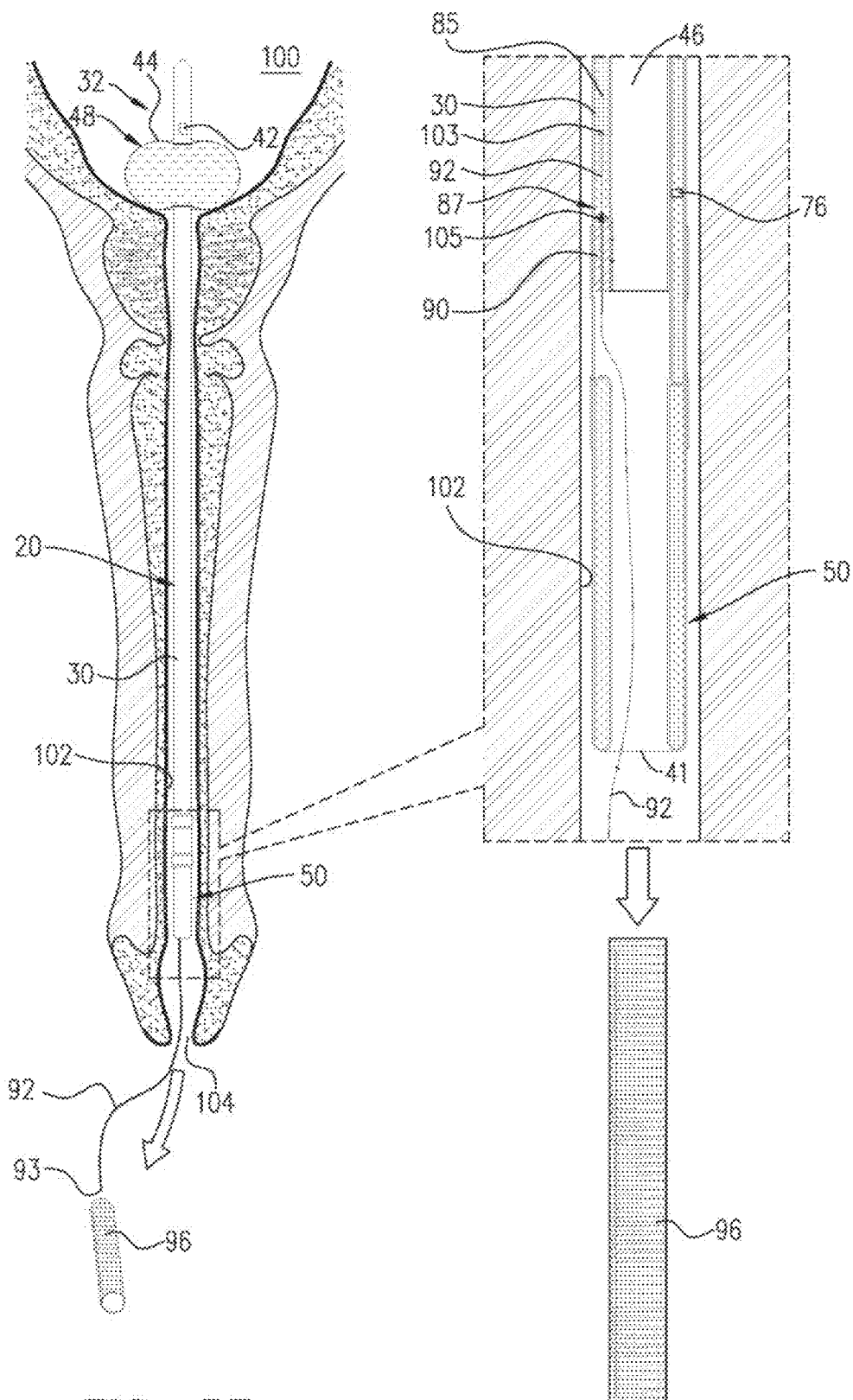
Figure 5F:
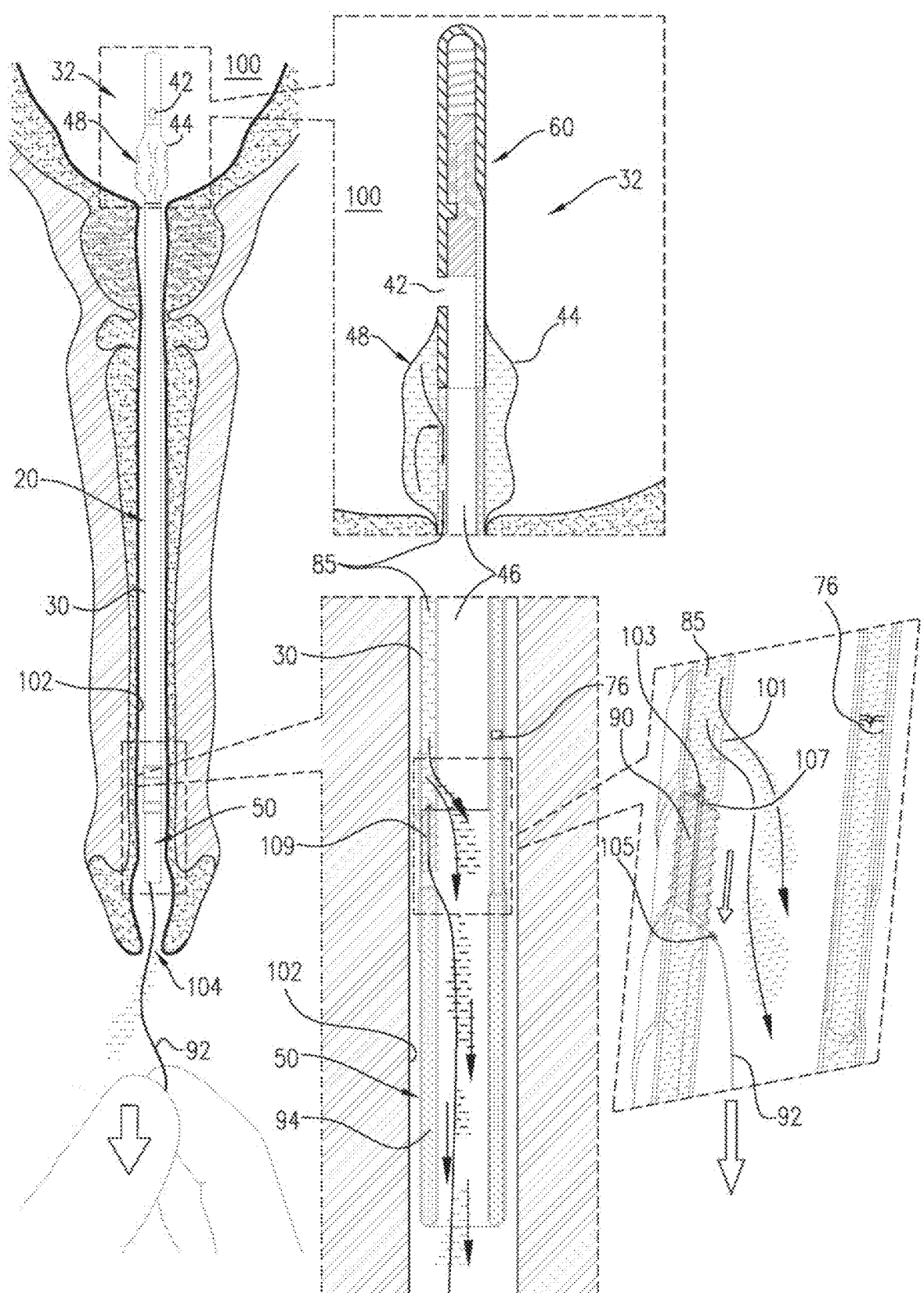
FIGS. 5F-G are schematic illustrations of a technique for removing the urinary catheter prosthesis of FIGS. 1A-B from the subject's body, in the event of a normal removal at the end of the using period or at any time as required by the patient or the clinical staff, in accordance with an application of the present invention.
Figure 5G:
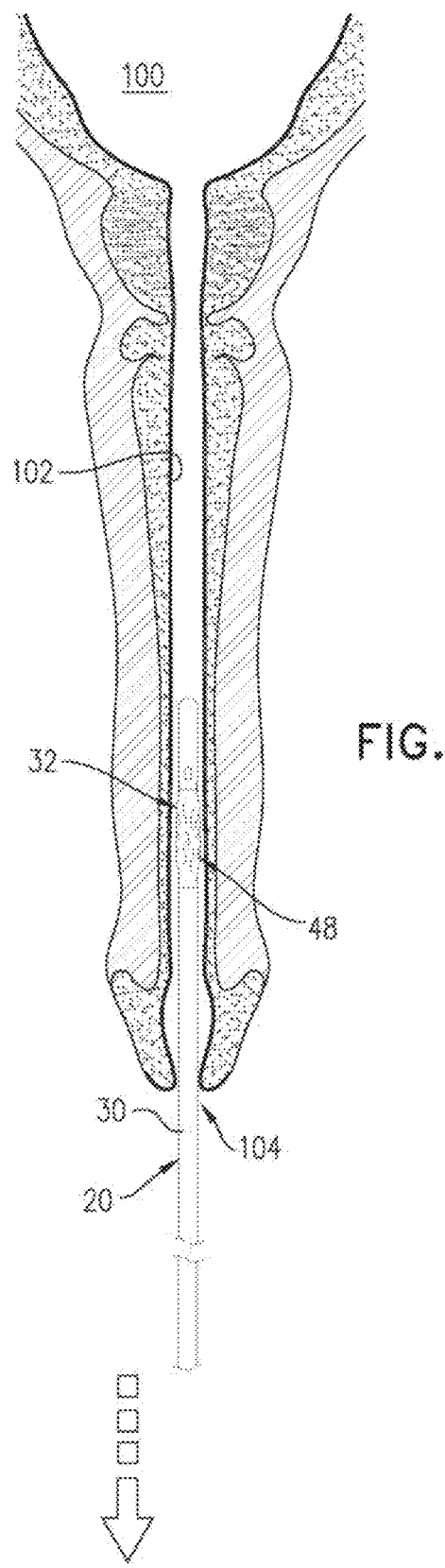

As shown in the transition between FIG. 5E and FIG. 5F, urinary catheter prosthesis 20 is typically inserted into the subject such that proximal end 93 of plug-release line 92 is disposed outside a body of the subject proximally beyond meatus 104 of urethra 102. Typically, the urinary catheter prosthesis is configured to be disposed entirely within a body of the subject, except for a portion of plug-release line 92.

For some applications, also as shown in the transition between FIG. 5E and FIG. 5F, bladder anchor 48 is configured such that proximal pulling on plug-release line 92 transitions anchor-balloon plug 90 from the sealed state to an open state, in which anchor-balloon plug 90 does not seal anchor balloon 44. For some applications, a wall of lumen 46 is shaped so as to define a drainage opening 101 between a proximal portion of filling channel 85 and lumen 46. Anchor-balloon plug 90, when in the sealed state, blocks drainage opening 101. Anchor-balloon plug 90, when in the open state, does not block drainage opening 101, such that there is fluid communication between filling channel 85 and lumen 46.

For some applications, pulling on plug-release line 92 also pulls the entire urinary catheter prosthesis 20 from the bladder and urethra 102, such as shown in FIG. 5G; alternatively, typically in case of disabling to remove urinary catheter prosthesis 20 by pulling the plug-release line 92, urinary catheter prosthesis 20 is withdrawn from urethra 102 using a removal tool, such as removal tool 180, described hereinbelow with reference to FIGS. 6A-C.

For some applications, such as shown in FIG. 1B and the transitions between FIGS. 5E to 5F, pulling on plug-release line 92 pulls anchor-balloon plug 90 proximally by proximally advancing a stopper 103 (which is optionally spherical or semispherical) that is fixed to plug-release line 92 distal to anchor-balloon plug 90 (stopper 103 thus helps connect the distal portion of plug-release line 92 to anchor-balloon plug 90). Urinary catheter prosthesis 20 is configured such that stopper 103 cannot pass into a distal end of channel defined through a body of anchor-balloon plug 90, such that proximal pulling on the stopper via the plug-release line proximally pulls the anchor-balloon plug. Optionally, urinary catheter prosthesis 20 further comprises a stopper stop 107, which is disposed along plug-release line 92 between stopper 103 and the distal end of anchor-balloon plug 90, and prevents stopper 103 from passing into the distal end of the channel defined through the body of anchor-balloon plug 90.

As mentioned hereinabove, for some applications hydraulic activator 50 comprises tubular counterforce surface 96 shaped as a tube. For some of these applications, such as shown in FIGS. 1A-B and 5C-D, when anchor-balloon plug 90 is in the sealed state, a distal portion 111 of the tube applies a radially-outward force against anchor-balloon plug 90, helping hold anchor-balloon plug 90 in place by friction. For some of these applications, before anchor-balloon plug 90 is transitioned from the sealed state to the open state by proximal pulling on plug-release line 92, tubular counterforce surface 96 is pulled out of flexible intra-urethral catheter 30 via proximal end 41 thereof, as shown in FIGS. 5E and 5F by releasing hydraulic liquid 70 from anchor balloon 44 through drainage opening 101 into lumen 46.

Reference is again made to FIGS. 1A and 5C. For some applications, during inflation of anchor balloon 44, the inflation fluid passes through a channel defined through a body of anchor-balloon plug 90 to proximal end portion 87 of filling channel 85. Optionally, urinary catheter prosthesis 20 further comprises a one-way valve, which is initially disposed at a distal end of the channel of anchor-balloon plug 90, and is configured to allow unidirectional flow of the inflation fluid in a distal direction, while inhibiting (typically, preventing) flow of the inflation fluid in a proximal direction. For example, the one-way valve may comprise a small stopper 105 (which is optionally spherical or semi-spherical) and an indented distal surface of anchor-balloon plug 90, with which stopper 105 forms a liquid-tight seal when disposed therein and pulled slightly proximally. Optionally, stopper 105 is axially fixed to plug-release line 92. Alternatively, the one-way valve comprises another type of one-way valve that is known in the valve art.

Figures 6A, 6B, 6C:
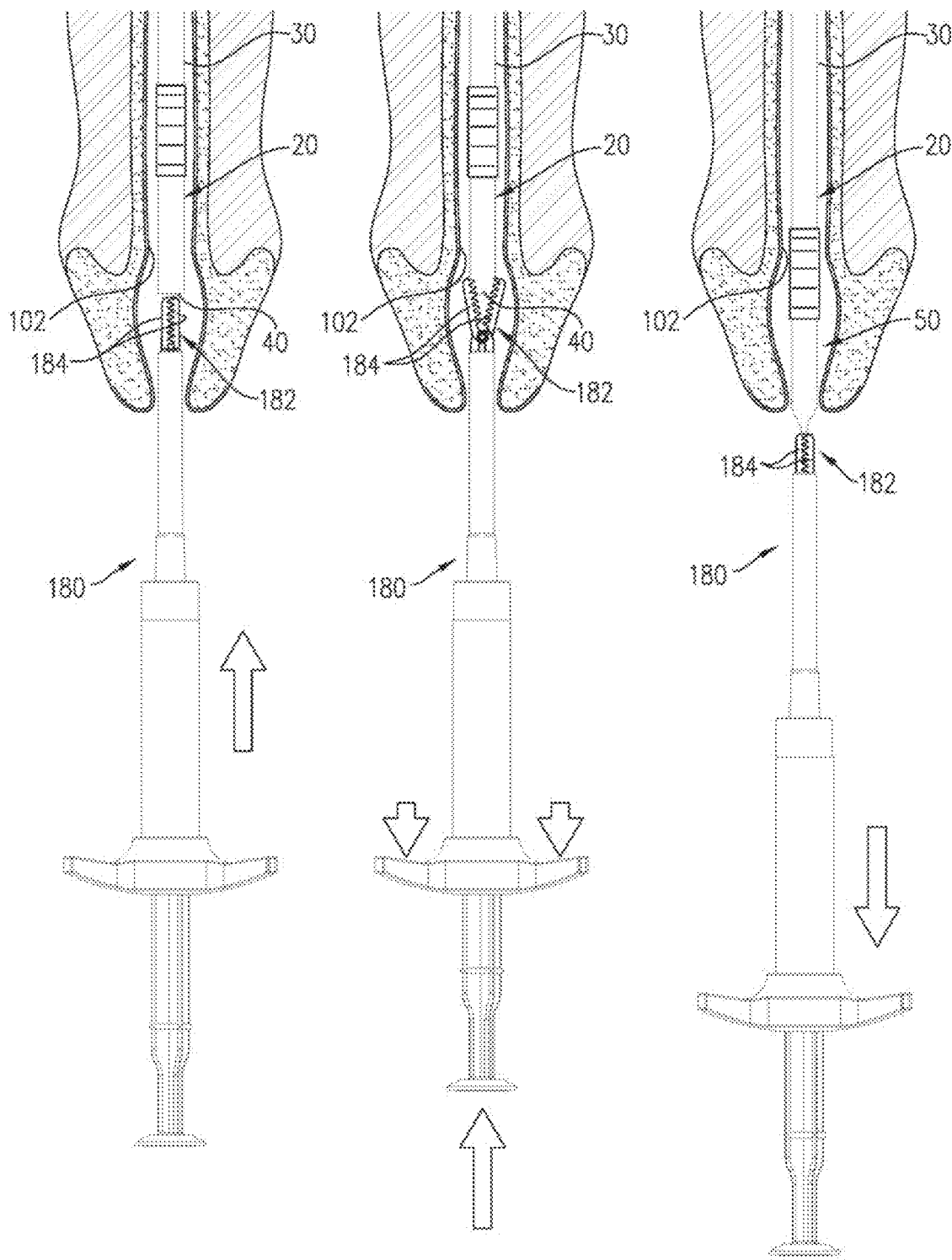
FIGS. 6A-C are schematic illustrations of an alternative technique for removing the urinary catheter prosthesis of FIGS. 1A-B from the subject's body, in the event of a failure of the removal techniques described with reference to FIGS. 5F-G and 15A-B, in accordance with an application of the present invention.

Reference is made to FIGS. 6A-C, which are schematic illustrations of an alternative technique for removing urinary catheter prosthesis 20 from the subject's body in the event of a failure of the removal technique described hereinabove with reference to FIGS. 5E-G, in accordance with an application of the present invention. This alternative technique may also be used for removing urinary catheter prosthesis 20 from the subject's body in the event of a failure of the removal technique described hereinbelow with reference to FIGS. 13-15B. Of course, other techniques may be used for removing the prosthesis.

A removal tool 180 is provided, which comprises a gripper 182, e.g., comprising two jaws 184, similar to conventional tweezers. Gripper 182 is inserted partially into urethra 102 and used to catch a proximal portion of flexible intra-urethral catheter 30 in urethra 102.

In an application of the present invention, another user-controllable urinary catheter prosthesis is provided for minimally-invasive insertion into a subject. Other than as described below, the urinary catheter prosthesis is generally similar to urinary catheter prosthesis 20, described hereinabove with reference to FIGS. 1A-6C, and may implement any of the feature thereof. The urinary catheter prosthesis comprises a bladder anchor that comprises an umbrella anchor, which comprises a plurality of ribs that are configured to engage bladder wall 108 around bladder neck 120 when the umbrella anchor is in the deployed configuration.

In an application of the present invention, yet another user-controllable urinary catheter prosthesis is provided for minimally-invasive insertion into a subject, in accordance with an application of the present invention. Other than as described below, the urinary catheter prosthesis is generally similar to urinary catheter prosthesis 20, described hereinabove with reference to FIGS. 1A-6C, and may implement any of the feature thereof. The urinary catheter prosthesis comprises a bladder anchor that comprises a plurality of flexible petals that are configured to engage bladder wall 108 around bladder neck 120 when the bladder anchor is in the deployed configuration.

Figure 7A:
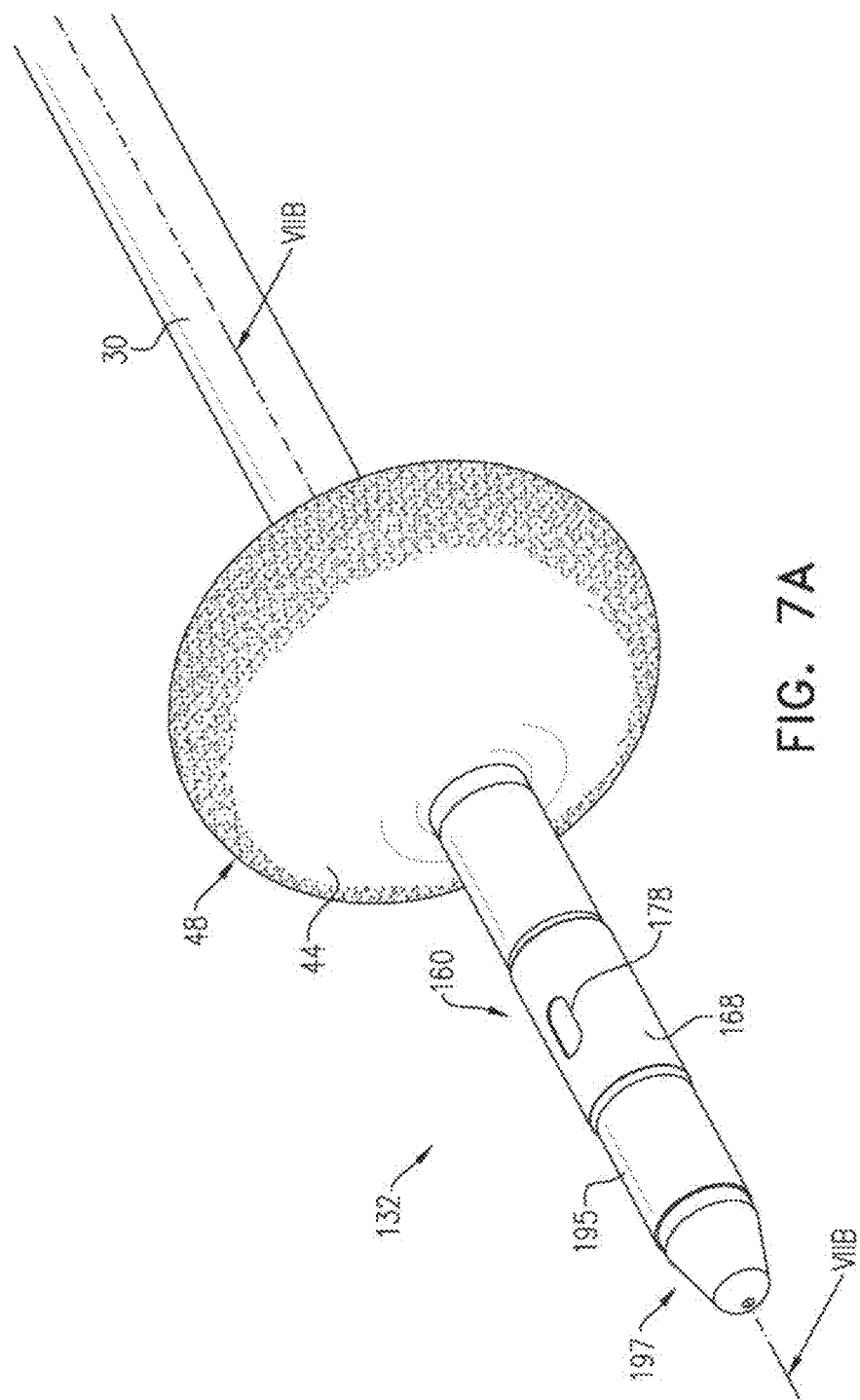

Reference is now made to FIGS. 7A and 7B, which are a schematic illustration and a schematic cross-sectional illustration of a distal bladder assembly 132, taken along a line VIIB-VIIB of FIG. 7A, with a hydraulic valve 160 thereof in a closed resting state, in accordance with an application of the present invention.

Figure 8A:
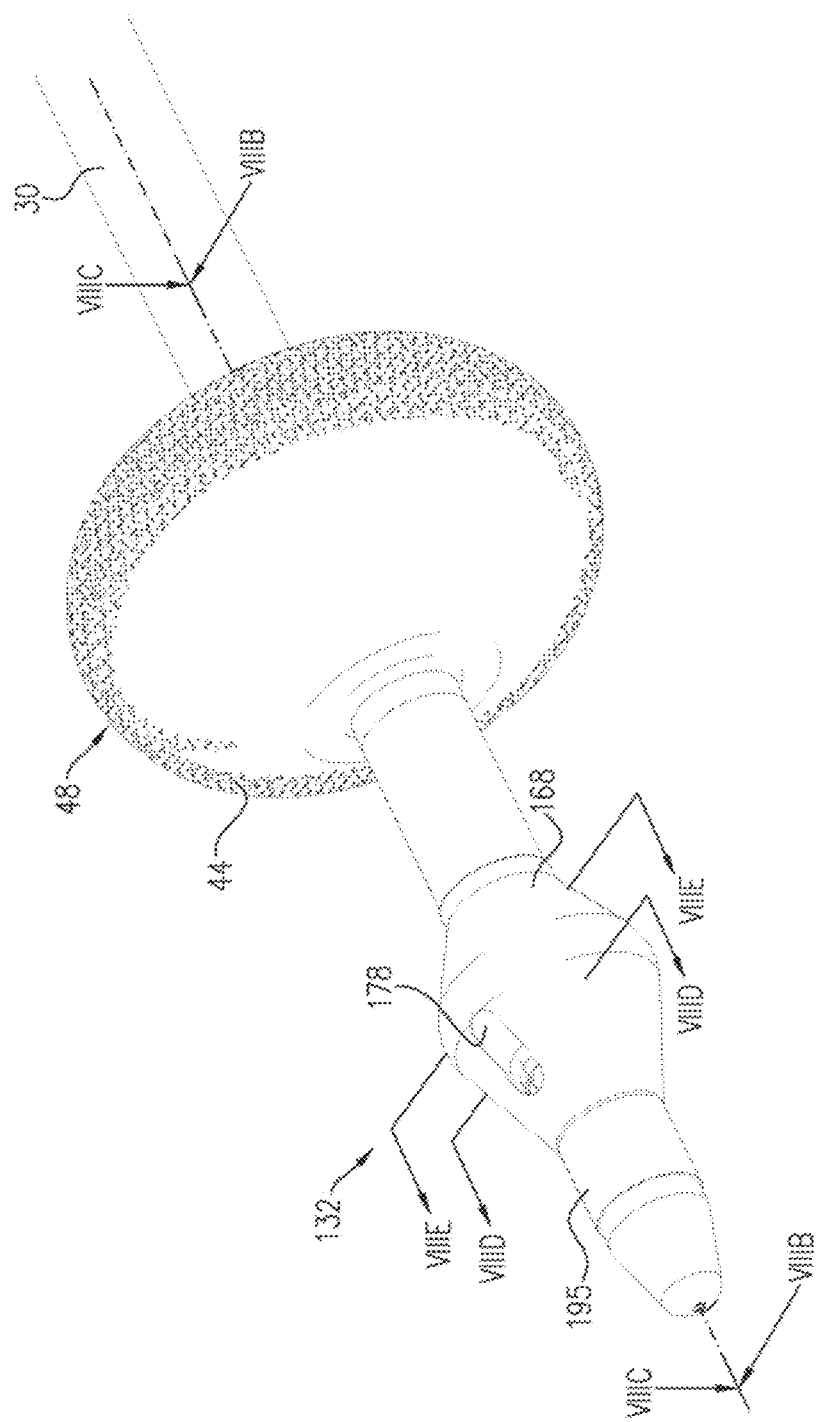

Reference is further made to FIGS. 8A and 8B-E, which are a schematic illustration and schematic cross-sectional illustrations of distal bladder assembly 132, taken along lines VIIIB-VIIIB, VIIIC-VIIIC, VIIID-VIIID, and VIIIE-VIIIE of FIG. 8A, respectively, with hydraulic valve 160 in an open state, in accordance with an application of the present invention.

In some applications of the present invention, urinary catheter prosthesis 20, described hereinabove with reference to FIGS. 1A-6C, comprises distal bladder assembly 132, rather than distal bladder assembly 32. Other than as described hereinbelow, distal bladder assembly 132 is similar to distal bladder assembly 32, and may implement any of the features thereof, mutatis mutandis. Like reference numerals refer to like parts.

Hydraulic valve 160 of distal bladder assembly 132 comprises a valve balloon 164. Upon inflation of valve balloon 164, such as shown in FIGS. 8A-E, hydraulic valve 160 is configured to assume the open state, in which hydraulic valve 160 allows urine flow between urinary inlet 42 and urinary outlet 40 (i.e., allows urination). When valve balloon 164 is not inflated (either before inflation of valve balloon 164 or after subsequent deflation thereof), such as shown in FIGS. 7A-B, hydraulic valve 160 is in the closed resting state, in which hydraulic valve 160 entirely blocks urine from entering urinary inlet 42, flowing through lumen 46, and exiting urinary outlet 40. Urinary catheter prosthesis 20 thus blocks urination and leakage of urine from the subject's bladder via lumen 46 when hydraulic valve 160 is in its closed resting state.

As described above with reference to FIGS. 1A-B and 2, for some applications, hydraulic activator 50 comprises control balloon 94 and urinary catheter prosthesis 20 comprises hydraulic tube 74. For applications in which urinary catheter prosthesis 20 comprises distal bladder assembly 132:

hydraulic tube 74 couples control balloon 94 in hydraulic communication with valve balloon 164, and control balloon 94 is configured, upon squeezing thereof, to inflate valve balloon 164, thereby transitioning hydraulic valve 160 from the closed resting state to the open state.

For some applications, a distal portion of distal bladder assembly 132 comprises a tubular casing 191, which may implement any of the features of tubular casing 91, described hereinabove with reference to FIGS. 1A-B and 2. Tubular casing 191 is shaped so as to define urinary inlet 42 through tubular casing 191 at an axial position 166 along tubular casing 191. As described hereinabove with reference to FIGS. 1A-B and 2, urinary inlet 42 may comprise a single urinary inlet 42 or a plurality of urinary inlets 42; in the latter case, urinary inlets 42 may be located at the same axial position 166 (such as shown) or at respective different axial positions 166 (configuration not shown).

For some of these applications, hydraulic valve 160 further comprises an elastic sleeve 168, which (a) defines one or more openings 178 through elastic sleeve 168, (b) is sealingly coupled to tubular casing 191, and (c) surrounds tubular casing 191, including at axial position 166 of urinary inlet 42. Hydraulic valve 160 is configured such that when it is in the closed resting state, such as shown in FIGS. 7A-B, elastic sleeve 168 entirely occludes urinary inlet 42. Hydraulic valve 160 is configured to assume the open state, such as shown in FIGS. 8A-E, when elastic valve balloon 164 is inflated sufficiently to radially expand elastic sleeve 168 such that elastic sleeve 168 (a) does not occlude urinary inlet 42 and (b) defines a fluid flow path 179 between (i) the one or more openings 178 through elastic sleeve 168 and (ii) urinary inlet 42, such as highly schematically indicated in FIG. 8C.

Typically, elastic sleeve 168 is configured to:
store elastic energy during transitioning of hydraulic valve 160 from the closed resting state to the open state upon radial expansion of elastic sleeve 168, upon inflation of elastic valve balloon 164, and
help automatically transition hydraulic valve 160 to the closed resting state by releasing the elastic energy as elastic sleeve 168 radially contracts, upon deflation of elastic valve balloon 164.

Figure 8B:
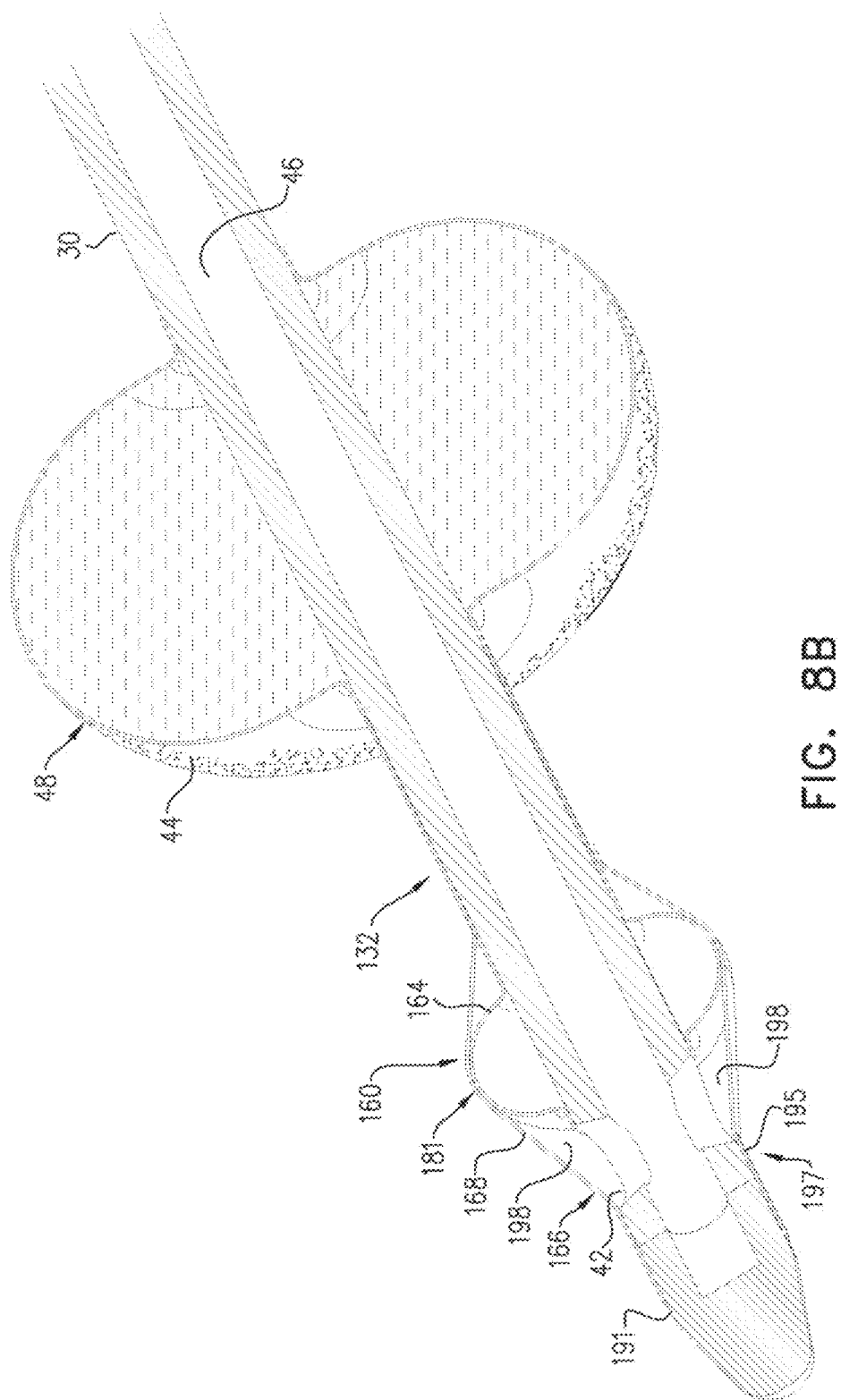

For some applications, (a) an axial position 181 of valve balloon 164 along distal bladder assembly 132 is at least partially non-axially-overlapping with (b) axial position 166 of urinary inlet 42, such as shown in FIGS. 8B and 8C. Typically, axial position 181 of valve balloon 164 is proximal to axial position 166 of urinary inlet 42, such as shown in FIGS. 8B and 8C. In some configurations in which urinary inlet 42 comprises a plurality of urinary inlets 42, axial position 181 of valve balloon 164 is at least partially non-axially-overlapping with (typically, proximal to) respective axial positions 166 of urinary inlets 42, such as shown in FIGS. 8B and 8C.

Figure 8E:
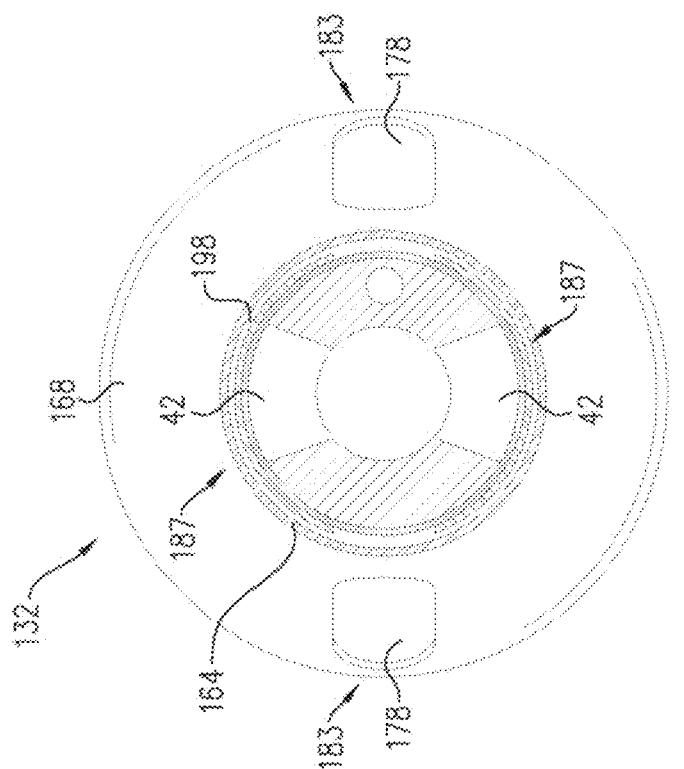
Figure 8D:
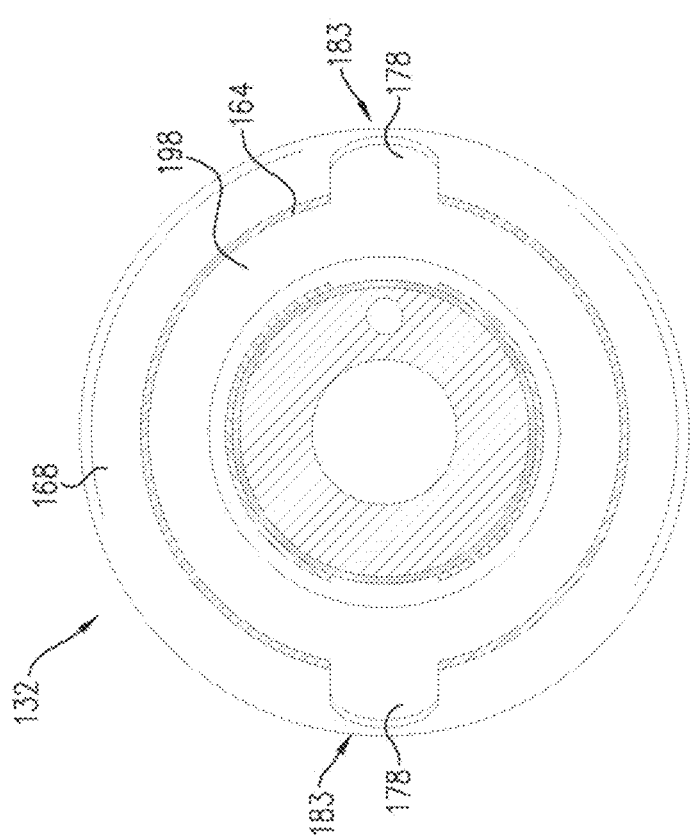

For some applications, such as labeled in FIGS. 8D and 8E, the one or more openings 178 through elastic sleeve 168 are located at respective radial positions 183 around tubular casing 191 that are entirely non-radially-overlapping with a radial position 187 of urinary inlet 42 around tubular casing 191. In some configurations in which urinary inlet 42 comprises a plurality of urinary inlets 42, radial positions 183 are entirely non-radially-overlapping with respective radial positions 187 of urinary inlets 42 around tubular casing 191. Optionally, in some configurations in which the one or more openings 178 comprise two opening 178 and urinary inlet 42 comprises two urinary inlets 42, the respective radial positions 183 of openings 178 are radially offset by 90 degrees from the respective radial positions 187 of urinary inlets 42. (As used in the present application, including in the claims and Inventive Concepts, a "radial position" around tubular casing 191 refers to an "o'clock" around tubular casing 191.)

Typically, a distal axial end portion 195 of elastic sleeve 168 is sealingly coupled to tubular casing 191 at an axial position 197 along tubular casing 191 that is distal to axial position 166 of urinary inlet 42, such that upon inflation of valve balloon 164, elastic sleeve 168 expands so as to form a pocket 198 between elastic sleeve 168 and tubular casing 191, such as shown in FIGS. 8B, 8C, 8D, and 8E. Pocket 198 provides above-mentioned fluid flow path 179 between the one or more openings 178 and urinary inlet 42, labeled in FIG. 8C.

Reference is now made to FIGS. 9A and 9B, which are a schematic illustration and a schematic cross-sectional illustration of a distal bladder assembly 232, taken along a line IXB-IXB of FIG. 9A, with a hydraulic valve 260 thereof in a closed resting state, in accordance with an application of the present invention.

Figure 10A:
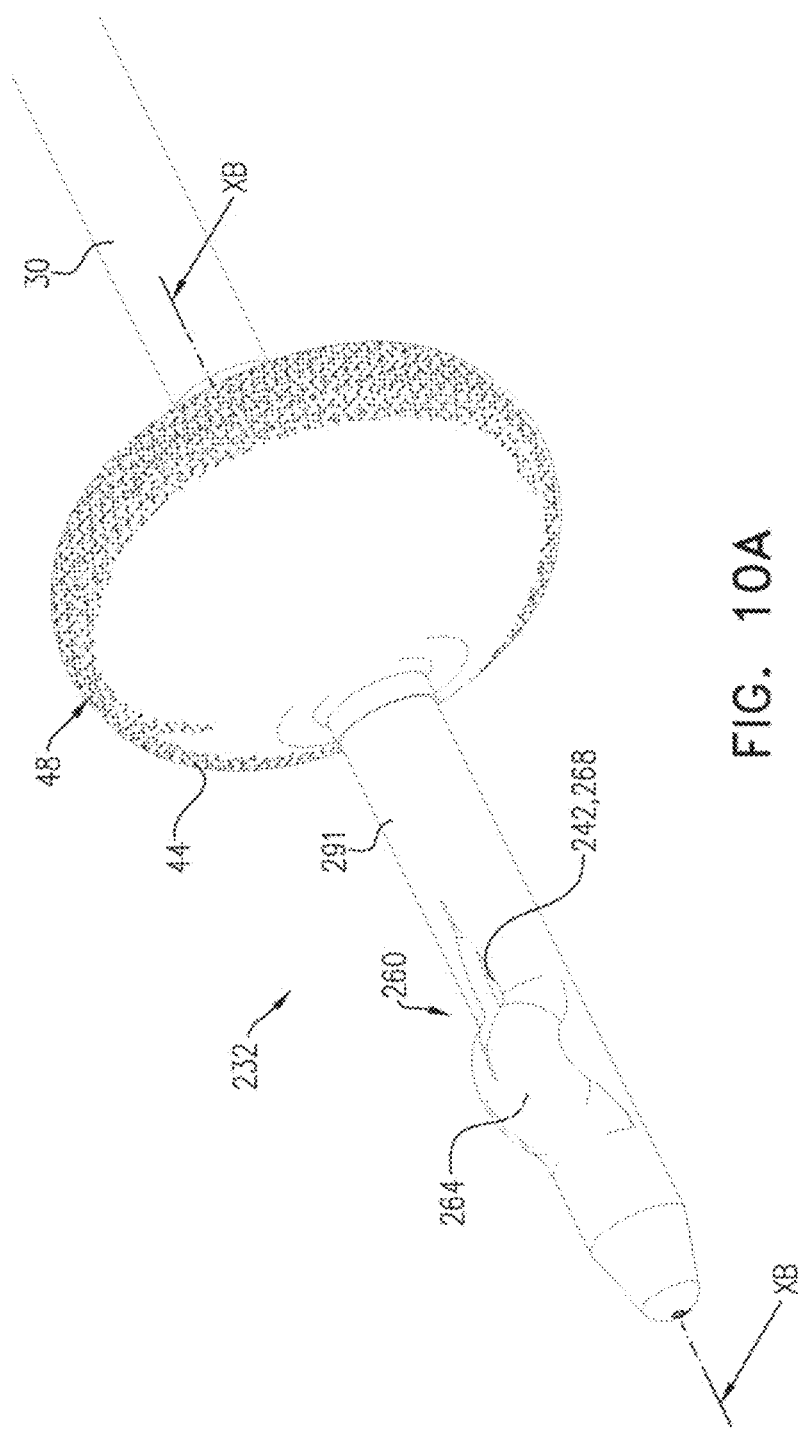
FIGS. 10A and 10B are a schematic illustration and a schematic cross-sectional illustration of the distal bladder assembly of FIGS. 9A-B, taken along a line XB-XB of FIG. 10A, with the hydraulic valve of FIGS. 9A-B in an open state, in accordance with an application of the present invention.
Figure 10B:
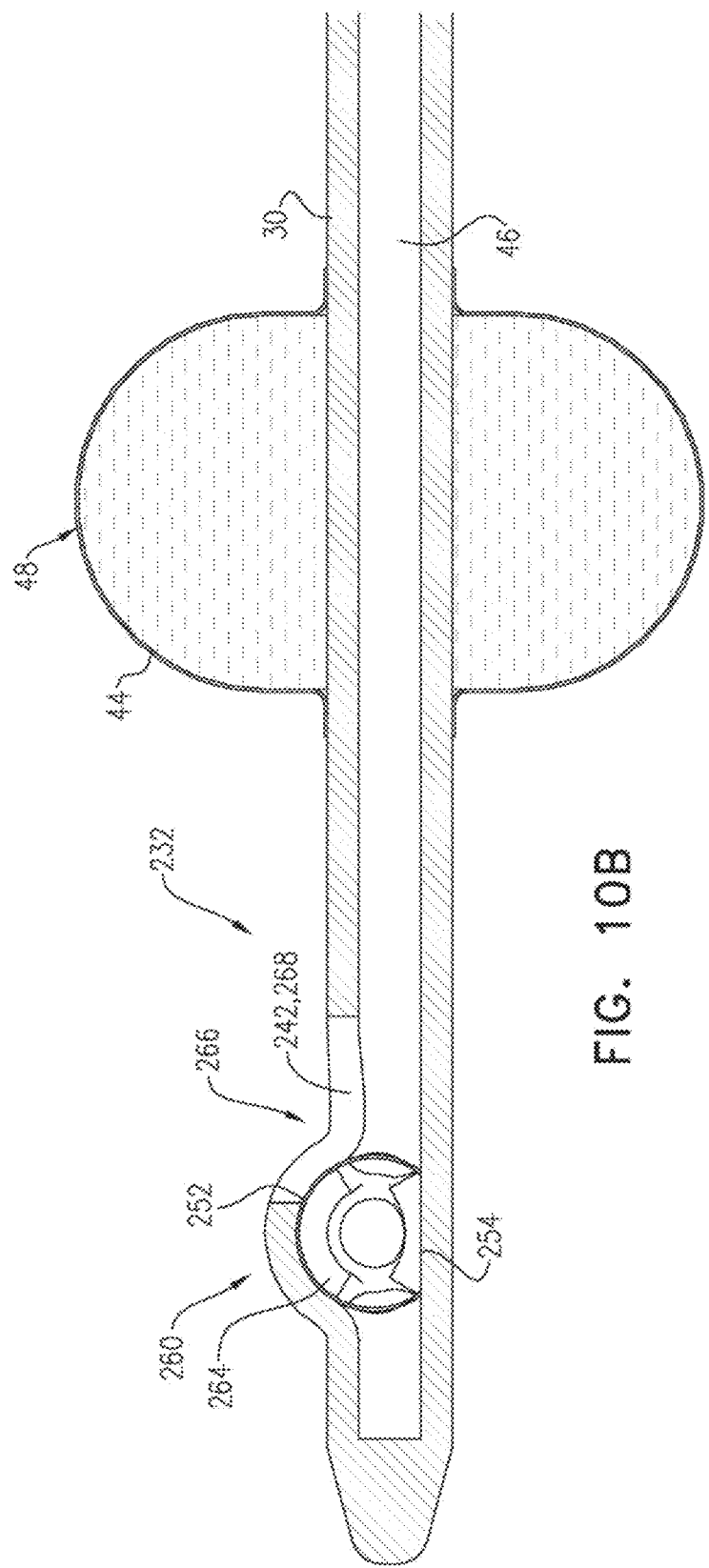

Reference is further made to FIGS. 10A and 10B, which are a schematic illustration and a schematic cross-sectional illustration of distal bladder assembly 232, taken along a line XB-XB of FIG. 10A, with hydraulic valve 260 in an open state, in accordance with an application of the present invention.

In some applications of the present invention, urinary catheter prosthesis 20, described hereinabove with reference to FIGS. 1A-6C, comprises distal bladder assembly 232, rather than distal bladder assembly 32. Other than as described hereinbelow, distal bladder assembly 232 is similar to distal bladder assembly 32, and may implement any of the features thereof, mutatis mutandis. Like reference numerals refer to like parts.

Hydraulic valve 260 of distal bladder assembly 232 comprises a valve balloon 264 and a urinary inlet 242. Distal bladder assembly 232 is configured to be disposed, by insertion via urethra 102, in the bladder of the subject such that urinary inlet 242 is disposed in the bladder of the subject. Lumen of urinary catheter prosthesis 20 defines the urine path between urinary inlet 242 and urinary outlet 40. Urinary inlet 242 may comprise a single urinary inlet 242 or a plurality of urinary inlets 242.

Upon inflation of valve balloon 264, such as shown in FIGS. 10A-B, hydraulic valve 260 is configured to assume the open state, in which hydraulic valve 260 allows urine flow between urinary inlet 242 and urinary outlet 40 (i.e., allows urination). When valve balloon 264 is not inflated (either before inflation of valve balloon 264 or after subsequent deflation thereof), such as shown in FIGS. 9A-B, hydraulic valve 260 is in the closed resting state, in which hydraulic valve 260 entirely blocks urine from entering urinary inlet 242, flowing through lumen 46, and exiting urinary outlet 40. Urinary catheter prosthesis 20 thus blocks urination and leakage of urine from the subject's bladder via lumen 46 when hydraulic valve 260 is in its closed resting state.

As described hereinabove with reference to FIGS. 1A-B and 2, for some applications, hydraulic activator 50 comprises control balloon 94 and urinary catheter prosthesis 20 comprises hydraulic tube 74. For applications in which urinary catheter prosthesis 20 comprises distal bladder assembly 232:
hydraulic tube 74 couples control balloon 94 in hydraulic communication with valve balloon 264, and
control balloon 94 is configured, upon squeezing thereof, to inflate valve balloon 264, thereby transitioning hydraulic valve 260 from the closed resting state to the open state.

For some applications, a distal portion of distal bladder assembly 232 comprises a tubular casing 291, which may implement any of the features of tubular casing 91, described hereinabove with reference to FIGS. 1A-B and 2. Tubular casing 291 is shaped so as to define urinary inlet 242 through tubular casing 291 at an axial position 266 along tubular casing 291. As described above, urinary inlet 242 may comprise a single urinary inlet 242 (such as shown) or a plurality of urinary inlets 242; in the latter case, the urinary inlets 242 may be located at the same axial position 266 or at respective different axial positions 266.

Distal bladder assembly 232 is configured such that urinary inlet 242 is closed when hydraulic valve 260 is in the closed resting state, such as shown in FIGS. 9A-B, and hydraulic valve 260 is configured to assume the open state when valve balloon 264 is inflated sufficiently to open urinary inlet 242, such as shown in FIGS. 10A-B.

For some applications, urinary inlet 242 is shaped so as to define one or more slits 268, such as exactly one slit 268 (as shown) or two or more slits 268 (configuration not shown), which are closed when hydraulic valve 260 is in the closed resting state, such as shown in FIGS. 9A-B. Hydraulic valve 260 is configured to assume the open state when valve balloon 264 is inflated sufficiently to push open the one or more slits 268, such as shown in FIGS. 9A-B. In configurations in which urinary inlet 242 is shaped so as to define two or more slits 268, the slits may be oriented in the same or different directions (e.g., in an "x" orientation).

In order to maintain hydraulic valve 260 in the closed resting state when valve balloon 264 is not inflated, urinary inlet 242 (e.g., the one or more slits 268) are configured such that the natural pressure gradient between the bladder of the subject and lumen 46 of urinary catheter prosthesis 20 is insufficient to open urinary inlet 242.

For some applications, (a) an axial position 281 of valve balloon 264 along distal bladder assembly 232 and (b) axial position 266 of urinary inlet 242 (e.g., the one or more slits 268) are at least partially non-axially-overlapping with each other, such as shown. Typically, axial position 281 of valve balloon 264 is at least partially distal to axial position 266 of urinary inlet 242 (e.g., the one or more slits 268), such as shown. Optionally, in addition, axial position 281 and axial position 266 are partially axially-overlapping with each other, at least when valve balloon 264 is inflated, such as shown in FIGS. 10A-B.

Reference is again made to FIG. 10B. For some applications, valve balloon 264 is shaped generally as an oblate spheroid 252 (such as similar to a lentil) lacking a three-dimension segment on one side 254. (A three-dimensional segment is analogous to a two-dimensional segment of a circle, as is known in geometry.) An outer perimeter of a projection of oblate spheroid 252 onto a plane generally has the shape of a circle lacking a segment on one side (i.e., the one side coincides with a chord of the lacking segment). Typically, the one side 254 is oriented parallel to a central longitudinal axis of tubular casing 291, and contacts an inner wall of tubular casing 291 on a side of the inner wall opposite the side of the inner wall that is shaped so as to define the one or more slits 268.

For other applications, valve balloon 264 has another shape, such as a sphere or a complete oblate.

Figure 11A:
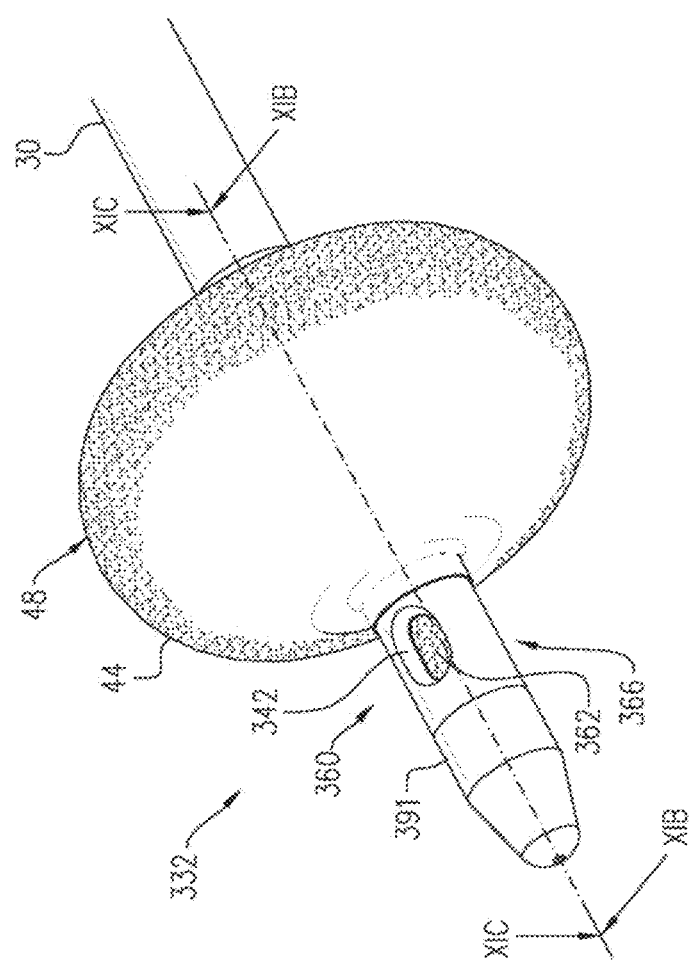

Reference is now made to FIGS. 11A and 11B-C, which are a schematic illustration and schematic cross-sectional illustrations of a distal bladder assembly 332, taken along lines XIB-XIB and XIC-XIC of FIG. 11A, respectively, with a hydraulic valve 360 thereof in a closed resting state, in accordance with an application of the present invention.

Figure 12A:
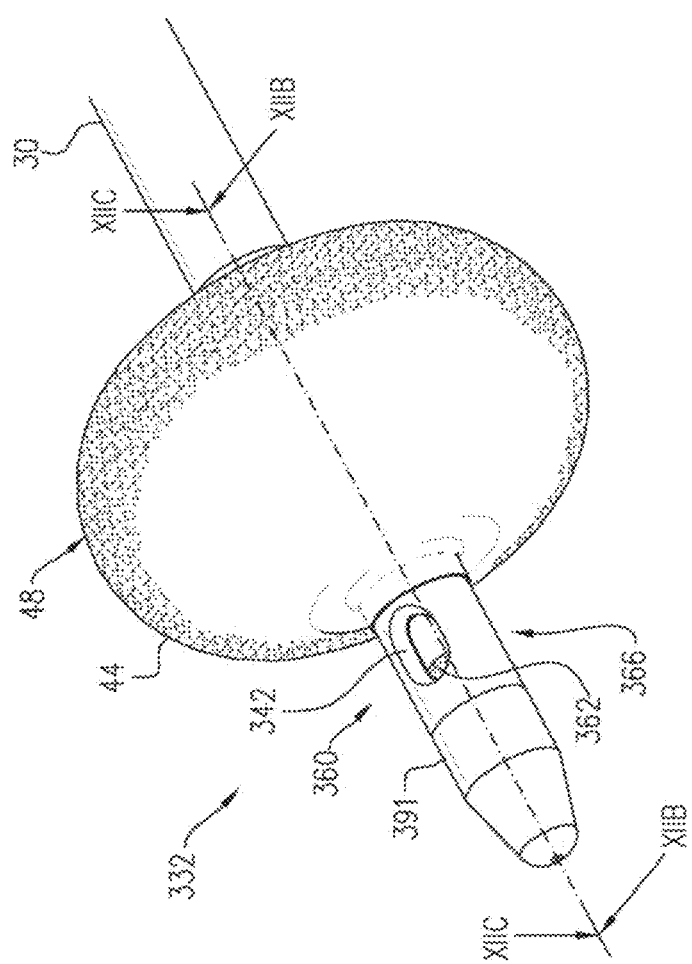

Reference is further made to FIGS. 12A and 12B-C, which are a schematic illustration and schematic cross-sectional illustrations of distal bladder assembly 332, taken along lines XIIB-XIIB and XIIC-XIIC of FIG. 12A, respectively, with hydraulic valve 360 in an open state, in accordance with an application of the present invention.

In some applications of the present invention, urinary catheter prosthesis 20, described hereinabove with reference to FIGS. 1A-6C, comprises distal bladder assembly 332, rather than distal bladder assembly 32. Other than as described hereinbelow, distal bladder assembly 332 is similar to distal bladder assembly 32, and may implement any of the features thereof, mutatis mutandis. Like reference numerals refer to like parts.

Hydraulic valve 360 of distal bladder assembly 332 comprises a valve balloon 364. Upon inflation of valve balloon 364, such as shown in FIGS. 12A-C, hydraulic valve 360 is configured to assume the open state, in which hydraulic valve 360 allows urine flow between (a) a urinary inlet 342 defined by distal bladder assembly 332 and (b) urinary outlet 40 (i.e., allows urination). Urinary inlet 342 may comprise a single urinary inlet 342 or a plurality of urinary inlets 342 (such as shown). When valve balloon 364 is not inflated (either before inflation of valve balloon 364 or after subsequent deflation thereof), such as shown in FIGS. 11A-C, hydraulic valve 360 is in the closed resting state, in which hydraulic valve 360 entirely blocks urine from entering urinary inlet 342, flowing through lumen 46, and exiting urinary outlet 40. Urinary catheter prosthesis 20 thus blocks urination and leakage of urine from the subject's bladder via lumen 46 when hydraulic valve 360 is in its closed resting state.

As described above with reference to FIGS. 1A-B and 2, for some applications, hydraulic activator 50 comprises control balloon 94 and urinary catheter prosthesis 20 comprises hydraulic tube 74. For applications in which urinary catheter prosthesis 20 comprises distal bladder assembly 332:

hydraulic tube 74 couples control balloon 94 in hydraulic communication with valve balloon 364, and control balloon 94 is configured, upon squeezing thereof, to inflate valve balloon 364, thereby transitioning hydraulic valve 360 from the closed resting state to the open state.

Hydraulic valve 360 further comprises a valve plug 362, which is attached to valve balloon 364. Valve plug 362 is configured to occlude urinary inlet 342 when hydraulic valve 360 is in the closed resting state, such as shown in FIGS. 11A-C. Hydraulic valve 360 is configured such that the inflation of valve balloon 364 moves the valve plug away from urinary inlet 342 (such as in a distal direction), thereby transitioning hydraulic valve 360 to the open state, such as shown in FIGS. 12A-C.

Typically, valve plug 362 is non-inflatable, although it may be inflatable.

For some applications, valve plug 362 comprises stainless steel, medical grade polypropylene, or medical grade polycarbonate.

For some applications, a distal portion of distal bladder assembly 332 comprises a tubular casing 391, which may implement any of the features of tubular casing 91, described hereinabove with reference to FIGS. 1A-B and 2. Tubular casing 391 is shaped so as to define urinary inlet 342 through tubular casing 391 at an axial position 366 along tubular casing 391. As described above, urinary inlet 342 may comprise a single urinary inlet 342 or a plurality of urinary inlets 342 (such as shown); in the latter case, the urinary inlets 342 may be located at the same axial position 366 or at respective different axial positions 366.

For some applications, (a) an axial position 381 of valve balloon 364 along distal bladder assembly 332 and (b) axial position 366 of urinary inlet 342 are at least partially non-axially-overlapping with each other, such as entirely non-axially-overlapping with each other, such as shown. Typically, axial position 381 of valve balloon 364 is at least partially distal to axial position 366 of urinary inlet 342, such as entirely distal to axial position 366 of urinary inlet 342, as shown.

Reference is now made to FIGS. 7A-8E, 9A-10B, and 11A-12C. For some applications, valve balloon 164, 264, or 364 is elastic, and is configured to:

store elastic energy during transitioning of hydraulic valve 160, 260, or 360, respectively, from the closed resting state to the open state upon inflation of the elastic valve balloon, and automatically transition the hydraulic valve to the closed resting state by releasing the elastic energy as the elastic valve balloon deflates.

For some of these applications, valve balloon 164, 264, or 364 is configured to have an elasticity that automatically transitions the hydraulic valve to the closed state by releasing the elastic energy over a set amount of time after being transitioned to the open state. For example, the set amount of time may have a value that falls in the range of 15 to 360 seconds, e.g., in the range of 20 to 240 second, such as in the range of 60 to 120 seconds, such as 240 second, e.g., 120 seconds, such as 60 seconds or 30 seconds.

As described hereinabove with reference to FIGS. 1A-B and 2, for some applications, the hydraulic valve further comprises hydraulic semi-one-way shutter 76 that is configured to delay return of hydraulic liquid 70 from the hydraulic valve to hydraulic activator 50. In hydraulic valve 160, 260, or 360, hydraulic semi-one-way shutter 76 delays valve balloon 164, 264, or 364 from automatically transitioning from the open state to the closed resting state, such that the hydraulic valve assumes the closed resting state the set amount of time after being transitioned to the open state. For applications in which valve balloon 164, 264, or 364 is elastic, the combination of the elasticity of the valve balloon and hydraulic semi-one-way shutter 76 sets the amount of time between the transition to the open state and the return transition to the closed state.

Figure 13:
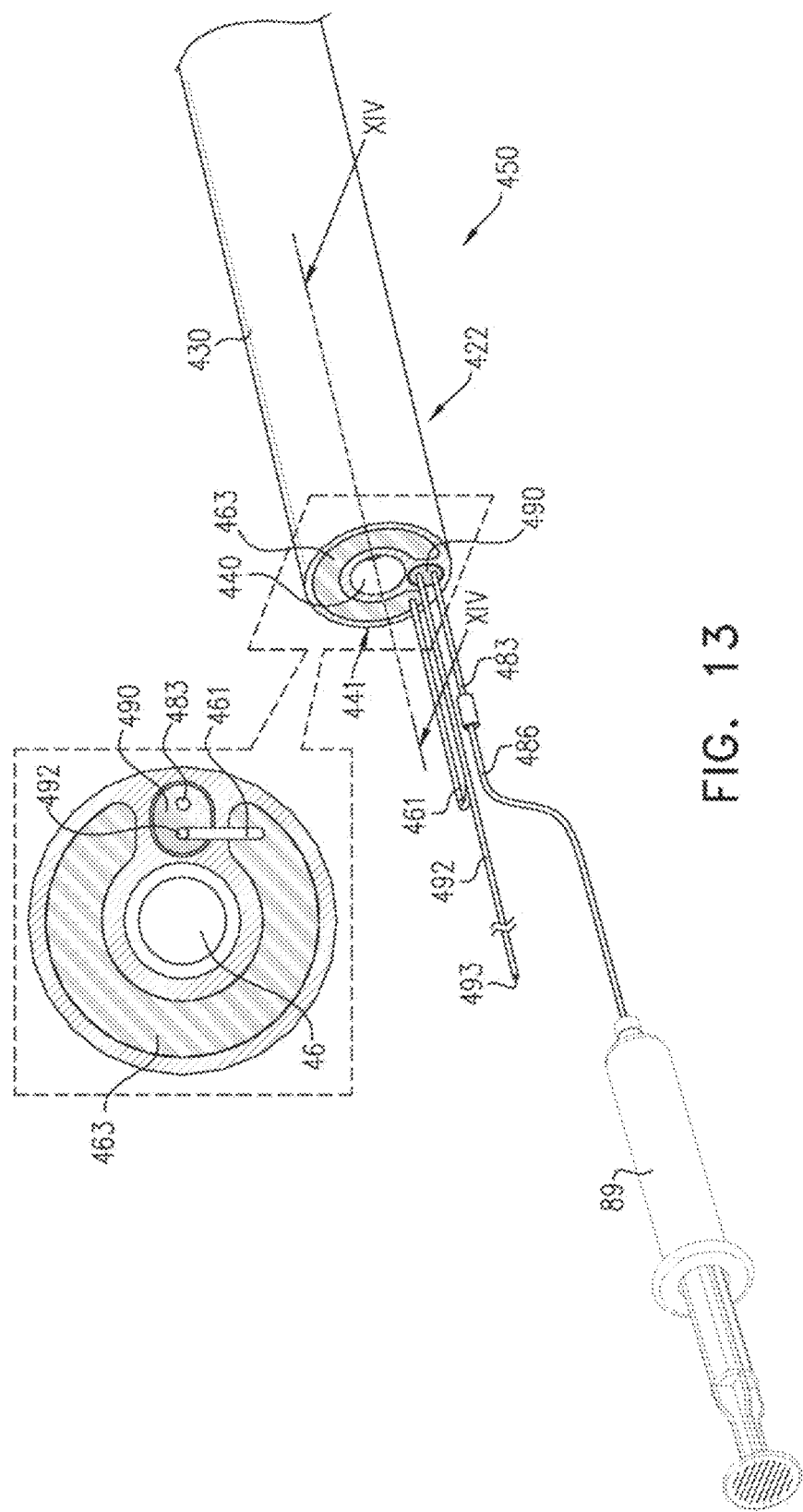
FIG. 13 is a schematic illustration of an alternative configuration of the urinary catheter prosthesis of FIGS. 1A-6C, in accordance with an application of the present invention.

Reference is now made to FIG. 13, which is a schematic illustration of an alternative configuration of urinary catheter prosthesis 20, in accordance with an application of the present invention. This alternative configuration may be implemented in combination with any of the configurations of urinary catheter prosthesis 20 described herein, mutatis mutandis.

Figure 14:
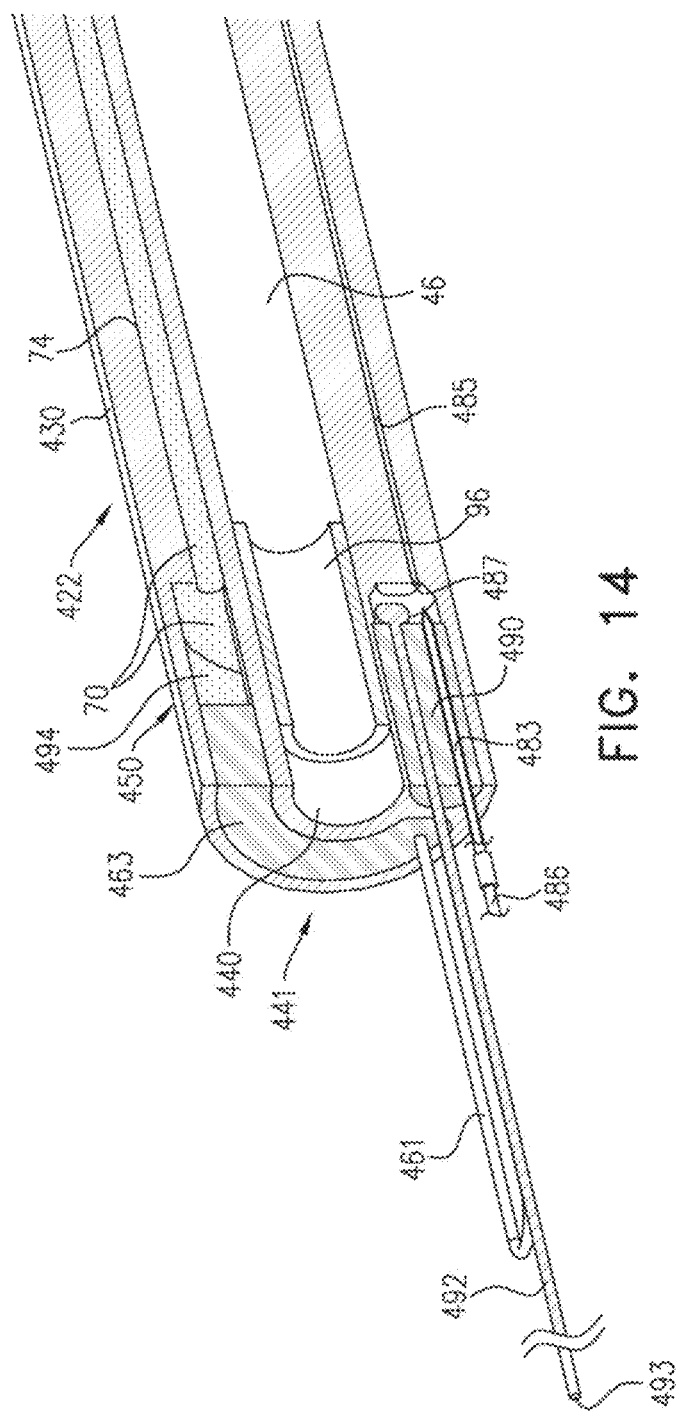
FIG. 14 is a schematic cross-sectional illustration of the alternative configuration of the urinary catheter prosthesis of FIG. 13, taken along line XIV-XIV of FIG. 13, in accordance with an application of the present invention.

Reference is also made to FIG. 14, which is a schematic cross-sectional illustration of the alternative configuration of urinary catheter prosthesis 20, taken along line XIV-XIV of FIG. 13, in accordance with an application of the present invention.

Figure 15A:
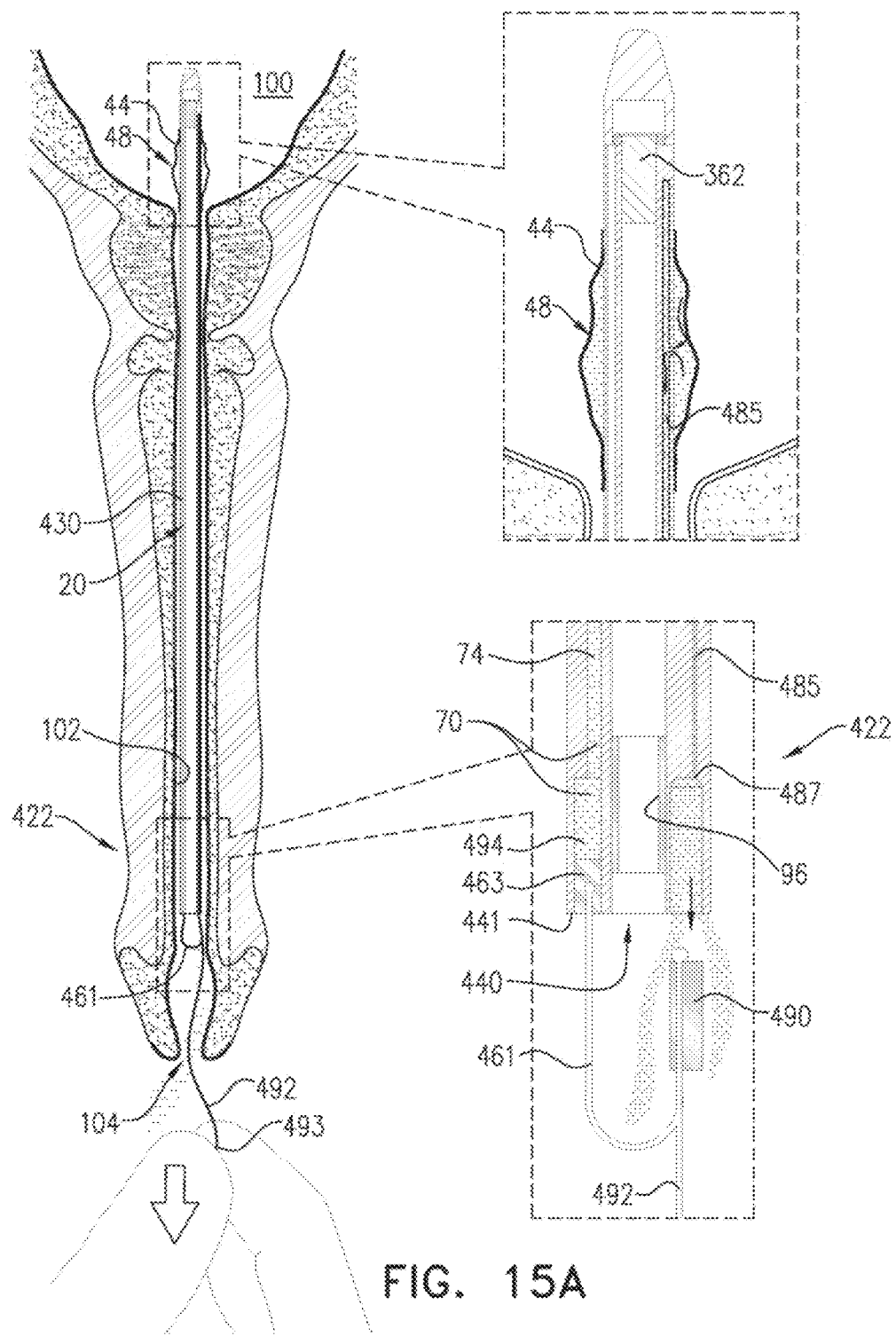
FIGS. 15A-B are schematic illustrations of a portion of a technique for deflating an anchor balloon and removing the urinary catheter prosthesis from the bladder and the urethra, in accordance with respective applications of the present invention.
Figure 15B:
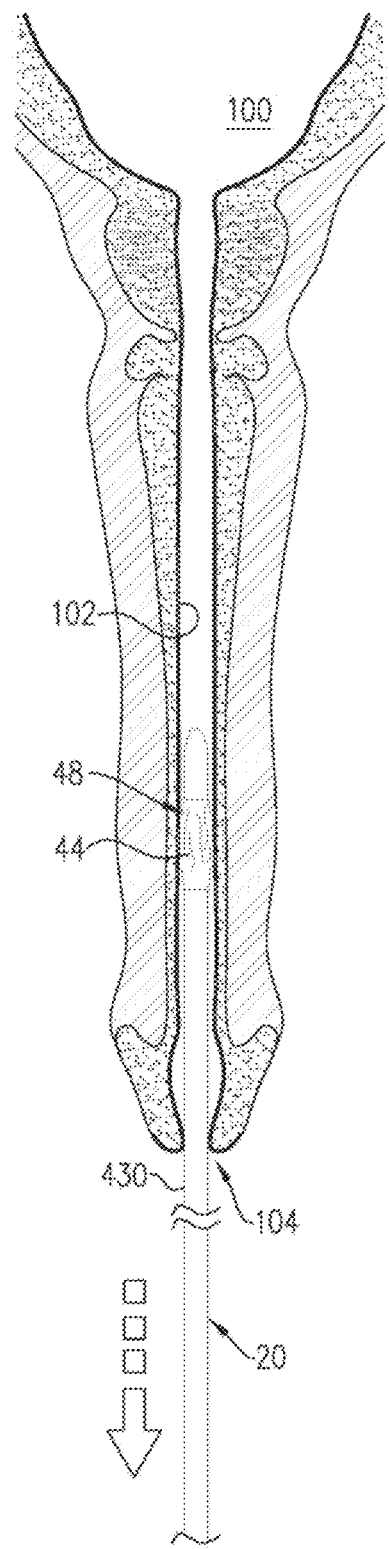

Reference is further made to FIGS. 15A-B, which are schematic illustrations of a portion of a technique for deflating anchor balloon 44 and removing urinary catheter prosthesis 20 from the bladder and urethra 102, in accordance with respective applications of the present invention.

In this configuration, urinary catheter prosthesis 20 comprises a proximal intra-urethral assembly 422, which comprises a flexible intra-urethral catheter 430. Intra-urethral catheter 430 is shaped so as to define a urinary outlet 440 at a proximal end 441 of flexible intra-urethral catheter 430. Other than as described hereinbelow, proximal intra-urethral assembly 422 and flexible intra-urethral catheter 430 are generally similar to proximal intra-urethral assembly 422 and flexible intra-urethral catheter 30, respectively, described hereinabove with reference to FIGS. 1A-6C, and may implement any of the features thereof, mutatis mutandis. Like reference numerals refer to like parts. Proximal intra-urethral assembly 422 may optionally be implemented in combination with any of the configurations of the urinary catheter prosthesis described herein.

For some applications, anchor balloon 44 is inflated via a filling tube 486 that is removably coupled in fluid communication with a proximal end portion 487 of a filling channel 485. Filling channel 485 runs along a portion of flexible intra-urethral catheter 430 (e.g., within a wall of the portion of flexible intra-urethral catheter 430), and has a distal portion in fluid communication with an interior of anchor balloon 44. For example, anchor balloon may be inflated via filling tube 486 using external fluid source 89, e.g., comprising a syringe, such as shown in FIG. 13. After anchor balloon 44 has been inflated, filling tube 486 is decoupled from the fluid communication with proximal end portion 487 of filling channel 485.

Reference is still made to FIGS. 13-15B. For some applications, urinary catheter prosthesis 20 further comprises:

an anchor-balloon plug 490 (instead of anchor-balloon plug 90, described hereinabove with reference to FIGS. 1A-B, 2, and 5C-F); anchor-balloon plug 490 seals anchor balloon 44 when in a sealed state, by blocking proximal end portion 487 of filling channel 485, such as shown in FIGS. 14 and 15A; and the above-mentioned plug-release line 492, which has (a) a proximal end 493 that is disposed proximally beyond proximal end 441 of flexible intra-urethral catheter 430, and (b) a distal portion that is connected to anchor-balloon plug 490; plug-release line 492 may comprise any elongate flexible member, such as a string, wire, cord, or suture.

Optionally, a distal portion or all of filling tube 486 comprises a hollow needle 483, e.g., a hypodermic needle, such as shown in FIGS. 13 and 14. Hollow needle 483 is provided to the subject, pre-inserted, puncturing and passing through anchor-balloon plug 490, such as shown in FIG. 14. Thus, anchor-balloon plug 490 functions as a septum. Filling tube 486 may be connectable to or pre-connected to external fluid source 89.

For some applications, filling tube 486 is decoupled from the fluid communication with proximal end portion 487 of filling channel 485 by proximally pulling filling tube 486 (e.g., hollow needle 483 thereof) from anchor-balloon plug 490. Anchor-balloon plug 490 self-seals upon removal filling tube 486.

For some applications, such as shown in FIG. 15A, bladder anchor 48 is configured such that proximal pulling on plug-release line 492 pulls anchor-balloon plug 490 out of proximal end 441 of flexible intra-urethral catheter 430. This allows the inflation fluid to drain from anchor balloon 44 via filling channel 485, thereby deflating anchor balloon 44 and allowing removal of urinary catheter prosthesis 20 from the bladder. Proximal pulling on plug-release line 492 thus transitions anchor-balloon plug 490 from the sealed state to an open state, in which anchor-balloon plug 490 does not seal anchor balloon 44.

For some applications, pulling on plug-release line 492 also pulls the entire urinary catheter prosthesis 20 from the bladder and urethra 102, such as shown in FIG. 15B. For example, urinary catheter prosthesis 20 may further comprise a catheter-removal cable 461, which is fixedly coupled to plug-release line 492 and to proximal intra-urethral assembly 422. Pulling on plug-release line 492:

first pulls anchor-balloon plug 490 out of proximal end 441 of flexible intra-urethral catheter 430, allowing deflation of anchor balloon 44, and then pulls urinary catheter prosthesis 20 out of the bladder and urethra 102 by pulling on catheter-removal cable 461.

For example, catheter-removal cable 461 may be fixed coupled to an activator fluid-reserve plug 463 that permanently seals a proximal end of a fluid reservoir defined by a control balloon 494 of a hydraulic activator 450. Hydraulic activator 450 and control balloon 494 are generally similar to hydraulic activator 50 and control balloon 94, respectively, described hereinabove with reference to FIGS. 1A-6C, and may implement any of the features thereof, mutatis mutandis. For example, hydraulic activator 450 may comprise counterforce surface 96, which may be shaped as a tube.

Figure 16A:
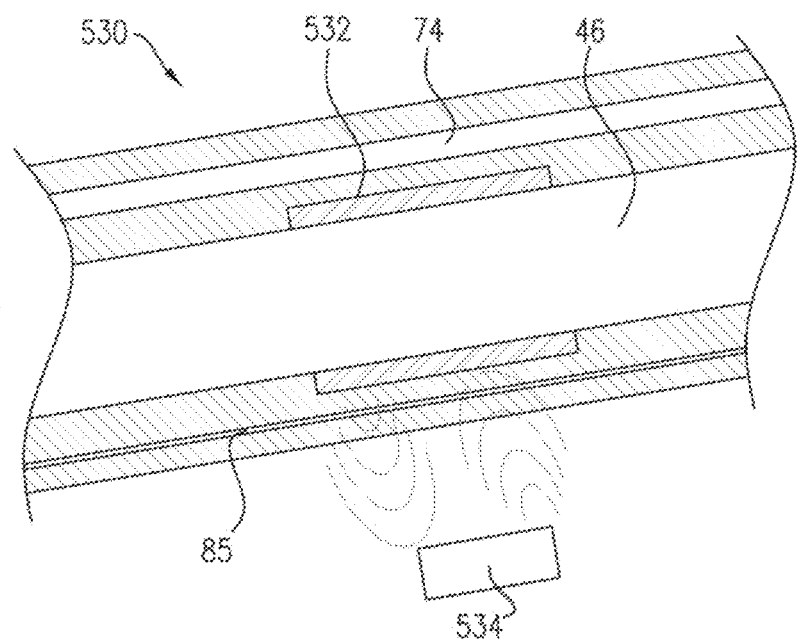
FIGS. 16A-B are schematic cross-sectional illustrations of a portion of a flexible intra-urethral catheter, in accordance with an application of the present invention.
Figure 16B:
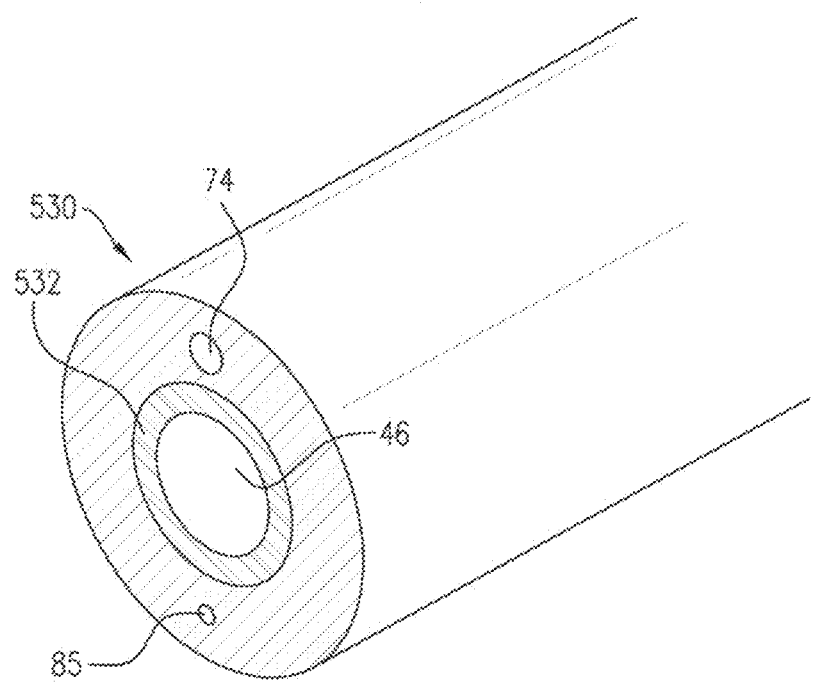

Reference is now made to FIGS. 16A-B, which are schematic cross-sectional illustrations of a portion of a flexible intra-urethral catheter 530, in accordance with an application of the present invention. Flexible intra-urethral catheter 530 may implement any of the techniques of flexible intra-urethral catheter 30 and/or flexible intra-urethral catheter 530, described hereinabove with reference to FIGS. 1A-12C and FIGS. 13-15B, respectively. Any of the configurations of urinary catheter prosthesis 20 described herein may optionally implement the techniques of flexible intra-urethral catheter 530, mutatis mutandis.

Flexible intra-urethral catheter 530 comprises a sensor 532 that is configured to sense, either continuously or periodically, one or more parameters of urine flowing through lumen 46 of the urinary catheter prosthesis (typically through proximal intra-urethral catheter 530). For example, the one or more parameters may include one or more of the following: a flow rate of the urine, a pressure of the urine, a temperature of the urine, and/or a pH level of the urine.

Sensor 532 typically extends partially or entirely around lumen 46, typically without reducing a diameter of the lumen. For example, sensor 532 may be partially or entirely embedded in a wall of flexible intra-urethral catheter 530.

For some applications, sensor 532 comprises a wireless transmitter, which is configured to wirelessly transmit signals indicative of the one or more sensed parameters. An external unit 534 is provided for receiving the transmitted signals. Sensor 532 may optionally also comprise a wireless receiver, for receiving wireless energy from external unit 534.

For some applications, sensor 532 comprises a flexible printed circuit board, which is wrapped partially or entirely around lumen 46.

Optionally, sensor 532 is passive, i.e., comprises only passive electronic components.

Figure 17:
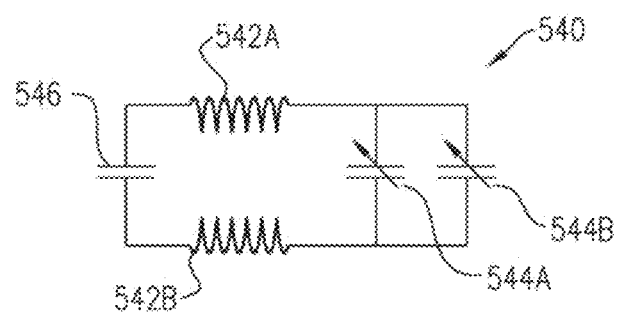
FIG. 17 is a schematic illustration of a resonance circuit, in accordance with an application of the present invention.

Reference is now made to FIG. 17, which is a schematic illustration of a resonance circuit 540, in accordance with an application of the present invention. For some applications in which sensor 532 is configured to sense the flow rate and/or the pressure of the urine, sensor 532 comprises resonance circuit 540, which comprises first and second coils 542A and 542B, first and second capacitors 544A and 544B in parallel with each other, and a third capacitor 546 in series with first and second coils 542A and 542B. First and second coils 542A and 542B are configured to receive and transmit radiation to external unit 534. The difference between the frequency of the signal transmitted from external unit 534 and the frequency of the signal received by sensor 532 is proportional to the flow or the pressure of the urine, based on pre-calibration of sensor 532 and the location of the sensor or the sensors, if more than one sensor is provided to make more than one measurement (e.g., pressure and flow), because of the change of the capacity of first and second capacitors 544A and 544B. Third capacitor 546 is not influenced by flow changes. Optionally, techniques are used that are known for measuring arterial blood pressure and/or flow, mutatis mutandis.

In an embodiment, techniques and apparatus described in one or more of the following applications are combined with techniques and apparatus described in U.S. Provisional Application 62/995,470, filed Jan. 30, 2020, and/or U.S. Provisional Application 63/040,565, filed Jun. 18, 2020, both of which are assigned to the assignee of the present application and are incorporated herein by reference.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. A user-controllable urinary catheter prosthesis for minimally-invasive insertion into a subject, the urinary catheter prosthesis comprising:
 a proximal intra-urethral assembly, which is (a) configured to be disposed entirely within a urethra of the subject by insertion via a meatus of the subject, and (b) comprises:
  a flexible intra-urethral catheter, which is shaped so as to define a urinary outlet at a proximal end of the flexible intra-urethral catheter; and
  a user-activatable hydraulic activator, which is disposed along the flexible intra-urethral catheter;
 a distal bladder assembly, which (a) extends distally from a distal end of the flexible intra-urethral catheter, and (b) is configured to be disposed, by insertion via the urethra, in a bladder of the subject, wherein the urinary catheter prosthesis is shaped so as to define a lumen that defines a urine path between the distal bladder assembly and the urinary outlet;
 a bladder anchor, which is coupled to the distal bladder assembly, and is configured to engage an inner surface of a wall of the bladder when in a deployed configuration, so as to anchor the urinary catheter prosthesis in place; and
 a hydraulic valve, which is disposed distal to the hydraulic activator, and which is configured to assume:
  (a) an open state, in which the hydraulic valve allows urine flow between the distal bladder assembly and the urinary outlet, and
  (b) a closed resting state, in which the hydraulic valve entirely blocks urine from entering the distal bladder assembly, flowing through the lumen, and exiting the urinary outlet,
 wherein the hydraulic activator is configured to transition the hydraulic valve from the closed resting state to the open state upon application of pressure to the hydraulic activator, and
 wherein the hydraulic valve is configured to remain in the open state even after cessation of the application of the pressure to the hydraulic activator.

2. The urinary catheter prosthesis according to claim 1, wherein the hydraulic valve is disposed in the urinary catheter prosthesis distal to the hydraulic activator.

3. The urinary catheter prosthesis according to claim 2, wherein the hydraulic valve is disposed at least partially in the distal bladder assembly.

4. The urinary catheter prosthesis according to claim 1, wherein the distal bladder assembly (a) is shaped so as to define a urinary inlet, and (b) is configured to be disposed, by insertion via the urethra, in the bladder of the subject such that the urinary inlet is disposed in the bladder of the subject, wherein the lumen of the urinary catheter prosthesis defines the urine path between the urinary inlet and the urinary outlet.

5. The urinary catheter prosthesis according to claim 4, wherein the hydraulic valve is configured such that (a) when in the open state, the hydraulic valve allows urine flow between the urinary inlet and the urinary outlet, and (b) when in the closed resting state, the hydraulic valve entirely blocks urine from entering the urinary inlet, flowing through the lumen, and exiting the urinary outlet.

6. The urinary catheter prosthesis according to claim 1, wherein the hydraulic valve comprises a valve balloon, and
wherein the hydraulic valve is configured to assume the open state upon inflation of the valve balloon.

7. The urinary catheter prosthesis according to claim 6, wherein the hydraulic valve comprises the valve balloon and a urinary inlet,
wherein the distal bladder assembly is configured to be disposed, by insertion via the urethra, in the bladder of the subject such that the urinary inlet is disposed in the bladder of the subject,
wherein the lumen of the urinary catheter prosthesis defines the urine path between the urinary inlet and the urinary outlet,
wherein the hydraulic valve is configured such that the urinary inlet is closed when the hydraulic valve is in the closed resting state, and
wherein the hydraulic valve is configured to assume the open state when the valve balloon is inflated sufficiently to open the urinary inlet.

8. The urinary catheter prosthesis according to claim 7, wherein the urinary inlet is shaped so as to define one or more slits that are closed when the hydraulic valve is in the closed resting state, and
wherein the hydraulic valve is configured to assume the open state when the valve balloon is inflated sufficiently to push open the one or more slits.

9. The urinary catheter prosthesis according to claim 6, wherein the hydraulic activator comprises a control balloon,
wherein the urinary catheter prosthesis further comprises a hydraulic tube, which couples the control balloon in hydraulic communication with the valve balloon, and
wherein the control balloon is configured, upon squeezing thereof, to inflate the valve balloon, thereby transitioning the hydraulic valve from the closed resting state to the open state.

10. The urinary catheter prosthesis according to claim 6, wherein the distal bladder assembly is shaped so as to define a urinary inlet,
wherein the distal bladder assembly is configured such that the urinary inlet is closed when the hydraulic valve is in the closed resting state, and
wherein the hydraulic valve is configured to assume the open state when the valve balloon is inflated sufficiently to open the urinary inlet.

11. The urinary catheter prosthesis according to claim 10, wherein the urinary inlet is shaped so as to define one or more slits that are closed when the hydraulic valve is in the closed resting state, and
wherein the hydraulic valve is configured to assume the open state when the valve balloon is inflated sufficiently to push open the one or more slits.

12. The urinary catheter prosthesis according to claim 1, wherein the hydraulic valve is configured, after remaining in the open state even after the cessation of the application of the pressure to the hydraulic activator, to automatically transition to the closed resting state such that the hydraulic valve assumes the closed resting state a set amount of time after being transitioned to the open state.

13. The urinary catheter prosthesis according to claim 12, wherein the set amount of time has a value that falls in a range of 15 to 360 seconds.

14. The urinary catheter prosthesis according to claim 12, wherein the hydraulic valve further comprises a spring, which is configured to store elastic energy during transitioning of the hydraulic valve from the closed resting state to the open state, and to automatically transition the hydraulic valve to the closed resting state by releasing the elastic energy.

15. The urinary catheter prosthesis according to claim 14, wherein the urinary catheter prosthesis comprises hydraulic liquid, and the hydraulic valve comprises a piston,
wherein the hydraulic activator is configured to transition the hydraulic valve from the closed resting state to the open state by transferring at least a portion of the hydraulic liquid from the hydraulic activator to the hydraulic valve, and
wherein the urinary catheter prosthesis further comprises a hydraulic one-way shutter that is configured to delay return of the hydraulic liquid from the hydraulic valve to the hydraulic activator, thereby delaying the piston from automatically transitioning from the open state to the closed resting state, such that the hydraulic valve assumes the closed resting state the set amount of time after being transitioned to the open state.

16. The urinary catheter prosthesis according to claim 1, wherein the urinary catheter prosthesis is configured to be minimally-invasive inserted into a female subject.

17. The urinary catheter prosthesis according to claim 1, wherein the hydraulic activator comprises a control balloon, which is configured, upon squeezing thereof, to transition the hydraulic valve from the closed resting state to the open state.

18. The urinary catheter prosthesis according to claim 17, further comprising a hydraulic tube, which couples the control balloon in hydraulic communication with the hydraulic valve such that the hydraulic valve transitions from the closed resting state to the open state upon the squeezing of the control balloon.

19. The urinary catheter prosthesis according to claim 18, wherein the hydraulic valve comprises a piston, and wherein the hydraulic tube couples the control balloon in the hydraulic communication with the piston.

20. The urinary catheter prosthesis according to claim 1, wherein the urinary catheter prosthesis does not comprise any electrical components.

21. The urinary catheter prosthesis according to claim 1, wherein the hydraulic activator is configured to transition the hydraulic valve from the closed resting state to the open state upon application, to the hydraulic activator, of the pressure entirely radially inwardly toward a central longitudinal axis of the hydraulic activator.

22. A user-controllable urinary catheter prosthesis for minimally-invasive insertion into a subject, the urinary catheter prosthesis comprising:
a proximal intra-urethral assembly, which is (a) configured to be disposed entirely within a urethra of the subject by insertion via a meatus of the subject, and (b) comprises:
a flexible intra-urethral catheter, which is shaped so as to define a urinary outlet at a proximal end of the flexible intra-urethral catheter; and a user-activatable hydraulic activator, which is disposed along the flexible intra-urethral catheter;
a distal bladder assembly, which (a) extends distally from a distal end of the flexible intra-urethral catheter, and (b) is configured to be disposed, by insertion via the urethra, in a bladder of the subject, wherein the urinary catheter prosthesis is shaped so as to define a lumen that defines a urine path between the distal bladder assembly and the urinary outlet;
a bladder anchor, which is coupled to the distal bladder assembly, and is configured to engage an inner surface of a wall of the bladder when in a deployed configuration, so as to anchor the urinary catheter prosthesis in place; and
a hydraulic valve, which is disposed distal to the hydraulic activator, and which is configured to assume:
  (a) an open state, in which the hydraulic valve allows urine flow between the distal bladder assembly and the urinary outlet, and
  (b) a closed resting state, in which the hydraulic valve entirely blocks urine from entering the distal bladder assembly, flowing through the lumen, and exiting the urinary outlet,
wherein the hydraulic activator is configured to transition the hydraulic valve from the closed resting state to the open state upon application of pressure to the hydraulic activator,
wherein the hydraulic valve (160) comprises a valve balloon (164),
wherein the hydraulic valve (160) is configured to assume the open state upon inflation of the valve balloon (164),
wherein a distal portion of the distal bladder assembly comprises a tubular casing, which is shaped so as to define a urinary inlet through the tubular casing at an axial position along the tubular casing,
wherein the distal bladder assembly is configured to be disposed, by insertion via the urethra, in the bladder of the subject such that the urinary inlet is disposed in the bladder of the subject, wherein the lumen of the urinary catheter prosthesis defines the urine path between the urinary inlet and the urinary outlet,
wherein the hydraulic valve further comprises an elastic sleeve, which (a) defines one or more openings through the elastic sleeve, (b) is sealingly coupled to the tubular casing, and (c) surrounds the tubular casing, including at the axial position of the urinary inlet,
wherein the hydraulic valve is configured such that when it is in the closed resting state, the elastic sleeve entirely occludes the urinary inlet, and
wherein the hydraulic valve is configured to assume the open state when the valve balloon is inflated sufficiently to radially expand the elastic sleeve such that the elastic sleeve (a) does not occlude the urinary inlet and (b) defines a fluid flow path between (i) the one or more openings through the elastic sleeve and (ii) the urinary inlet.

23. The urinary catheter prosthesis according to claim 22, wherein an axial position of the valve balloon along the distal bladder assembly is at least partially non-axially-overlapping with the axial position of the urinary inlet.

24. The urinary catheter prosthesis according to claim 22, wherein the one or more openings through the elastic sleeve are located at respective radial positions around the tubular casing that are entirely non-radially-overlapping with a radial position of the urinary inlet around the tubular casing.

25. A user-controllable urinary catheter prosthesis for minimally-invasive insertion into a subject, the urinary catheter prosthesis comprising:
a proximal intra-urethral assembly, which is (a) configured to be disposed entirely within a urethra of the subject by insertion via a meatus of the subject, and (b) comprises:
  a flexible intra-urethral catheter, which is shaped so as to define a urinary outlet at a proximal end of the flexible intra-urethral catheter; and
  a user-activatable hydraulic activator, which is disposed along the flexible intra-urethral catheter;
a distal bladder assembly, which (a) extends distally from a distal end of the flexible intra-urethral catheter, and (b) is configured to be disposed, by insertion via the urethra, in a bladder of the subject, wherein the urinary catheter prosthesis is shaped so as to define a lumen that defines a urine path between the distal bladder assembly and the urinary outlet;
a bladder anchor, which is coupled to the distal bladder assembly, and is configured to engage an inner surface of a wall of the bladder when in a deployed configuration, so as to anchor the urinary catheter prosthesis in place; and
a hydraulic valve, which is disposed distal to the hydraulic activator, and which is configured to assume:
  (a) an open state, in which the hydraulic valve allows urine flow between the distal bladder assembly and the urinary outlet, and
  (b) a closed resting state, in which the hydraulic valve entirely blocks urine from entering the distal bladder assembly, flowing through the lumen, and exiting the urinary outlet,
wherein the hydraulic activator is configured to transition the hydraulic valve from the closed resting state to the open state upon application of pressure to the hydraulic activator,
wherein the hydraulic valve comprises a piston.

26. A user-controllable urinary catheter prosthesis for minimally-invasive insertion into a subject, the urinary catheter prosthesis comprising:
a proximal intra-urethral assembly, which is (a) configured to be disposed entirely within a urethra of the subject by insertion via a meatus of the subject, and (b) comprises:
  a flexible intra-urethral catheter, which is shaped so as to define a urinary outlet at a proximal end of the flexible intra-urethral catheter; and
  a user-activatable hydraulic activator, which is disposed along the flexible intra-urethral catheter;
a distal bladder assembly, which (a) extends distally from a distal end of the flexible intra-urethral catheter, and (b) is configured to be disposed, by insertion via the urethra, in a bladder of the subject, wherein the urinary catheter prosthesis is shaped so as to define a lumen that defines a urine path between the distal bladder assembly and the urinary outlet;
a bladder anchor, which is coupled to the distal bladder assembly, and is configured to engage an inner surface of a wall of the bladder when in a deployed configuration, so as to anchor the urinary catheter prosthesis in place; and
a hydraulic valve, which is disposed distal to the hydraulic activator, and which is configured to assume:
  (a) an open state, in which the hydraulic valve allows urine flow between the distal bladder assembly and the urinary outlet, and (b) a closed resting state, in which the hydraulic valve entirely blocks urine from entering the distal bladder assembly, flowing through the lumen, and exiting the urinary outlet, wherein the hydraulic activator is configured to transition the hydraulic valve from the closed resting state to the open state upon application of pressure to the hydraulic activator, wherein the hydraulic valve comprises a valve balloon, wherein the hydraulic valve is configured to assume the open state upon inflation of the valve balloon, wherein the distal bladder assembly is shaped so as to define a urinary inlet, wherein the hydraulic valve further comprises a valve plug, which is attached to the valve balloon, and which is configured to occlude the urinary inlet when the hydraulic valve is in the closed resting state, and wherein the hydraulic valve is configured such that the inflation of the valve balloon moves the valve plug away from the urinary inlet, thereby transitioning the hydraulic valve to the open state.

27. A user-controllable urinary catheter prosthesis for minimally-invasive insertion into a subject, the urinary catheter prosthesis comprising:
- a proximal intra-urethral assembly, which is (a) configured to be disposed entirely within a urethra of the subject by insertion via a meatus of the subject, and (b) comprises:
  - a flexible intra-urethral catheter, which is shaped so as to define a urinary outlet at a proximal end of the flexible intra-urethral catheter; and
  - a user-activatable hydraulic activator, which is disposed along the flexible intra-urethral catheter;
- a distal bladder assembly, which (a) extends distally from a distal end of the flexible intra-urethral catheter, and (b) is configured to be disposed, by insertion via the urethra, in a bladder of the subject, wherein the urinary catheter prosthesis is shaped so as to define a lumen that defines a urine path between the distal bladder assembly and the urinary outlet;
- a bladder anchor, which is coupled to the distal bladder assembly, and is configured to engage an inner surface of a wall of the bladder when in a deployed configuration, so as to anchor the urinary catheter prosthesis in place; and
- a hydraulic valve, which is disposed distal to the hydraulic activator, and which is configured to assume:
  - (a) an open state, in which the hydraulic valve allows urine flow between the distal bladder assembly and the urinary outlet, and
  - (b) a closed resting state, in which the hydraulic valve entirely blocks urine from entering the distal bladder assembly, flowing through the lumen, and exiting the urinary outlet, wherein the hydraulic activator is configured to transition the hydraulic valve from the closed resting state to the open state upon application of pressure to the hydraulic activator, wherein the bladder anchor comprises an anchor balloon, which is configured to engage the bladder wall around a bladder neck when the anchor balloon is in an inflated deployed configuration, wherein the bladder anchor further comprises:
- an anchor-balloon plug, which seals the anchor balloon when in a sealed state; and
- a plug-release line, which has a proximal end that is disposed proximally beyond the proximal end of the flexible intra-urethral catheter, and a distal portion that is connected to the anchor-balloon plug, wherein the bladder anchor is configured such that proximal pulling on the plug-release line transitions the anchor-balloon plug from the sealed state to an open state, in which the anchor-balloon plug does not seal the anchor balloon, wherein the urinary catheter prosthesis further comprises:
- a filling channel, which runs along a portion of the flexible intra-urethral catheter and has a distal end portion in fluid communication with an interior of the anchor balloon; and
- a filling tube, which is removably coupled in fluid communication with a proximal end portion of the filling channel, wherein the hydraulic activator comprises:
- a control balloon, which is configured, upon squeezing thereof, to transition the hydraulic valve from the closed resting state to the open state; and
- a tubular counterforce surface against which the control balloon presses upon application of the pressure, wherein the counterforce surface is more rigid than the flexible intra-urethral catheter, wherein the tubular counterforce surface is shaped so as to define a lateral opening, and wherein the filling tube passes through the lateral opening when the filling tube is removably coupled in the fluid communication with the proximal end portion of the filling channel.

28. The urinary catheter prosthesis according to claim 27, wherein the hydraulic valve is configured to remain in the open state even after cessation of the application of the pressure to the hydraulic activator.

* * * * *